US012018324B2

(12) United States Patent
Katsuragi et al.

(10) Patent No.: US 12,018,324 B2
(45) Date of Patent: Jun. 25, 2024

(54) METHOD OF DETECTING MINOR BCR-ABL1 GENE

(71) Applicant: OTSUKA PHARMACEUTICAL CO., LTD., Tokyo (JP)

(72) Inventors: Kiyonori Katsuragi, Osaka (JP); Hideaki Tanaka, Osaka (JP); Ryuta Ito, Osaka (JP); Daisuke Koga, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 185 days.

(21) Appl. No.: 16/607,314

(22) PCT Filed: Apr. 25, 2018

(86) PCT No.: PCT/JP2018/016749

§ 371 (c)(1),
(2) Date: Oct. 22, 2019

(87) PCT Pub. No.: WO2018/199137

PCT Pub. Date: Nov. 1, 2018

(65) Prior Publication Data

US 2020/0377928 A1 Dec. 3, 2020

(30) Foreign Application Priority Data

Apr. 26, 2017 (JP) ................................. 2017-087666

(51) Int. Cl.
*C12Q 1/68* (2018.01)
*C12N 15/10* (2006.01)
(Continued)

(52) U.S. Cl.
CPC ......... *C12Q 1/686* (2013.01); *C12N 15/1096* (2013.01); *C12Q 1/6886* (2013.01); *C12Q 2561/113* (2013.01)

(58) Field of Classification Search
None
See application file for complete search history.

(56) References Cited

U.S. PATENT DOCUMENTS 5,652,222 A * 7/1997 Calabretta .......... C12N 15/1135 435/375
6,080,851 A * 6/2000 Pachuk .................. A61P 31/12 435/375

(Continued)

FOREIGN PATENT DOCUMENTS

CN 103627802 A 3/2014
JP 2002-136300 A 5/2002

(Continued)

OTHER PUBLICATIONS

Kreuzer et al. Preexistence and evolutionof imatinib mesylate-resistant clones in chronic myelogenous leukemia detected by a PNA-based PCR clamping technique. Ann Hematol., vol. 82, p. 284-289, 2003.*

(Continued)

*Primary Examiner* — Stephanie K Mummert
(74) *Attorney, Agent, or Firm* — Sughrue Mion, PLLC

(57) ABSTRACT

The disclosure provides a method comprising (1) conducting a PCR using a nucleic acid sample obtained from the subject as the template, a forward primer having a nucleic acid sequence of a part of exon 1 of the BCR gene, and a reverse primer having a nucleic acid sequence complementary to a part of exons 2 to 11 of the ABL1 gene, in the presence of a modified nucleic acid having a nucleic acid sequence of a part of exons 2 to 14 of the BCR gene or a nucleic acid sequence complementary thereto; and (2) determining that the subject has the minor BCR-ABL1 gene when the nucleic acid amplification is occurred in the PCR.

19 Claims, 17 Drawing Sheets

Specification includes a Sequence Listing.

m-*bcr*: *BCR-ABL* p190
type
e1-a2
*BCR* (22q11)
*ABL* (9q34)
1 2 3 4
Forward primer
Probe
Reverse primer M-*bcr*: *BCR-ABL* p210
type
b3-a2
1 12 13 14 2 3 4
b2-a2
1 12 13 2 3 4
Forward primer
Probe
M-BCR clamp
Reverse primer

(51) Int. Cl.
*C12Q 1/686* (2018.01)
*C12Q 1/6886* (2018.01)

(56) References Cited

U.S. PATENT DOCUMENTS

| | | | | |
|---|---|---|---|---|
| 6,391,592 | B1 | 5/2002 | Su et al. | |
| 2002/0076767 | A1 | 6/2002 | Su et al. | |
| 2002/0192645 | A1 | 12/2002 | Tseng et al. | |
| 2010/0174055 | A1 * | 7/2010 | Tseng .................. | C12Q 1/6886 536/22.1 |

FOREIGN PATENT DOCUMENTS

| | | | |
|---|---|---|---|
| JP | 2005-536193 | A | 12/2005 |
| KR | 10-2012-0088891 | A | 8/2012 |
| WO | 03/095680 | A1 | 11/2003 |

OTHER PUBLICATIONS

Kang HH, et al. Genotyping of chimerical BCR-ABL1 RNA in chronic myeloid leukemia by intigrated DNA chip. The Journal of Molecular Diagnostics, vol. 14(5), p. 487-493, 2012.*
Rosso V, et al. Detection of BCR-ABL1 T3151 mutation by peptide nucleic acid directed clamping and peptide nucleic aicd FISH. Biomarker Research vol. 3(15), p. 1-5, 2015.*
Kang et al. (J Molecular Diagnostics, vol. 14(5), p. 487-493, 2012) (Year: 2012).*
Kreuzer et al. (Ann Hematology, 2003, 82:284-289) (Year: 2003).*
Van Dongen, JJM., et al., "Standardized RT-PCR analysis of fusion gene transcripts from chromosome aberrations in acute leukemia for detection of minimal residual disease. Report of the BIOMED-1 Concerted Action: investigation of minimal residual disease in acute lekumia", Leukemia, 1999, vol. 13, issue 12, pp. 1901-1928, 28 pages total.
Gabert, J., et al., "Standardization and quality control studies of 'real time' quantitative reverse transcriptase polymerase chain reaction of fusion gene transcripts for residual disease detection in leukemia—A Europe Against Cancer Program", Leukemia, 2003, vol. 17, issue 12, pp. 2318-2357, 40 pages total.
International Search Report dated Jul. 31, 2018 issued by the International Searching Authority in International Application No. PCT/JP2018/016749.
International Preliminary Report on Patentability with the translation of Written Opinion Oct. 29, 2019 issued by the International Searching Authority in International Application No. PCT/JP2018/016749.
Extended European Search Report dated Dec. 7, 2020, from the European Patent Office in European Application No. 18791478.3.
Kreuzer K-A. et al., "Preexistence and evolution of imatinib mesylate-resistant clones in chronic myelogenous leukemia detected by a PNA-based PCR clamping technique", Annals of Hematology, vol. 82, No. 5, 2003, pp. 284-289 (6 Pages Total).
Kreuzer et al., "LightCycler Technology for the Quantitation of bcr/abl Fusion Transcripts", Cancer Research 59, pp. 3171-3174, Jul. 1, 1999, 5 pages total.
Manfred Schwab, "Encyclopedia of Cancer", Springer-Verlag, 2008, 2nd Edition, p. 320 (3 pages total).
Xianfeng Wang, "Latest Practical Manual of Infectious Diseases and National Mandatory Standards and Norms", Military Medical Science and Technology Electronic Press, 2009, vol. 1, p. 172 (5 pages total).
Office Action issued Nov. 25, 2023 in Chinese Application No. 201880026977.7.
Jeffrey C. Hall, et al., "Advances in Genetics", Elsevier, 2006, vol. 56, pp. 2-4 and 35-36 (8 pages total).

* cited by examiner

Fig. 1
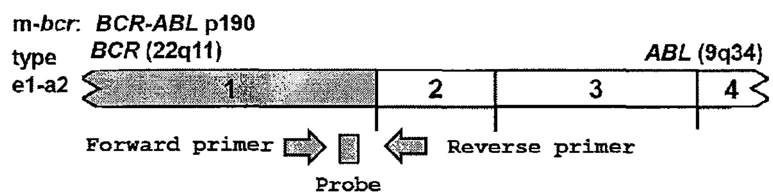
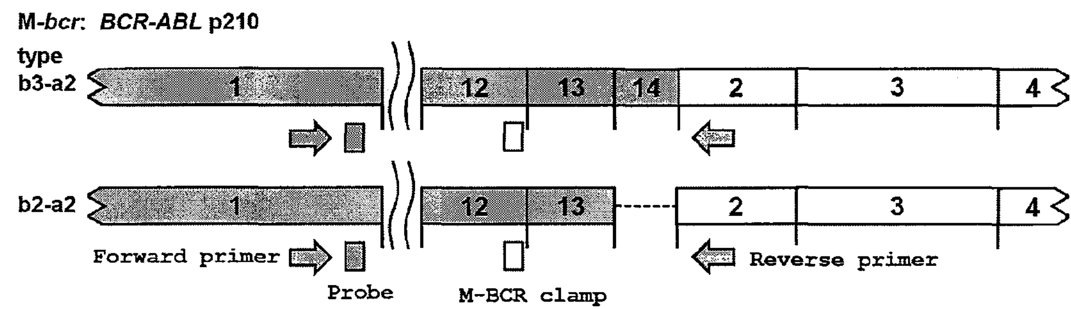

Fig. 2-1

GGGGGGAGGGTGGCGGCTCGATGGGGGAGCCGCCTCCAGGGGGCCCCCCGCCCTGTGCCCACGGCGCGG ⇦ BCR exon 1
CCCCTTTAAGAGGCCCGCCTGGCTCCGTCATCCGCGCCGCGGCCACCTCCCCCCGGCCCTCCCCTTCCTG
CGGCGCAGAGTGCGGGCCGGGCGGGAGTGCGGCGAGAGCCGGCTGGCTGAGCTTAGCGTCCGAGGAGGCG
GCGGCGGCGGCGGCGGCACGGCGGCGGCGGGGCTGTGGGGCGGTGCGGAAGCGAGAGGCGAGGAGCGCGC
GGGCCGTGGCCAGAGTCTGGCGGCGGCCTGGCGGAGCGGAGAGCAGCGCCCGCGCCTCGCCGTGCGGAGG
AGCCCCGCACACAATAGCGGCGCGCGCAGCCCGCGCCCTTCCCCCCGGCGCGCCCCGCCCCGCGCGCCGA
GCGCCCCGCTCCGCCTCACCTGCCACCAGGGAGTGGGCGGGCATTGTTCGCCGCCGCCGCCGCCGCGCGG
GCCATGGGGGCCGCCCGGCGCCCGGGGCCGGGCTGGCGAGGCGCCGCGCCGCCGCTGAGACGGGCCCCGC
GCGCAGCCCGGCGGCGCAGGTAAGGCCGGCCGCGCCATGGTGGACCCGGTGGGCTTCGCGGAGGCGTGGA
AGGCGCAGTTCCCGGACTCAGAGCCCCCGCGCATGGAGCTGCGCTCAGTGGGCGACATCGAGCAGGAGCT
GGAGCGCTGCAAGGCCTCCATTCGGCGCCTGGAGCAGGAGGTGAACCAGGAGCGCTTCCGCATGATCTAC
CTGCAGACGTTGCTGGCCAAGGAAAAGAAGAGCTATGACCGGCAGCGATGGGGCTTCCGGCGCGCGGCGC
AGGCCCCCGACGGCGCCTCCGAGCCCCGAGCGTCCGCGTCGCGCCCGCAGCCAGCGCCCGCCGACGGAGC
CGACCCGCCGCCCGCCGAGGAGCCCGAGGCCCGGCCCGACGGCGAGGGTTCTCCGGGTAAGGCCAGGCCC
GGGACCGCCCGCAGGCCCGGGGCAGCCGCGTCGGGGGAACGGGACGACCGGGGACCCCCCGCCAGCGTGG
CGGCGCTCAGGTCCAACTTCGAGCGGATCCGCAAGGGCCATGGCCAGCCCGGGGCGGACGCCGAGAAGCC
CTTCTACGTGAACGTCGAGTTTCACCACGAGCGCGGCCTGGTGAAGGTCAACGACAAAGAGGTGTCGGAC
CGCATCAGCTCCCTGGGCAGCCAGGCCATGCAGATGGAGCGCAAAAAGTCCCAGCACGGCGCGGGCTCGA
GCGTGGGGGATGCATCCAGGCCCCCTTACCGGGGACGCTCCTCGGAGAGCAGCTGCGGCGTCGACGGCGA
CTACGAGGACGCCGAGTTGAACCCCCGCTTCCTGAAGGACAACCTGATCGACGCCAATGGCGGTAGCAGG
CCCCCTTGGCCGCCCCTGGAGTACCAGCCCTACCAGAGCATCTACGTCGGGGGCATGATGGAAGGGGAGG
GCAAGGGCCCGCTCCTGCGCAGCCAGAGCACCTCTGAGCAGGAGAAGCGCCTTACCTGGCCCCGCAGGTC
CTACTCCCCCCGGAGTTTTGAGGATTGCGGAGGCGGCTATACCCCGGACTGCAGCTCCAATGAGAACCTC
ACCTCCAGCGAGGAGGACTTCTCCTCTGGCCAGTCCAGCCGCGTGTCCCCAAGCCCCACCACCTACCGCA
TGTTCCGGGACAAAAGCCGCTCTCCCTCGCAGAACTCGCAACAGTCCTTCGACAGCAGCAGTCCCCCCAC
GCCGCAGTGCCATAAGCGGCACCGGCACTGCCCGGTTGTCGTGTCCGAGGCCACCATCGTGGGCGTCCGC
AAGACCGGGCAGATCTGGCCCAACGATGGCGAGGGCGCCTTCCATGGAGACGCAG AAGCCCTTCAGCGG ⇦ ABL exon 2
CCAGTAGCATCTGACTTTGAGCCTCAGGGTCTGAGTGAAGCCGCTCGTTGGAACTCCAAGGAAAACCTTC
TCGCTGGACCCAGTGAAAATGACCCCAACCTTTTCGTTGCACTGTATGATTTTGTGGCCAGTGGAGATAA
CACTCTAAGCATAACTAAAG GTGAAAAGCTCCGGGTCTTAGGCTATAATCACAATGGGGAATGGTGTGA ⇦ ABL exon 3
AGCCCAAACCAAAAATGGCCAAGGCTGGGTCCCAAGCAACTACATCACGCCAGTCAACAGTCTGGAGAAA
CACTCCTGGTACCATGGGCCTGTGTCCCGCAATGCCGCTGAGTATCTGCTGAGCAGCGGGATCAATGGCA
GCTTCTTGGTGCGTGAGAGTGAGAGCAGTCCTGGCCAGAGGTCCATCTCGCTGAGATACGAAGGGAGGGT
GTACCATTACAGGATCAACACTGCTTCTGATGGCAAG CTCTACGTCTCCTCCGAGAGCCGCTTCAACAC ⇦ ABL exon 4
CCTGGCCGAGTTGGTTCATCATCATTCAACGGTGGCCGACGGGCTCATCACCACGCTCCATTATCCAGCC
CCAAAGCGCAACAAGCCCACTGTCTATGGTGTGTCCCCCAACTACGACAAGTGGGAGATGGAACGCACGG

Fig. 2-2

ACATCACCATGAAGCACAAGCTGGGCGGGGGCCAGTACGGGGAGGTGTACGAGGGCGTGTGGAAGAAATA ⇦ABL exon 4
CAGCCTGACGGTGGCCGTGAAGACCTTGAAG GAGGACACCATGGAGGTGGAAGAGTTCTTGAAAGAAGC ⇦ABL exon 5
TGCAGTCATGAAAGAGATCAAACACCCTAACCTGGTGCAGCTCCTTG GGGTCTGCACCCGGGAGCCCCC ⇦ABL exon 6
GTTCTATATCATCACTGAGTTCATGACCTACGGGAACCTCCTGGACTACCTGAGGGAGTGCAACCGGCAG
GAGGTGAACGCCGTGGTGCTGCTGTACATGGCCACTCAGATCTCGTCAGCCATGGAGTACCTGGAGAAGA
AAAACTTCATCCACAG AGATCTTGCTGCCCGAAACTGCCTGGTAGGGGAGAACCACTTGGTGAAGGTAG ⇦ABL exon 7
CTGATTTTGGCCTGAGCAGGTTGATGACAGGGGACACCTACACAGCCCATGCTGGAGCCAAGTTCCCCAT
CAAATGGACTGCACCCGAGAGCCTGGCCTACAACAAGTTCTCCATCAAGTCCGACGTCTGGG CATTTGG ⇦ABL exon 8
AGTATTGCTTTGGGAAATTGCTACCTATGGCATGTCCCCTTACCCGGGAATTGACCTGTCCCAGGTGTAT
GAGCTGCTAGAGAAGGACTACCGCATGGAGCGCCCAGAAGGCTGCCCAGAGAAGGTCTATGAACTCATGC
GAGCAT GTTGGCAGTGGAATCCCTCTGACCGGCCCTCCTTTGCTGAAATCCACCAAGCCTTTGAAACAA ⇦ABL exon 9
TGTTCCAGGAATCCAGTATCTCAGACG AAGTGGAAAAGGAGCTGGGGAAACAAGGCGTCCGTGGGGCTG ⇦ABL exon 10
TGAGTACCTTGCTGCAGGCCCCAGAGCTGCCCACCAAGACGAGGACCTCCAGGAGAGCTGCAGAGCACAG
AGACACCACTGACGTGCCTGAGATGCCTCACTCCAAGGGCCAGGGAGAGAGCG ATCCTCTGGACCATGA ⇦ABL exon 11
GCCTGCCGTGTCTCCATTGCTCCCTCGAAAAGAGCGAGGTCCCCCGGAGGGCGGCCTGAATGAAGATGAG
CGCCTTCTCCCCAAAGACAAAAAGACCAACTTGTTCAGCGCCTTGATCAAGAAGAAGAAGAAGACAGCCC
CAACCCCTCCCAAACGCAGCAGCTCCTTCCGGGAGATGGACGGCCAGCCGGAGCGCAGAGGGGCCGGCGA
GGAAGAGGGCCGAGACATCAGCAACGGGGCACTGGCTTTCACCCCCTTGGACACAGCTGACCCAGCCAAG
TCCCCAAAGCCCAGCAATGGGGCTGGGGTCCCCAATGGAGCCCTCCGGGAGTCCGGGGGCTCAGGCTTCC
GGTCTCCCCACCTGTGGAAGAAGTCCAGCACGCTGACCAGCAGCCGCCTAGCCACCGGCGAGGAGGAGGG
CGGTGGCAGCTCCAGCAAGCGCTTCCTGCGCTCTTGCTCCGCCTCCTGCGTTCCCCATGGGGCCAAGGAC
ACGGAGTGGAGGTCAGTCACGCTGCCTCGGGACTTGCAGTCCACGGGAAGACAGTTTGACTCGTCCACAT
TTGGAGGGCACAAAAGTGAGAAGCCGGCTCTGCCTCGGAAGAGGGCAGGGGAGAACAGGTCTGACCAGGT
GACCCGAGGCACAGTAACGCCTCCCCCCAGGCTGGTGAAAAAGAATGAGGAAGCTGCTGATGAGGTCTTC
AAAGACATCATGGAGTCCAGCCCGGGCTCCAGCCCGCCCAACCTGACTCCAAAACCCCTCCGGCGGCAGG
TCACCGTGGCCCCTGCCTCGGGCCTCCCCCACAAGGAAGAAGCTGGAAAGGGCAGTGCCTTAGGGACCCC
TGCTGCAGCTGAGCCAGTGACCCCCACCAGCAAAGCAGGCTCAGGTGCACCAGGGGGCACCAGCAAGGGC
CCCGCCGAGGAGTCCAGAGTGAGGAGGCACAAGCACTCCTCTGAGTCGCCAGGGAGGGACAAGGGGAAAT
TGTCCAGGCTCAAACCTGCCCCGCCGCCCCCACCAGCAGCCTCTGCAGGGAAGGCTGGAGGAAAGCCCTC
GCAGAGCCCGAGCCAGGAGGCGGCCGGGGAGGCAGTCCTGGGCGCAAAGACAAAAGCCACGAGTCTGGTT
GATGCTGTGAACAGTGACGCTGCCAAGCCCAGCCAGCCGGGAGAGGGCCTCAAAAAGCCCGTGCTCCCGG
CCACTCCAAAGCCACAGTCCGCCAAGCCGTCGGGGACCCCCATCAGCCCAGCCCCCGTTCCCTCCACGTT
GCCATCAGCATCCTCGGCCCTGGCAGGGGACCAGCCGTCTTCCACCGCCTTCATCCCTCTCATATCAACC
CGAGTGTCTCTTCGGAAAACCCGCCAGCCTCCAGAGCGGATCGCCAGCGGCGCCATCACCAAGGGCGTGG
TCCTGGACAGCACCGAGGCGCTGTGCCTCGCCATCTCTAGGAACTCCGAGCAGATGGCCAGCCACAGCGC
AGTGCTGGAGGCCGGCAAAAACCTCTACACGTTCTGCGTGAGCTATGTGGATTCCATCCAGCAAATGAGG

Fig. 2-3

```
AACAAGTTTGCCTTCCGAGAGGCCATCAACAAACTGGAGAATAATCTCCGGGAGCTTCAGATCTGCCCGG  ⇦ ABL exon 11
CGACAGCAGGCAGTGGTCCAGCGGCCACTCAGGACTTCAGCAAGCTCCTCAGTTCGGTGAAGGAAATCAG
TGACATAGTGCAGAGGTAGCAGCAGTCAGGGGTCAGGTGTCAGGCCCGTCGGAGCTGCCTGCAGCACATG
CGGGCTCGCCCATACCCGTGACAGTGGCTGACAAGGGACTAGTGAGTCAGCACCTTGGCCCAGGAGCTCT
GCGCCAGGCAGAGCTGAGGGCCCTGTGGAGTCCAGCTCTACTACCTACGTTTGCACCGCCTGCCCTCCCG
CACCTTCCTCCTCCCCGCTCCGTCTCTGTCCTCGAATTTTATCTGTGGAGTTCCTGCTCCGTGGACTGCA
GTCGGCATGCCAGGACCCGCCAGCCCCGCTCCCACCTAGTGCCCCAGACTGAGCTCTCCAGGCCAGGTGG
GAACGGCTGATGTGGACTGTCTTTTTCATTTTTTTCTCTCTGGAGCCCCTGCTCCCCCGGCTGGGCCTCC
TTCTTCCACTTCTCCAAGAATGGAAGCCTGAACTGAGGCCTTGTGTGTCAGGCCCTCTGCCTGCACTCCC
TGGCCTTGCCCGTCGTGTGCTGAAGACATGTTTCAAGAACCGCATTTCGGGAAGGGCATGCACGGGCATG
CACACGGCTGGTCACTCTGCCCTCTGCTGCTGCCCGGGGTGGGGTGCACTCGCCATTTCCTCACGTGCAG
GACAGCTCTTGATTTGGGTGGAAAACAGGGTGCTAAAGCCAACCAGCCTTTGGGTCCTGGGCAGGTGGGA
GCTGAAAAGGATCGAGGCATGGGGCATGTCCTTTCCATCTGTCCACATCCCCAGAGCCCAGCTCTTGCTC
TCTTGTGACGTGCACTGTGAATCCTGGCAAGAAAGCTTGAGTCTCAAGGGTGGCAGGTCACTGTCACTGC
CGACATCCCTCCCCCAGCAGAATGGAGGCAGGGGACAAGGGAGGCAGTGGCTAGTGGGGTGAACAGCTGG
TGCCAAATAGCCCCAGACTGGGCCCAGGCAGGTCTGCAAGGGCCCAGAGTGAACCGTCCTTTCACACATC
TGGGTGCCCTGAAAGGGCCCTTCCCCTCCCCCACTCCTCTAAGACAAAGTAGATTCTTACAAGGCCCTTT
CCTTTGGAACAAGACAGCCTTCACTTTTCTGAGTTCTTGAAGCATTTCAAAGCCCTGCCTCTGTGTAGCC
GCCCTGAGAGAGAATAGAGCTGCCACTGGGCACCTGCGCACAGGTGGGAGGAAAGGGCCTGGCCAGTCCT
GGTCCTGGCTGCACTCTTGAACTGGGCGAATGTCTTATTTAATTACCGTGAGTGACATAGCCTCATGTTC
TGTGGGGGTCATCAGGGAGGGTTAGGAAAACCACAAACGGAGCCCCTGAAAGCCTCACGTATTTCACAGA
GCACGCCTGCCATCTTCTCCCCGAGGCTGCCCCAGGCCGGAGCCCAGATACGGGGGCTGTGACTCTGGGC
AGGGACCCGGGGTCTCCTGGACCTTGACAGAGCAGCTAACTCCGAGAGCAGTGGGCAGGTGGCCGCCCCT
GAGGCTTCACGCCGGGAGAAGCCACCTTCCCACCCCTTCATACCGCCTCGTGCCAGCAGCCTCGCACAGG
CCCTAGCTTTACGCTCATCACCTAAACTTGTACTTTATTTTTCTGATAGAAATGGTTTCCTCTGGATCGT
TTTATGCGGTTCTTACAGCACATCACCTCTTTGCCCCCGACGGCTGTGACGCAGCCGGAGGGAGGCACTA
GTCACCGACAGCGGCCTTGAAGACAGAGCAAAGCGCCCACCCAGGTCCCCCGACTGCCTGTCTCCATGAG
GTACTGGTCCCTTCCTTTTGTTAACGTGATGTGCCACTATATTTTACACGTATCTCTTGGTATGCATCTT
TTATAGACGCTCTTTTCTAAGTGGCGTGTGCATAGCGTCCTGCCCTGCCCCCTCGGGGGCCTGTGGTGGC
TCCCCCTCTGCTTCTCGGGGTCCAGTGCATTTTGTTTCTGTATATGATTCTCTGTGGTTTTTTTTGAATC
CAAATCTGTCCTCTGTAGTATTTTTTAAATAAATCAGTGTTTACATTAGAAAAAAAAAAAAAAAAAAAA
```

Fig. 3-1

```
GGGGGGAGGGTGGCGGCTCGATGGGGGAGCCGCCTCCAGGGGGCCCCCCGCCCTGTGCCCACGGCGCGG   ⇦ BCR exon 1
CCCCTTTAAGAGGCCCGCCTGGCTCCGTCATCCGCGCCGCGGCCACCTCCCCCGGCCCTCCCCTTCCTG
CGGCGCAGAGTGCGGGCCGGGCGGGAGTGCGGCGAGAGCCGGCTGGCTGAGCTTAGCGTCCGAGGAGGCG
GCGGCGGCGGCGGCGGCACGGCGGCGGCGGGGCTGTGGGGCGGTGCGGAAGCGAGAGGCGAGGAGCGCGC
GGGCCGTGGCCAGAGTCTGGCGGCGGCCTGGCGGAGCGGAGAGCAGCGCCCGCGCCTCGCCGTGCGGAGG
AGCCCCGCACACAATAGCGGCGCGCGCAGCCCGCGCCCTTCCCCCCGGCGCGCCCCGCCCCGCGCGCCGA
GCGCCCCGCTCCGCCTCACCTGCCACCAGGGAGTGGGCGGGCATTGTTCGCCGCCGCCGCCGCCGCGCGG
GCCATGGGGGCCGCCCGGCGCCCGGGGCCGGGCTGGCGAGGCGCCGCGCCGCCGCTGAGACGGGCCCCGC
GCGCAGCCCGGCGGCGCAGGTAAGGCCGGCCGCGCCATGGTGGACCCGGTGGGCTTCGCGGAGGCGTGGA
AGGCGCAGTTCCCGGACTCAGAGCCCCCGCGCATGGAGCTGCGCTCAGTGGGCGACATCGAGCAGGAGCT
GGAGCGCTGCAAGGCCTCCATTCGGCGCCTGGAGCAGGAGGTGAACCAGGAGCGCTTCCGCATGATCTAC
CTGCAGACGTTGCTGGCCAAGGAAAAGAAGAGCTATGACCGGCAGCGATGGGGCTTCCGGCGCGCGGCGC
AGGCCCCCGACGGCGCCTCCGAGCCCCGAGCGTCCGCGTCGCGCCCGCAGCCAGCGCCCGCCGACGGAGC
CGACCCGCCGCCCGCCGAGGAGCCCGAGGCCCGGCCCGACGGCGAGGGTTCTCCGGGTAAGGCCAGGCCC
GGGACCGCCCGCAGGCCCGGGGCAGCCGCGTCGGGGGAACGGGACGACCGGGGACCCCCCGCCAGCGTGG
CGGCGCTCAGGTCCAACTTCGAGCGGATCCGCAAGGGCCATGGCCAGCCCGGGGCGGACGCCGAGAAGCC
CTTCTACGTGAACGTCGAGTTTCACCACGAGCGCGGCCTGGTGAAGGTCAACGACAAAGAGGTGTCGGAC
CGCATCAGCTCCCTGGGCAGCCAGGCCATGCAGATGGAGCGCAAAAAGTCCCAGCACGGCGCGGGCTCGA
GCGTGGGGGATGCATCCAGGCCCCCTTACCGGGGACGCTCCTCGGAGAGCAGCTGCGGCGTCGACGGCGA
CTACGAGGACGCCGAGTTGAACCCCCGCTTCCTGAAGGACAACCTGATCGACGCCAATGGCGGTAGCAGG
CCCCCTTGGCCGCCCCTGGAGTACCAGCCCTACCAGAGCATCTACGTCGGGGGCATGATGGAAGGGGAGG
GCAAGGGCCCGCTCCTGCGCAGCCAGAGCACCTCTGAGCAGGAGAAGCGCCTTACCTGGCCCCGCAGGTC
CTACTCCCCCCGGAGTTTTGAGGATTGCGGAGGCGGCTATACCCCGGACTGCAGCTCCAATGAGAACCTC
ACCTCCAGCGAGGAGGACTTCTCCTCTGGCCAGTCCAGCCGCGTGTCCCCAAGCCCCACCACCTACCGCA
TGTTCCGGGACAAAAGCCGCTCTCCCTCGCAGAACTCGCAACAGTCCTTCGACAGCAGCAGTCCCCCCAC
GCCGCAGTGCCATAAGCGGCACCGGCACTGCCCGGTTGTCGTGTCCGAGGCCACCATCGTGGGCGTCCGC
AAGACCGGGCAGATCTGGCCCAACGATGGCGAGGGCGCCTTCCATGGAGACGCAG ATGGCTCGTTCGGA   ⇦ BCR exon 2
ACACCACCTGGATACGGCTGCGCTGCAGACCGGGCAGAGGAGCAGCGCCGGCACCAAGATGGGCTGCCCT
ACATTGATGACTCGCCCTCCTCATCGCCCCACCTCAGCAGCAAGGGCAGGGGCAGCCGGGATGCGCTGGT
CTCGGGAGCCCTGGAGTCCACTAAAGCG AGTGAGCTGGACTTGGAAAAGGGCTTGGAGATGAGAAAATG   ⇦ BCR exon 3
GGTCCTGTCGGGAATCCTGGCTAGCGAGGAGACTTACCTGAGCCACCTGGAGGCACTGCTGCTG CCCAT   ⇦ BCR exon 4
GAAGCCTTTGAAAGCCGCTGCCACCACCTCTCAGCCGGTGCTGACGAGTCAGCAGATCGAGACCATCTTC
TTCAAAGTGCCTGAGCTCTACGAGATCCACAAGGAGTTCTATGATGGGCTCTTCCCCCGCGTGCAGCAGT
GGAGCCACCAGCAGCGGGTGGGCGACCTCTTCCAGAAGCTG GCCAGCCAGCTGGGTGTGTACCGGGCCT   ⇦ BCR exon 5
TCGTGGACAACTACGGAGTTGCCATGGAAATGGCTGAGAAGTGCTGTCAGGCCAATGCTCAGTTTGCAGA
AATCTCCGAG AACCTGAGAGCCAGAAGCAACAAAGATGCCAAGGATCCAACGACCAAGAACTCTCTGGA   ⇦ BCR exon 6
```

Fig. 3-2

```
BCR exon 6      BCR exon 7
   ⇩               ⇩
AA CTCTGCTCTACAAGCCTGTGGACCGTGTGACGAGGAGCACGCTGGTCCTCCAT GACTTGCTGAAGC   ⇦ BCR exon 8
ACACTCCTGCCAGCCACCCTGACCACCCCTTGCTGCAGGACGCCCTCCGCATCTCACAGAACTTCCTGTC
CAGCATCAATGAGGAGATCACACCCCGACGGCAGTCCATGACGGTGAAGAAGGGAGAG CACCGGCAGCT   ⇦ BCR exon 9
GCTGAAGGACAGCTTCATGGTGGAGCTGGTGGAGGGGGCCCGCAAGCTGCGCCACGTCTTCCTGTTCACC
GACCTGCTTCTCTGCACCAAGCTCAAGAAGCAGAGCGGAGG CAAAACGCAGCAGTATGACTGCAAATGG   ⇦ BCR exon 10
TACATTCCGCTCACGGATCTCAGCTTCCAGATGGTGGATGAACTGGAGGCAGTGCCCAACATCCCCCTGG
TGCCCGATGAGGAGCTGGACGCTTTGAAGATCAAGATCTCCCAGATCAAGAATGACATCCAGAGAGAGAA
G AGGGCGAACAAGGGCAGCAAGGCTACGGAGAGGCTGAAGAAGAAGCTGTCGGAGCAGGAGTCACTGCT   ⇦ BCR exon 11
GCTGCTTATGTCTCCCAGCATGGCCTTCAGGGTGCACAGCCGCAACGGCAAG AGTTACACGTTCCTGAT   ⇦ BCR exon 12
CTCCTCTGACTATGAGCGTGCAGAGTGGAGGGAGAACATCCGGGAGCAGCAGAAGAAGT GTTTCAGAAG   ⇦ BCR exon 13
CTTCTCCCTGACATCCGTGGAGCTGCAGATGCTGACCAACTCGTGTGTGAAACTCCAGACTGTCCACAGC
ATTCCGCTGACCATCAATAAGGAAG AAGCCCTTCAGCGGCCAGTAGCATCTGACTTTGAGCCTCAGGGT   ⇦ ABL exon 2
CTGAGTGAAGCCGCTCGTTGGAACTCCAAGGAAAACCTTCTCGCTGGACCCAGTGAAAATGACCCCAACC
TTTTCGTTGCACTGTATGATTTTGTGGCCAGTGGAGATAACACTCTAAGCATAACTAAAG GTGAAAAGC   ⇦ ABL exon 3
TCCGGGTCTTAGGCTATAATCACAATGGGGAATGGTGTGAAGCCCAAACCAAAAATGGCCAAGGCTGGGT
CCCAAGCAACTACATCACGCCAGTCAACAGTCTGGAGAAACACTCCTGGTACCATGGGCCTGTGTCCCGC
AATGCCGCTGAGTATCTGCTGAGCAGCGGGATCAATGGCAGCTTCTTGGTGCGTGAGAGTGAGAGCAGTC
CTGGCCAGAGGTCCATCTCGCTGAGATACGAAGGGAGGGTGTACCATTACAGGATCAACACTGCTTCTGA
TGGCAAG CTCTACGTCTCCTCCGAGAGCCGCTTCAACACCCTGGCCGAGTTGGTTCATCATCATTCAAC   ⇦ ABL exon 4
GGTGGCCGACGGGCTCATCACCACGCTCCATTATCCAGCCCCAAAGCGCAACAAGCCCACTGTCTATGGT
GTGTCCCCCAACTACGACAAGTGGGAGATGGAACGCACGGACATCACCATGAAGCACAAGCTGGGCGGGG
GCCAGTACGGGGAGGTGTACGAGGGCGTGTGGAAGAAATACAGCCTGACGGTGGCCGTGAAGACCTTGAA
G GAGGACACCATGGAGGTGGAAGAGTTCTTGAAAGAAGCTGCAGTCATGAAAGAGATCAAACACCCTAA   ⇦ ABL exon 5
CCTGGTGCAGCTCCTTG GGGTCTGCACCCGGGAGCCCCCGTTCTATATCATCACTGAGTTCATGACCTA   ⇦ ABL exon 6
CGGGAACCTCCTGGACTACCTGAGGGAGTGCAACCGGCAGGAGGTGAACGCCGTGGTGCTGCTGTACATG
GCCACTCAGATCTCGTCAGCCATGGAGTACCTGGAGAAGAAAAACTTCATCCACAG AGATCTTGCTGCC   ⇦ ABL exon 7
CGAAACTGCCTGGTAGGGGAGAACCACTTGGTGAAGGTAGCTGATTTTGGCCTGAGCAGGTTGATGACAG
GGGACACCTACACAGCCCATGCTGGAGCCAAGTTCCCCATCAAATGGACTGCACCCGAGAGCCTGGCCTA
CAACAAGTTCTCCATCAAGTCCGACGTCTGGG CATTTGGAGTATTGCTTTGGGAAATTGCTACCTATGG   ⇦ ABL exon 8
CATGTCCCCTTACCCGGGAATTGACCTGTCCCAGGTGTATGAGCTGCTAGAGAAGGACTACCGCATGGAG
CGCCCAGAAGGCTGCCCAGAGAAGGTCTATGAACTCATGCGAGCAT GTTGGCAGTGGAATCCCTCTGAC   ⇦ ABL exon 9
CGGCCCTCCTTTGCTGAAATCCACCAAGCCTTTGAAACAATGTTCCAGGAATCCAGTATCTCAGACG AA   ⇦ ABL exon 10
GTGGAAAAGGAGCTGGGGAAACAAGGCGTCCGTGGGGCTGTGAGTACCTTGCTGCAGGCCCCAGAGCTGC
CCACCAAGACGAGGACCTCCAGGAGAGCTGCAGAGCACAGAGACACCACTGACGTGCCTGAGATGCCTCA
CTCCAAGGGCCAGGGAGAGAGCG ATCCTCTGGACCATGAGCCTGCCGTGTCTCCATTGCTCCCTCGAAA   ⇦ ABL exon 11
AGAGCGAGGTCCCCCGGAGGGCGGCCTGAATGAAGATGAGCGCCTTCTCCCCAAAGACAAAAAGACCAAC
```

Fig. 3-3

⇦ ABL exon 11

```
TTGTTCAGCGCCTTGATCAAGAAGAAGAAGAAGACAGCCCCAACCCCTCCCAAACGCAGCAGCTCCTTCC
GGGAGATGGACGGCCAGCCGGAGCGCAGAGGGGCCGGCGAGGAAGAGGGCCGAGACATCAGCAACGGGGC
ACTGGCTTTCACCCCCTTGGACACAGCTGACCCAGCCAAGTCCCCAAAGCCCAGCAATGGGGCTGGGGTC
CCCAATGGAGCCCTCCGGGAGTCCGGGGGCTCAGGCTTCCGGTCTCCCCACCTGTGGAAGAAGTCCAGCA
CGCTGACCAGCAGCCGCCTAGCCACCGGCGAGGAGGAGGGCGGTGGCAGCTCCAGCAAGCGCTTCCTGCG
CTCTTGCTCCGCCTCCTGCGTTCCCCATGGGGCCAAGGACACGGAGTGGAGGTCAGTCACGCTGCCTCGG
GACTTGCAGTCCACGGGAAGACAGTTTGACTCGTCCACATTTGGAGGGCACAAAAGTGAGAAGCCGGCTC
TGCCTCGGAAGAGGGCAGGGGAGAACAGGTCTGACCAGGTGACCCGAGGCACAGTAACGCCTCCCCCCAG
GCTGGTGAAAAAGAATGAGGAAGCTGCTGATGAGGTCTTCAAAGACATCATGGAGTCCAGCCCGGGCTCC
AGCCCGCCCAACCTGACTCCAAAACCCCTCCGGCGGCAGGTCACCGTGGCCCCTGCCTCGGGCCTCCCCC
ACAAGGAAGAAGCTGGAAAGGGCAGTGCCTTAGGGACCCCTGCTGCAGCTGAGCCAGTGACCCCCACCAG
CAAAGCAGGCTCAGGTGCACCAGGGGGCACCAGCAAGGGCCCCGCCGAGGAGTCCAGAGTGAGGAGGCAC
AAGCACTCCTCTGAGTCGCCAGGGAGGGACAAGGGGAAATTGTCCAGGCTCAAACCTGCCCCGCCGCCCC
CACCAGCAGCCTCTGCAGGGAAGGCTGGAGGAAAGCCCTCGCAGAGCCCGAGCCAGGAGGCGGCCGGGGA
GGCAGTCCTGGGCGCAAAGACAAAAGCCACGAGTCTGGTTGATGCTGTGAACAGTGACGCTGCCAAGCCC
AGCCAGCCGGGAGAGGGCCTCAAAAAGCCCGTGCTCCCGGCCACTCCAAAGCCACAGTCCGCCAAGCCGT
CGGGGACCCCCATCAGCCCAGCCCCCGTTCCCTCCACGTTGCCATCAGCATCCTCGGCCCTGGCAGGGGA
CCAGCCGTCTTCCACCGCCTTCATCCCTCTCATATCAACCCGAGTGTCTCTTCGGAAAACCCGCCAGCCT
CCAGAGCGGATCGCCAGCGGCGCCATCACCAAGGGCGTGGTCCTGGACAGCACCGAGGCGCTGTGCCTCG
CCATCTCTAGGAACTCCGAGCAGATGGCCAGCCACAGCGCAGTGCTGGAGGCCGGCAAAAACCTCTACAC
GTTCTGCGTGAGCTATGTGGATTCCATCCAGCAAATGAGGAACAAGTTTGCCTTCCGAGAGGCCATCAAC
AAACTGGAGAATAATCTCCGGGAGCTTCAGATCTGCCCGGCGACAGCAGGCAGTGGTCCAGCGGCCACTC
AGGACTTCAGCAAGCTCCTCAGTTCGGTGAAGGAAATCAGTGACATAGTGCAGAGGTAGCAGCAGTCAGG
GGTCAGGTGTCAGGCCCGTCGGAGCTGCCTGCAGCACATGCGGGCTCGCCCATACCCGTGACAGTGGCTG
ACAAGGGACTAGTGAGTCAGCACCTTGGCCCAGGAGCTCTGCGCCAGGCAGAGCTGAGGGCCCTGTGGAG
TCCAGCTCTACTACCTACGTTTGCACCGCCTGCCCTCCCGCACCTTCCTCCTCCCCGCTCCGTCTCTGTC
CTCGAATTTTATCTGTGGAGTTCCTGCTCCGTGGACTGCAGTCGGCATGCCAGGACCCGCCAGCCCCGCT
CCCACCTAGTGCCCCAGACTGAGCTCTCCAGGCCAGGTGGGAACGGCTGATGTGGACTGTCTTTTTCATT
TTTTTCTCTCTGGAGCCCCTCCTCCCCCGGCTGGGCCTCCTTCTTCCACTTCTCCAAGAATGGAAGCCTG
AACTGAGGCCTTGTGTGTCAGGCCCTCTGCCTGCACTCCCTGGCCTTGCCCGTCGTGTGCTGAAGACATG
TTTCAAGAACCGCATTTCGGGAAGGGCATGCACGGGCATGCACACGGCTGGTCACTCTGCCCTCTGCTGC
TGCCCGGGGTGGGGTGCACTCGCCATTTCCTCACGTGCAGGACAGCTCTTGATTTGGGTGGAAAACAGGG
TGCTAAAGCCAACCAGCCTTTGGGTCCTGGGCAGGTGGGAGCTGAAAAGGATCGAGGCATGGGGCATGTC
CTTTCCATCTGTCCACATCCCCAGAGCCCAGCTCTTGCTCTCTTGTGACGTGCACTGTGAATCCTGGCAA
GAAAGCTTGAGTCTCAAGGGTGGCAGGTCACTGTCACTGCCGACATCCCTCCCCCAGCAGAATGGAGGCA
GGGGACAAGGGAGGCAGTGGCTAGTGGGGTGAACAGCTGGTGCCAAATAGCCCCAGACTGGGCCCAGGCA
```

Fig. 3-4

```
GGTCTGCAAGGGCCCAGAGTGAACCGTCCTTTCACACATCTGGGTGCCCTGAAAGGGCCCTTCCCCTCCC
CCACTCCTCTAAGACAAAGTAGATTCTTACAAGGCCCTTTCCTTTGGAACAAGACAGCCTTCACTTTTCT
GAGTTCTTGAAGCATTTCAAAGCCCTGCCTCTGTGTAGCCGCCCTGAGAGAGAATAGAGCTGCCACTGGG
CACCTGCGCACAGGTGGGAGGAAAGGGCCTGGCCAGTCCTGGTCCTGGCTGCACTCTTGAACTGGGCGAA
TGTCTTATTTAATTACCGTGAGTGACATAGCCTCATGTTCTGTGGGGGTCATCAGGGAGGGTTAGGAAAA
CCACAAACGGAGCCCCTGAAAGCCTCACGTATTTCACAGAGCACGCCTGCCATCTTCTCCCCGAGGCTGC
CCCAGGCCGGAGCCGAGATACGGGGGCTGTGACTCTGGGCAGGGACCCGGGGTCTCCTGGACCTTGACAG
AGCAGCTAACTCCGAGAGCAGTGGGCAGGTGGCCGCCCCTGAGGCTTCACGCCGGGAGAAGCCACCTTCC
CACCCCTTCATACCGCCTCGTGCCAGCAGCCTCGCACAGGCCCTAGCTTTACGCTCATCACCTAAACTTG
TACTTTATTTTTCTGATAGAAATGGTTTCCTCTGGATCGTTTTATGCGGTTCTTACAGCACATCACCTCT
TTGCCCCCGACGGCTGTGACGCAGCCGGAGGGAGGCACTAGTCACCGACAGCGGCCTTGAAGACAGAGCA
AAGCGCCCACCCAGGTCCCCCGACTGCCTGTCTCCATGAGGTACTGGTCCCTTCCTTTTGTTAACGTGAT
GTGCCACTATATTTTACACGTATCTCTTGGTATGCATCTTTTATAGACGCTCTTTTCTAAGTGGCGTGTG
CATAGCGTCCTGCCCTGCCCCCTCGGGGGCCTGTGGTGGCTCCCCCTCTGCTTCTCGGGGTCCAGTGCAT
TTTGTTTCTGTATATGATTCTCTGTGGTTTTTTTTGAATCCAAATCTGTCCTCTGTAGTATTTTTTAAAT
AAATCAGTGTTTACATTAGAAAAAAAAAAAAAAAAAAAAA
```

⇦ ABL exon 11

Fig. 4-1

```
GGGGGGAGGGTGGCGGCTCGATGGGGGAGCCGCCTCCAGGGGGCCCCCCGCCCTGTGCCCACGGCGCGG   <= BCR exon 1
CCCCTTTAAGAGGCCCGCCTGGCTCCGTCATCCGCGCCGCGGCCACCTCCCCCGGCCCTCCCCTTCCTG
CGGCGCAGAGTGCGGGCCGGGCGGGAGTGCGGCGAGAGCCGGCTGGCTGAGCTTAGCGTCCGAGGAGGCG
GCGGCGGCGGCGGCGGCACGGCGGCGGCGGGGCTGTGGGGCGGTGCGGAAGCGAGAGGCGAGGAGCGCGC
GGGCCGTGGCCAGAGTCTGGCGGCGGCCTGGCGGAGCGGAGAGCAGCGCCCGCGCCTCGCCGTGCGGAGG
AGCCCCGCACACAATAGCGGCGCGCGCAGCCCGCGCCCTTCCCCCCGGCGCGCCCCGCCCCGCGCGCCGA
GCGCCCCGCTCCGCCTCACCTGCCACCAGGGAGTGGGCGGGCATTGTTCGCCGCCGCCGCCGCCGCGCGG
GCCATGGGGGCCGCCCGGCGCCCGGGGCCGGGCTGGCGAGGCGCCGCGCCGCCGCTGAGACGGGCCCCGC
GCGCAGCCCGGCGGCGCAGGTAAGGCCGGCCGCGCCATGGTGGACCCGGTGGGCTTCGCGGAGGCGTGGA
AGGCGCAGTTCCCGGACTCAGAGCCCCCGCGCATGGAGCTGCGCTCAGTGGGCGACATCGAGCAGGAGCT
GGAGCGCTGCAAGGCCTCCATTCGGCGCCTGGAGCAGGAGGTGAACCAGGAGCGCTTCCGCATGATCTAC
CTGCAGACGTTGCTGGCCAAGGAAAAGAAGAGCTATGACCGGCAGCGATGGGGCTTCCGGCGCGCGGCGC
AGGCCCCCGACGGCGCCTCCGAGCCCCGAGCGTCCGCGTCGCGCCCGCAGCCAGCGCCCGCCGACGGAGC
CGACCCGCCGCCCGCCGAGGAGCCCGAGGCCCGGCCCGACGGCGAGGGTTCTCCGGGTAAGGCCAGGCCC
GGGACCGCCCGCAGGCCCGGGGCAGCCGCGTCGGGGGAACGGGACGACCGGGGACCCCCCGCCAGCGTGG
CGGCGCTCAGGTCCAACTTCGAGCGGATCCGCAAGGGCCATGGCCAGCCCGGGGCGGACGCCGAGAAGCC
CTTCTACGTGAACGTCGAGTTTCACCACGAGCGCGGCCTGGTGAAGGTCAACGACAAAGAGGTGTCGGAC
CGCATCAGCTCCCTGGGCAGCCAGGCCATGCAGATGGAGCGCAAAAAGTCCCAGCACGGCGCGGGCTCGA
GCGTGGGGGATGCATCCAGGCCCCCTTACCGGGGACGCTCCTCGGAGAGCAGCTGCGGCGTCGACGGCGA
CTACGAGGACGCCGAGTTGAACCCCCGCTTCCTGAAGGACAACCTGATCGACGCCAATGGCGGTAGCAGG
CCCCCTTGGCCGCCCCTGGAGTACCAGCCCTACCAGAGCATCTACGTCGGGGGCATGATGGAAGGGGAGG
GCAAGGGCCCGCTCCTGCGCAGCCAGAGCACCTCTGAGCAGGAGAAGCGCCTTACCTGGCCCCGCAGGTC
CTACTCCCCCCGGAGTTTTGAGGATTGCGGAGGCGGCTATACCCCGGACTGCAGCTCCAATGAGAACCTC
ACCTCCAGCGAGGAGGACTTCTCCTCTGGCCAGTCCAGCCGCGTGTCCCCAAGCCCCACCACCTACCGCA
TGTTCCGGGACAAAAGCCGCTCTCCCTCGCAGAACTCGCAACAGTCCTTCGACAGCAGCAGTCCCCCCAC
GCCGCAGTGCCATAAGCGGCACCGGCACTGCCCGGTTGTCGTGTCCGAGGCCACCATCGTGGGCGTCCGC
AAGACCGGGCAGATCTGGCCCAACGATGGCGAGGGCGCCTTCCATGGAGACGCAG ATGGCTCGTTCGGA   <= BCR exon 2
ACACCACCTGGATACGGCTGCGCTGCAGACCGGGCAGAGGAGCAGCGCCGGCACCAAGATGGGCTGCCCT
ACATTGATGACTCGCCCTCCTCATCGCCCCACCTCAGCAGCAAGGGCAGGGGCAGCCGGGATGCGCTGGT
CTCGGGAGCCCTGGAGTCCACTAAAGCG AGTGAGCTGGACTTGGAAAAGGGCTTGGAGATGAGAAAATG   <= BCR exon 3
GGTCCTGTCGGGAATCCTGGCTAGCGAGGAGACTTACCTGAGCCACCTGGAGGCACTGCTGCTG CCCAT   <= BCR exon 4
GAAGCCTTTGAAAGCCGCTGCCACCACCTCTCAGCCGGTGCTGACGAGTCAGCAGATCGAGACCATCTTC
TTCAAAGTGCCTGAGCTCTACGAGATCCACAAGGAGTTCTATGATGGGCTCTTCCCCCGCGTGCAGCAGT
GGAGCCACCAGCAGCGGGTGGGCGACCTCTTCCAGAAGCTG GCCAGCCAGCTGGGTGTGTACCGGGCCT   <= BCR exon 5
TCGTGGACAACTACGGAGTTGCCATGGAAATGGCTGAGAAGTGCTGTCAGGCCAATGCTCAGTTTGCAGA
AATCTCCGAG AACCTGAGAGCCAGAAGCAACAAAGATGCCAAGGATCCAACGACCAAGAACTCTCTGGA   <= BCR exon 6
```

Fig 4-2

BCR exon 6 ⇩ BCR exon 7 ⇩

AA CTCTGCTCTACAAGCCTGTGGACCGTGTGACGAGGAGCACGCTGGTCCTCCAT GACTTGCTGAAGC ⇦ BCR exon 8
ACACTCCTGCCAGCCACCCTGACCACCCCTTGCTGCAGGACGCCCTCCGCATCTCACAGAACTTCCTGTC
CAGCATCAATGAGGAGATCACACCCCGACGGCAGTCCATGACGGTGAAGAAGGGAGAG CACCGGCAGCT ⇦ BCR exon 9
GCTGAAGGACAGCTTCATGGTGGAGCTGGTGGAGGGGGCCCGCAAGCTGCGCCACGTCTTCCTGTTCACC
GACCTGCTTCTCTGCACCAAGCTCAAGAAGCAGAGCGGAGG CAAAACGCAGCAGTATGACTGCAAATGG ⇦ BCR exon 10
TACATTCCGCTCACGGATCTCAGCTTCCAGATGGTGGATGAACTGGAGGCAGTGCCCAACATCCCCCTGG
TGCCCGATGAGGAGCTGGACGCTTTGAAGATCAAGATCTCCCAGATCAAGAATGACATCCAGAGAGAGAA
G AGGGCGAACAAGGGCAGCAAGGCTACGGAGAGGCTGAAGAAGAAGCTGTCGGAGCAGGAGTCACTGCT ⇦ BCR exon 11
GCTGCTTATGTCTCCCAGCATGGCCTTCAGGGTGCACAGCCGCAACGGCAAG AGTTACACGTTCCTGAT ⇦ BCR exon 12
CTCCTCTGACTATGAGCGTGCAGAGTGGAGGGAGAACATCCGGGAGCAGCAGAAGAAGT GTTTCAGAAG ⇦ BCR exon 13
CTTCTCCCTGACATCCGTGGAGCTGCAGATGCTGACCAACTCGTGTGTGAAACTCCAGACTGTCCACAGC
ATTCCGCTGACCATCAATAAGGAAG ATGATGAGTCTCCGGGGCTCTATGGGTTTCTGAATGTCATCGTC ⇦ BCR exon 14
CACTCAGCCACTGGATTTAAGCAGAGTTCAA AAGCCCTTCAGCGGCCAGTAGCATCTGACTTTGAGCCT ⇦ ABL exon 2
CAGGGTCTGAGTGAAGCCGCTCGTTGGAACTCCAAGGAAAACCTTCTCGCTGGACCCAGTGAAAATGACC
CCAACCTTTTCGTTGCACTGTATGATTTTGTGGCCAGTGGAGATAACACTCTAAGCATAACTAAAG GTG ⇦ ABL exon 3
AAAAGCTCCGGGTCTTAGGCTATAATCACAATGGGGAATGGTGTGAAGCCCAAACCAAAAATGGCCAAGG
CTGGGTCCCAAGCAACTACATCACGCCAGTCAACAGTCTGGAGAAACACTCCTGGTACCATGGGCCTGTG
TCCCGCAATGCCGCTGAGTATCTGCTGAGCAGCGGGATCAATGGCAGCTTCTTGGTGCGTGAGAGTGAGA
GCAGTCCTGGCCAGAGGTCCATCTCGCTGAGATACGAAGGGAGGGTGTACCATTACAGGATCAACACTGC
TTCTGATGGCAAG CTCTACGTCTCCTCCGAGAGCCGCTTCAACACCCTGGCCGAGTTGGTTCATCATCA ⇦ ABL exon 4
TTCAACGGTGGCCGACGGGCTCATCACCACGCTCCATTATCCAGCCCCAAAGCGCAACAAGCCCACTGTC
TATGGTGTGTCCCCCAACTACGACAAGTGGGAGATGGAACGCACGGACATCACCATGAAGCACAAGCTGG
GCGGGGGCCAGTACGGGGAGGTGTACGAGGGCGTGTGGAAGAAATACAGCCTGACGGTGGCCGTGAAGAC
CTTGAAG GAGGACACCATGGAGGTGGAAGAGTTCTTGAAAGAAGCTGCAGTCATGAAAGAGATCAAACA ⇦ ABL exon 5
CCCTAACCTGGTGCAGCTCCTTG GGGTCTGCACCCGGGAGCCCCCGTTCTATATCATCACTGAGTTCAT ⇦ ABL exon 6
GACCTACGGGAACCTCCTGGACTACCTGAGGGAGTGCAACCGGCAGGAGGTGAACGCCGTGGTGCTGCTG
TACATGGCCACTCAGATCTCGTCAGCCATGGAGTACCTGGAGAAGAAAAACTTCATCCACAG AGATCTT ⇦ ABL exon 7
GCTGCCCGAAACTGCCTGGTAGGGGAGAACCACTTGGTGAAGGTAGCTGATTTTGGCCTGAGCAGGTTGA
TGACAGGGGACACCTACACAGCCCATGCTGGAGCCAAGTTCCCCATCAAATGGACTGCACCCGAGAGCCT
GGCCTACAACAAGTTCTCCATCAAGTCCGACGTCTGGG CATTTGGAGTATTGCTTTGGGAAATTGCTAC ⇦ ABL exon 8
CTATGGCATGTCCCCTTACCCGGGAATTGACCTGTCCCAGGTGTATGAGCTGCTAGAGAAGGACTACCGC
ATGGAGCGCCCAGAAGGCTGCCCAGAGAAGGTCTATGAACTCATGCGAGCAT GTTGGCAGTGGAATCCC ⇦ ABL exon 9
TCTGACCGGCCCTCCTTTGCTGAAATCCACCAAGCCTTTGAAACAATGTTCCAGGAATCCAGTATCTCAG
ACG AAGTGGAAAAGGAGCTGGGGAAACAAGGCGTCCGTGGGGCTGTGAGTACCTTGCTGCAGGCCCCAG ⇦ ABL exon 10
AGCTGCCCACCAAGACGAGGACCTCCAGGAGAGCTGCAGAGCACAGAGACACCACTGACGTGCCTGAGAT
GCCTCACTCCAAGGGCCAGGGAGAGAGCG ATCCTCTGGACCATGAGCCTGCCGTGTCTCCATTGCTCCC ⇦ ABL exon 11

Fig. 4-3

```
TCGAAAAGAGCGAGGTCCCCGGAGGGCGGCCTGAATGAAGATGAGCGCCTTCTCCCCAAAGACAAAAAG   <- ABL exon 11
ACCAACTTGTTCAGCGCCTTGATCAAGAAGAAGAAGACAGCCCCAACCCCTCCCAAACGCAGCAGCT
CCTTCCGGGAGATGGACGGCCAGCCGGAGCGCAGAGGGGCCGGCGAGGAAGAGGGCCGAGACATCAGCAA
CGGGGCACTGGCTTTCACCCCCTTGGACACAGCTGACCCAGCCAAGTCCCCAAAGCCCAGCAATGGGGCT
GGGGTCCCCAATGGAGCCCTCCGGGAGTCCGGGGGCTCAGGCTTCCGGTCTCCCCACCTGTGGAAGAAGT
CCAGCACGCTGACCAGCAGCCGCCTAGCCACCGGCGAGGAGGAGGGCGGTGGCAGCTCCAGCAAGCGCTT
CCTGCGCTCTTGCTCCGCCTCCTGCGTTCCCCATGGGGCCAAGGACACGGAGTGGAGGTCAGTCACGCTG
CCTCGGGACTTGCAGTCCACGGGAAGACAGTTTGACTCGTCCAGATTTGGAGGGCACAAAAGTGAGAAGC
CGGCTCTGCCTCGGAAGAGGGCAGGGGAGAACAGGTCTGACCAGGTGACCCGAGGCACAGTAACGCCTCC
CCCCAGGCTGGTGAAAAAGAATGAGGAAGCTGCTGATGAGGTCTTCAAAGACATCATGGAGTCCAGCCCG
GGCTCCAGCCCGCCCAACCTGACTCCAAAACCCCTCCGGCGGCAGGTCACCGTGGCCCCTGCCTCGGGCC
TCCCCCACAAGGAAGAAGCTGGAAAGGGCAGTGCCTTAGGGACCCCTGCTGCAGCTGAGCCAGTGACCCC
CACCAGCAAAGCAGGCTCAGGTGCACCAGGGGGCACCAGCAAGGGCCCCGCCGAGGAGTCCAGAGTGAGG
AGGCACAAGCACTCCTCTGAGTCGCCAGGGAGGGACAAGGGGAAATTGTCCAGGCTCAAACCTGCCCCGC
CGCCCCCACCAGCAGCCTCTGCAGGGAAGGCTGGAGGAAAGCCCTCGCAGAGCCCGAGCCAGGAGGCGGC
CGGGGAGGCAGTCCTGGGCGCAAAGACAAAAGCCACGAGTCTGGTTGATGCTGTGAACAGTGACGCTGCC
AAGCCCAGCCAGCCGGGAGAGGGCCTCAAAAAGCCCGTGCTCCCGGCCACTCCAAAGCCACAGTCCGCCA
AGCCGTCGGGGACCCCCATCAGCCCAGCCCCCGTTCCCTCCACGTTGCCATCAGCATCCTCGGCCCTGGC
AGGGGACCAGCCGTCTTCCACCGCCTTCATCCCTCTCATATCAACCCGAGTGTCTCTTCGGAAAACCCGC
CAGCCTCCAGAGCGGATCGCCAGCGGCGCCATCACCAAGGGCGTGGTCCTGGACAGCACCGAGGCGCTGT
GCCTCGCCATCTCTAGGAACTCCGAGCAGATGGCCAGCCACAGCGCAGTGCTGGAGGCCGGCAAAAACCT
CTACACGTTCTGCGTGAGCTATGTGGATTCCATCCAGCAAATGAGGAACAAGTTTGCCTTCCGAGAGGCC
ATCAACAAACTGGAGAATAATCTCCGGGAGCTTCAGATCTGCCCGGCGACAGCAGGCAGTGGTCCAGCGG
CCACTCAGGACTTCAGCAAGCTCCTCAGTTCGGTGAAGGAAATCAGTGACATAGTGCAGAGGTAGCAGCA
GTCAGGGGTCAGGTGTCAGGCCCGTCGGAGCTGCCTGCAGCACATGCGGGCTCGCCCATACCCGTGACAG
TGGCTGACAAGGGACTAGTGAGTCAGCACCTTGGCCCAGGAGCTCTGCGCCAGGCAGAGCTGAGGGCCCT
GTGGAGTCCAGCTCTACTACCTACGTTTGCACCGCCTGCCCTCCCGCACCTTCCTCCTCCCCGCTCCGTC
TCTGTCCTCGAATTTTATCTGTGGAGTTCCTGCTCCGTGGACTGCAGTCGGCATGCCAGGACCCGCCAGC
CCCGCTCCCACCTAGTGCCCCAGACTGAGCTCTCCAGGCCAGGTGGGAACGGCTGATGTGGACTGTCTTT
TTCATTTTTTTCTCTCTGGAGCCCCTCCTCCCCCGGCTGGGCCTCCTTCTTCCACTTCTCCAAGAATGGA
AGCCTGAACTGAGGCCTTGTGTGTCAGGCCCTCTGCCTGCACTCCCTGGCCTTGCCCGTCGTGTGCTGAA
GACATGTTTCAAGAACCGCATTTCGGGAAGGGCATGCACGGGCATGCACACGGCTGGTCACTCTGCCCTC
TGCTGCTGCCCGGGGTGGGGTGCACTCGCCATTTCCTCACGTGCAGGACAGCTCTTGATTTGGGTGGAAA
ACAGGGTGCTAAAGCCAACCAGCCTTTGGGTCCTGGGCAGGTGGGAGCTGAAAAGGATCGAGGCATGGGG
CATGTCCTTTCCATCTGTCCACATCCCCAGAGCCCAGCTCTTGCTCTCTTGTGACGTGCACTGTGAATCC
TGGCAAGAAAGCTTGAGTCTCAAGGGTGGCAGGTCACTGTCACTGCCGACATCCCTCCCCCAGCAGAATG
```

Fig 4-4

⇦ ABL exon 11

```
GAGGCAGGGGACAAGGGAGGCAGTGGCTAGTGGGGTGAACAGCTGGTGCCAAATAGCCCCAGACTGGGCC
CAGGCAGGTCTGCAAGGGCCCAGAGTGAACCGTCCTTTCACACATCTGGGTGCCCTGAAAGGGCCCTTCC
CCTCCCCCACTCCTCTAAGACAAAGTAGATTCTTACAAGGCCCTTTCCTTTGGAACAAGACAGCCTTCAC
TTTTCTGAGTTCTTGAAGCATTTCAAAGCCCTGCCTCTGTGTAGCCGCCCTGAGAGAGAATAGAGCTGCC
ACTGGGCACCTGCGCACAGGTGGGAGGAAAGGGCCTGGCCAGTCCTGGTCCTGGCTGCACTCTTGAACTG
GGCGAATGTCTTATTTAATTACCGTGAGTGACATAGCCTCATGTTCTGTGGGGGTCATCAGGGAGGGTTA
GGAAAACCACAAACGGAGCCCCTGAAAGCCTCACGTATTTCACAGAGCACGCCTGCCATCTTCTCCCCGA
GGCTGCCCCAGGCCGGAGCCCAGATACGGGGGCTGTGACTCTGGGCAGGGACCCGGGGTCTCCTGGACCT
TGACAGAGCAGCTAACTCCGAGAGCAGTGGGCAGGTGGCCGCCCCTGAGGCTTCACGCCGGGAGAAGCCA
CCTTCCCACCCCTTCATACCGCCTCGTGCCAGCAGCCTCGCACAGGCCCTAGCTTTACGCTCATCACCTA
AACTTGTACTTTATTTTTCTGATAGAAATGGTTTCCTCTGGATCGTTTTATGCGGTTCTTACAGCACATC
ACCTCTTTGCCCCCGACGGCTGTGACGCAGCCGGAGGGAGGCACTAGTCACCGACAGCGGCCTTGAAGAC
AGAGCAAAGCGCCCACCCAGGTCCCCCGACTGCCTGTCTCCATGAGGTACTGGTCCCTTCCTTTTGTTAA
CGTGATGTGCCACTATATTTTACACGTATCTCTTGGTATGCATCTTTTATAGACGCTCTTTTCTAAGTGG
CGTGTGCATAGCGTCCTGCCCTGCCCCCTCGGGGGCCTGTGGTGGCTCCCCCTCTGCTTCTCGGGGTCCA
GTGCATTTTGTTTCTGTATATGATTCTCTGTGGTTTTTTTTGAATCCAAATCTGTCCTCTGTAGTATTTT
TTAAATAAATCAGTGTTTACATTAGAAAAAAAAAAAAAAAAAAAA
```

METHOD OF DETECTING MINOR BCR-ABL1 GENE

TECHNICAL FIELD

This application is a National Stage of International Application No. PCT/JP2018/016749 filed Apr. 25, 2018, claiming priority of Japanese Patent Application No. 2017-087666, the entire contents of which are incorporated herein by reference.

The disclosure relates to a method of detecting the minor BCR-ABL1 gene in a subject and a kit therefor.

BACKGROUND

The BCR-ABL1 fusion gene is a chromosomal abnormality found in the patients of chronic myelogenous leukemia (CML) and Philadelphia chromosome-positive acute lymphocytic leukemia (Ph+ALL). The chromosomal translocation of chromosome 9 and chromosome 22, which is designated as t(9;22), causes the fusion of the c-ABL1 gene on chromosome 9 (band region q34) and the bcr gene on chromosome 22 (band region q11). The fusion gene encodes the chimeric BCR-ABL1 protein. The BCR-ABL1 protein has a tyrosine kinase activity and causes unlimited proliferation of hematopoietic stem cells by constitutively stimulating cell proliferation signals and suppressing apoptosis. Recently developed tyrosine kinase inhibitors targeting the BCR-ABL1 protein, e.g., imatinib, have been improved the therapeutic outcome of CML and Ph+ALL.

The BCR-ABL1 is mainly classified into Major BCR-ABL1 (M-BCR-ABL1) and minor BCR-ABL1 (m-BCR-ABL1) according to the position where the BCR is cut. The M-BCR is found in about 95% of the CML patients, and the m-BCR is found in about 20 to 30% of the Ph+ALL patients. The expression level of each BCR-ABL1 gene can be the indicator for assisting the diagnosis of CML and Ph+ALL or monitoring the therapeutic effects. A kit for determining the expression level of the M-BCR-ABL1 is marketed by the applicant, under the tradename of "Major BCR-ABL1 mRNA assay." The kit determines the expression level of the M-BCR-ABL1 by a one-step quantitative real-time RT-PCR. Non-Patent Literature 1 discloses a method of determining the expression level of the m-BCR-ABL1.

REFERENCES

Patent Literature

[Patent Literature 1] U.S. Pat. No. 6,391,592

Non-Patent Literature

[Non-Patent Literature 1] Gabert J et al. Leukemia. 2003; 17: 2318-2357

SUMMARY

An object of the disclosure is to provide a method that detects the minor BCR-ABL1 gene more precisely than conventional methods.

An aspect of the disclosure provides a method of detecting the minor BCR-ABL1 gene in a subject comprising:

(1) conducting a PCR using a nucleic acid sample obtained from the subject as the template, a forward primer having a nucleic acid sequence of a part of exon 1 of the BCR gene, and a reverse primer having a nucleic acid sequence complementary to a part of exons 2 to 11 of the ABL1 gene, in the presence of a modified nucleic acid having a nucleic acid sequence of a part of exons 2 to 14 of the BCR gene or a nucleic acid sequence complementary thereto; and (2) determining that the subject has the minor BCR-ABL1 gene when the nucleic acid amplification is occurred in the PCR.

An aspect of the disclosure provides a kit for detecting the minor BCR-ABL1 gene in a subject comprising a modified nucleic acid having a nucleic acid sequence complementary to a part of exons 2 to 14 of the BCR gene, a reverse primer having a nucleic acid sequence complementary to a part of exons 2 to 11 of the ABL1 gene, and a forward primer having a nucleic acid sequence of a part of exon 1 of the BCR gene.

According to the disclosure, the minor BCR-ABL1 gene in a subject can be detected more precisely than conventional methods. This may give information useful for diagnosing or treating CML or Ph+ALL of the subject.

BRIEF DESCRIPTION OF DRAWINGS

FIG. 1 shows the structures of the m-BCR gene and the M-BCR gene, as well as a schematic drawing of the method described herein.

FIG. 2-1 shows the nucleic acid sequence of SEQ ID NO: 1.

FIG. 2-2 shows the nucleic acid sequence of SEQ ID NO: 1 (continued).

FIG. 2-3 shows the nucleic acid sequence of SEQ ID NO: 1 (continued).

FIG. 3-1 shows the nucleic acid sequence of SEQ ID NO: 2.

FIG. 3-2 shows the nucleic acid sequence of SEQ ID NO: 2 (continued).

FIG. 3-3 shows the nucleic acid sequence of SEQ ID NO: 2 (continued).

FIG. 3-4 shows the nucleic acid sequence of SEQ ID NO: 2 (continued).

FIG. 4-1 shows the nucleic acid sequence of SEQ ID NO: 3.

FIG. 4-2 shows the nucleic acid sequence of SEQ ID NO: 3 (continued).

FIG. 4-3 shows the nucleic acid sequence of SEQ ID NO: 3 (continued).

FIG. 4-4 shows the nucleic acid sequence of SEQ ID NO: 3 (continued).

DETAILED DESCRIPTION

Figure 5:
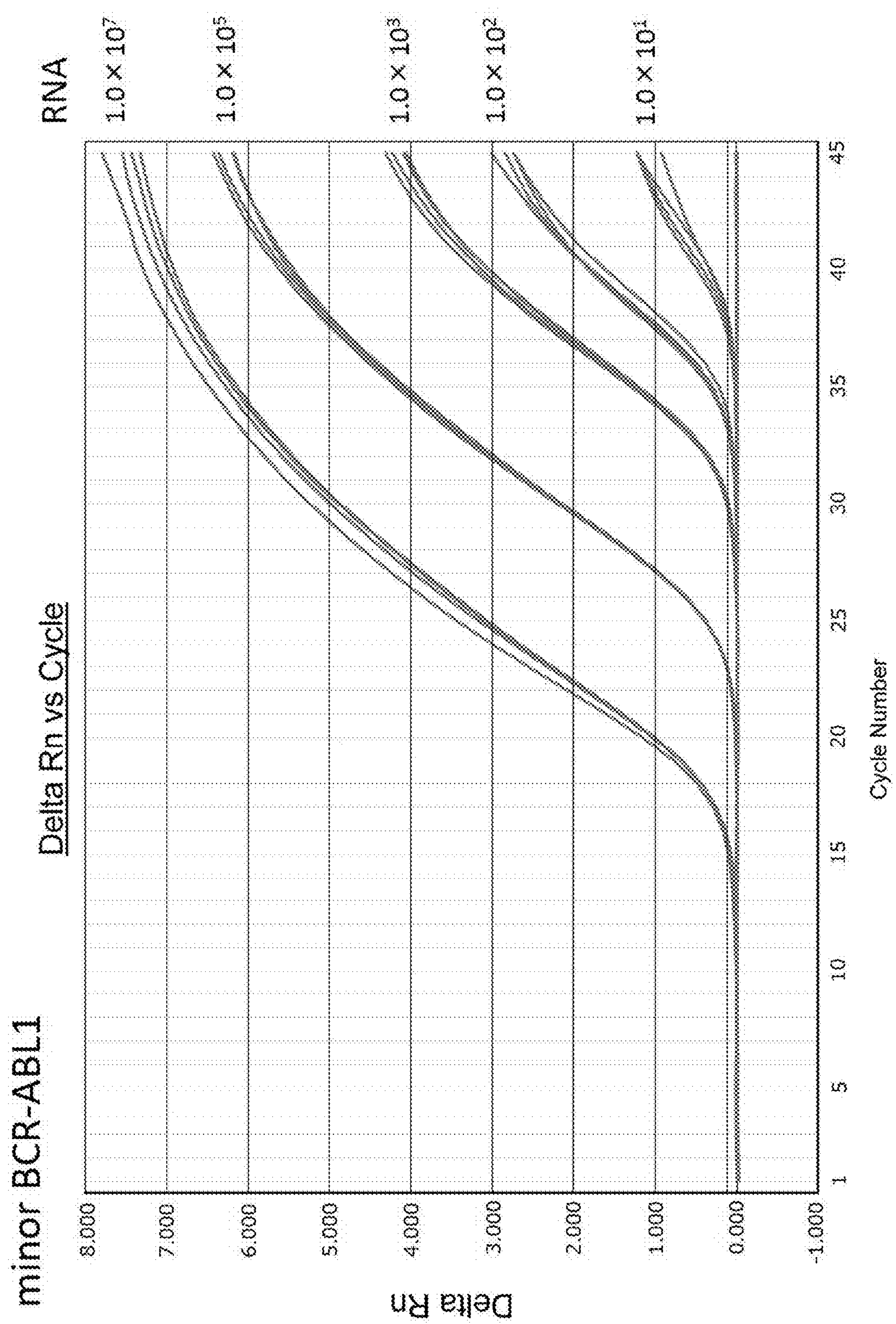
FIG. 5 shows the amplification curves of the minor BCR-ABL1 mRNA in the presence of PNA in the RT-PCR in Test 1.

Unless otherwise defined, the terms used herein are read as generally understood by a skilled person in the technical fields such as organic chemistry, medicine, pharmacology, molecular biology, and microbiology. Several terms used herein are defined as described below. The definitions herein take precedence over the general understanding.

When a numerical value is accompanied with the term "about", the value is intended to represent any value within the range of ±10% of that value. For example, "about 20" means "a value from 18 to 22." A range defined with a value of the lower limit and a value of the upper limit covers all values from the lower limit to the upper limit, including the values of the both limits. When a range is accompanied with the term "about", the both limits are read as accompanied with the term. For example, "about 20 to 30" is read as "18 to 33."

The BCR-ABL1 gene is a fusion gene of the ABL1 gene and the BCR gene, which is found in the patients of chronic myelogenous leukemia and Philadelphia chromosome-positive acute lymphocytic leukemia. The chromosomal translocation of chromosome 9 and chromosome 22, which is designated as t(9;22), creates the fusion gene.

The BCR-ABL1 gene is classified mainly into the minor-type and the Major-type according to the position where the BCR is cut. The former "minor BCR-ABL1 (m-BCR-ABL1) gene" is the fusion gene of exon 1 of the BCR gene and exons 2 to 11 of the ABL1 gene. The latter "Major BCR-ABL1 (M-BCR-ABL1) gene" is the fusion gene of exons 1 to 13 or exons 1 to 14 of the BCR gene and exons 2 to 11 of the ABL1 gene. The structures of the m-BCR-ABL1 gene and the M-BCR-ABL1 gene are shown in FIG. 1.

In the course of the development of the disclosed method, the inventors tested a known method that can be conducted with an existing kit for determining the m-BCR-ABL1 mRNA level and found that the known method sometimes does not precisely determine the level. The known method detected not only the m-BCR-ABL1 mRNA, but also the M-BCR-ABL1 mRNA (see Test 2 in the Examples below).

In the test a PCR was conducted to amplify the m-BCR-ABL1 cDNA with a forward primer designed on the basis of the nucleic acid sequence of exon 1 of the BCR gene and a reverse primer designed on the basis of the nucleic acid sequence of exon 2 of the ABL1 gene. It have been believed that the PCR under the conditions for amplifying the m-BCR-ABL1 cDNA cannot amplify the M-BCR-ABL1 cDNA, which has exons 2 to 13 (about 1428 bp) or exons 2 to 14 (about 1503 bp) of the BCR gene between exon 1 of the BCR gene and exon 2 of the ABL1 gene as shown in FIG. 1 and thus is much longer than the m-BCR-ABL1 cDNA.

However, as proved in Test 2, actually the known method can amplify the M-BCR-ABL1 cDNA. This is a severe defect that may lead a false detection or determination. The method and kit provided by the disclosure overcome the defect, achieving the precise detection of the m-BCR-ABL1 gene or its expression or the precise determination of the expression level of the m-BCR-ABL1.

The nucleic acid sequence of the m-BCR-ABL1 gene is typically represented by SEQ ID NO: 1, and a number of variants are known. The nucleic acid sequence of the M-BCR-ABL1 gene is typically represented by SEQ ID NO: 2 or 3, and a number of variants are known.

The m-BCR-ABL1 gene and the M-BCR-ABL1 gene may have a polynucleotide sequence that hybridizes to the polynucleotide having the nucleic acid sequence complementary to the sequence of SEQ ID NO: 1 and SEQ ID NO: 2 or 3, respectively, under a stringent condition. Regarding "hybridizes under a stringent condition", the hybridization may be carried out using a standard method, for example that described in "Molecular Cloning, T. Maniatis et al., CSH Laboratory (1983)". An example of the stringent condition is such that a hybrid is formed in a solution containing 6×SSC and 50% formamide at 45° C. and is washed with 2×SSC at 50° C., wherein 10×SSC is the solution containing 1.5 M NaCl and 0.15 M trisodium citrate (see "Molecular Biology, John Wiley & Sons, N. Y. (1989), 6.3.1-6.3.6"). Conditions that achieve the equivalent stringency also may be employed.

The m-BCR-ABL1 gene and the M-BCR-ABL1 gene may have a nucleic acid sequence having at least 70%, 80%, 85%, 90%, 95%, 96%, 97%, 98%, or 99% sequence identity with the nucleic acid sequence of SEQ ID NO: 1 and SEQ ID NO: 2 or 3, respectively. The term "sequence identity" means the degree of the similarity between two oligonucleotide sequences. The identity is determined by comparing two sequences that are optimally aligned with each other over the region subjected to the comparison. The term "optimally aligned" means the two sequences are aligned so that the number of the matched nucleotides is maximized. The numerical value (%) of the sequence identity is calculated by identifying the matched bases in the both sequences, determining the number of the matched bases, dividing the number by the total number of the bases in the region subjected to the comparison, and multiplying the derived numerical value by 100. For making the optimal alignment and calculating the sequence identity, various algorithms that are commonly available to those skilled in the art, e.g., BLAST algorithm and FASTA algorithm, may be used. The sequence identity may be determined using a software for sequence analysis such as BLAST and FASTA.

The subject is typically a human being. The subject may be a subject suffering from or suspected to be suffering from leukemia, e.g., chronic myelogenous leukemia (CML) or Philadelphia chromosome-positive acute lymphocytic leukemia (Ph+ALL).

The term"nucleic acid sample" as used herein means DNA obtained from the subject or cDNA generated by reverse-transcribing RNA obtained from the subject. The RNA may be total RNA or purified mRNA. The nucleic acid sample may be obtained from a specimen of the subject containing hematopoietic stem cells, leukocytes, or leukemia cells, for example, blood, bone marrow aspirate, or lymph. The nucleic acid sample may be obtained from isolated hematopoietic stem cells, blood cells, leukocytes, or leukemia cells. In an embodiment, the nucleic acid sample is obtained from leukocytes in peripheral blood or nucleated cells in bone marrow aspirate. In an embodiment, the nucleic acid sample is obtained from leukocytes in peripheral blood.

DNA or RNA may be extracted from a sample by any known method, for example, by acidifying a solution containing DNA or RNA and extracting it from an aqueous layer in PCI (phenol-chloroform-isoamyl alcohol extraction), by using a commercially available DNA or RNA extraction kit, or by any other known method.

Step (1) of the method uses a modified nucleic acid having a nucleic acid sequence of a part of exons 2 to 14 of the BCR gene or a nucleic acid sequence complementary thereto. The modified nucleic acid is capable of binding to a PCR amplification product derived from the Major BCR-ABL1 mRNA in a region corresponding to exons 2 to 14 of the BCR gene. The modified nucleic acid is herein referred to as "M-BCR clamp."

The term "modified nucleic acid" means a nucleic acid which comprises at least one artificial nucleotide, hybridizes to an mRNA or DNA more strongly than a DNA having the same nucleic acid sequence, and is not degraded by the exonuclease activity of reverse transcriptases and DNA polymerases. Reverse transcriptases and DNA polymerases stop the elongation reaction at the site where a modified nucleic acid is bound to a template mRNA or DNA. The M-BCR clamp binds to a polynucleotide derived from the M-BCR-ABL1 gene, which contains the nucleic acid sequence corresponding to exons 2 to 14 of the BCR gene, and suppresses the elongation reaction using the polynucleotide as the template. In contrast, the M-BCR clamp does not bind to a polynucleotide derived from the m-BCR-ABL1 gene, which does not contain the nucleic acid sequence corresponding to exons 2 to 14 of the BCR gene, and does not suppress the extension reaction using the polynucleotide as the template.

The M-BCR clamp may be designed as a modified nucleic acid having a nucleic acid sequence of about 10 to 30, about 15 to 25, about 19 to 23, or about 20 to 22, e.g., about 21 continuous nucleotides contained in exons 2 to 14, preferably exons 2 to 13, of the BCR gene, or a nucleic acid sequence complementary thereto. Exons 2 to 14 of the BCR gene has, for example, the nucleic acid sequence of SEQ ID NO: 4. Exons 2 to 13 of the BCR gene has, for example, the nucleic acid sequence of SEQ ID NO: 5. In an embodiment, the M-BCR clamp is designed so that it binds to the PCR amplification product of step (1) in a region close to the binding site of the forward or reverse primer. Specifically, the M-BCR clamp is designed to bind to the PCR amplification product in a region within about 300, about 200, about 150, or about 100 nucleotides from the binding site of the forward or reverse primer. In an embodiment, the M-BCR clamp is designed to bind to the PCR amplification product in the region corresponding to exons 12 and 13 of the BCR gene (e.g., SEQ ID NO: 6), for example, in the region corresponding to exon 13 (e.g., SEQ ID NO: 7). In an embodiment, the M-BCR clamp comprises the nucleic acid sequence of AGGGAGAAGCTTCTGAAACAC (SEQ ID NO: 8) or the nucleic acid sequence complementary thereto. In an embodiment, the M-BCR clamp consists of the nucleic acid sequence of SEQ ID NO: 8 or the nucleic acid sequence complementary thereto.

The M-BCR clamp comprises at least one artificial nucleotide. Artificial nucleotides that are different from natural nucleotides in their structures and improve the M-BCR clamp by enhancing the nuclease resistance and the binding affinity with the target sequence may be used. For example, artificial nucleotides used herein include those described in Deleavey, G. F., & Damha, M. J. (2012). Designing chemically modified oligonucleotides for targeted gene silencing. Chemistry & biology, 19(8), 937-954, the entire contents of which are incorporated herein by reference. Examples of the artificial nucleotides include abasic nucleosides; arabinonucleosides, 2'-deoxyuridine, alpha-deoxyribonucleosides, beta-L-deoxyribonucleosides, and nucleosides having any other sugar modification; peptide nucleic acids (PNA), peptide nucleic acids with phosphate groups (PHONA), locked nucleic acids (LNA), 2'-O, 4'-C-ethylene-bridged nucleic acids (ENA), constrained ethyl (cEt), and morpholino nucleic acids. Examples of the artificial nucleotides having sugar modifications include those having substituted pentoses such as 2'-o-methyl ribose, 2'-o-methoxyethyl ribose, 2'-deoxy-2'-fluoro ribose, or 3'-o-methyl ribose; 1',2'-deoxyribose; arabinose; substituted arabinoses; hexoses, and alpha-anomers. Examples of the artificial nucleotides having modified bases include those having pyrimidines such as 5-hydroxycytosine, 5-methylcytosine, 5-fluorouracil, or 4-thiouracil; purines such as 6-methyladenine and 6-thioguanosine; and other heterocyclic bases. The M-BCR clamp may comprise artificial nucleotides of the same type or two or more different types.

In an embodiment, the M-BCR clamp comprises at least one PNA portion as the artificial nucleotides. PNAs have peptide bonds between N-(2-aminoethyl)glycines and thus have DNA-like structures in which phosphodiester bonds of DNA are replaced with peptide bonds (Nielsen et al. 1991 Science 254, 1457-1500). PNAs are resistant to various nucleases and hybridize to DNAs or RNAs with the molecular recognition similar to that of DNAs and RNAs. The affinity between a PNA and a DNA is stronger than between a DNA and a DNA or between a DNA and a RNA. In an embodiment, all the nucleotides in the M-BCR clamp are those of PNAs.

In an embodiment, the nucleic acid sample is cDNA generated by reverse-transcribing a RNA sample obtained from the subject, whereby the expression of the minor BCR-ABL1 gene in the subject is detected. The reverse transcription may be carried out in the presence of a modified nucleic acid having a nucleic acid sequence complementary to a part of exons 2 to 14 of the BCR gene, i.e., M-BCR clamp. The modified nucleic acid can bind to the Major BCR-ABL1 mRNA in the region corresponding to exons 2 to 14 of the BCR gene. The M-BCR clamp used in the reverse transcription may be designed as a modified nucleic acid having a nucleic acid sequence complementary to about 10 to 30, about 15 to 25, about 19 to 23, or about 20 to 22, e.g., about 21 continuous nucleotides contained in exons 2 to 14, preferably exons 2 to 13, of the BCR gene. In an embodiment, the M-BCR clamp used in the reverse transcription is designed so that it binds to the M-BCR-ABL1 mRNA in a region close to the binding site of the reverse primer for the reverse transcription, i.e., in a region close to the 3' end of exons 2 to 14 of the BCR gene. Specifically, the M-BCR clamp is designed to bind to the M-BCR-ABL1 mRNA in a region within about 300, about 200, about 150, or about 100 nucleotides from the position at which the region derived from the BCR gene and the region derived from the ABL1 gene are fused. For example, the M-BCR clamp is designed to bind to the M-BCR-ABL1 mRNA in the region corresponding to exons 12 and 13 of the BCR gene (e.g., SEQ ID NO: 6), for example, in the region corresponding to exon 13 (e.g., SEQ ID NO: 7). In an embodiment, the M-BCR clamp used in the reverse transcription comprises the nucleic acid sequence AGGGAGAAGCTTCTGAAACAC (SEQ ID NO: 8). In an embodiment, the M-BCR clamp used in the reverse transcription consists of the nucleic acid sequence of SEQ ID NO: 8. The M-BCR clamp used in the reverse transcription may be produced and used similarly to the M-BCR clamp used in the PCR.

The M-BCR clamp used in the reverse transcription may have the same or different structure compared with the M-BCR clamp used in the PCR. In an embodiment, the M-BCR clamp used in the reverse transcription and the M-BCR clamp used in the PCR have the same structure.

The amount of the M-BCR clamp in the reverse transcription or the PCR can be any amount sufficient to suppress the reverse transcription or the PCR. For example, the concentration of the M-BCR clamp in the final reaction solution may be in the range about 0.01 μM to 10 μM, about 0.01 μM to 5 μM, about 0.01 μM to 1 μM, or about 0.01 μM to 0.1 μM, for example, about 0.025 μM, about 0.050 μM, or about 0.075 μM.

For the reverse transcription, a reverse primer having a nucleic acid sequence complementary to a part of exons 2 to 11 of the ABL1 gene is used. The primer can bind to the m-BCR-ABL1 mRNA and the M-BCR-ABL1 mRNA in the reverse transcription reaction to prime the elongation reaction. Exons 2 to 11 of the ABL1 gene has, for example, the nucleic acid sequence of SEQ ID NO: 9. The reverse primer for the reverse transcription may be designed on the basis of this nucleic acid sequence. For example, the reverse primer may be designed on the basis of the nucleic acid sequence of exon 2 of the ABL1 gene (e.g., SEQ ID NO: 10). In an embodiment, the reverse primer comprises the nucleic acid sequence CCTGAGGCTCAAAGTCAGATGCTAC (SEQ ID NO: 11). In an embodiment, the reverse primer consists of the nucleic acid sequence of SEQ ID NO: 11. Methods for designing primers suitable for reverse transcription are well known to those skilled in the art.

Reagents used in the reverse transcription reaction, such as reverse transcriptases, dNTPs, and buffers, may be those commonly used in the art. Reaction conditions such as the amount of each reagent, the reaction durations, and the reaction temperatures can be appropriately determined in a usual manner, for example according to the description of the package insert of the reverse transcriptase or protocols generally used in the art. For example, the reverse transcriptase may be any known reverse transcriptase used in molecular biological experiments, including Tth DNA polymerase, rTth DNA polymerase, AMV reverse transcriptase, MMLV reverse transcriptase, HIV reverse transcriptase, and derivatives thereof.

The forward primer and the reverse primer for the PCR may be designed so that the PCR product derived from the m-BCR-ABL1 mRNA has a length suitable for the amplification and quantification, for example, about 10 to 1000, about 20 to 500, about 50 to 300, about 100 to 200, about 130 to 180, about 150 to 160 nucleotides, e.g., about 155 nucleotides in length. Methods for designing primers suitable for PCR are well known to those skilled in the art.

The forward primer used in the PCR has a nucleic acid sequence of a part of exon 1 of the BCR gene. The primer can bind to the single strand DNA that is complementary to the m-BCR-ABL1 or M-BCR-ABL1 mRNA in the region corresponding to exon 1 of the BCR gene and prime the elongation reaction. Exon 1 of the BCR gene has, for example, the nucleic acid sequence of SEQ ID NO: 12. The forward primer may be designed on the basis of this nucleic acid sequence. In an embodiment, the forward primer comprises the nucleic acid sequence TCGCAACAGTCCTTCGACAG (SEQ ID NO: 13). In an embodiment, the forward primer consists of the nucleic acid sequence of SEQ ID NO: 13.

The reverse primer used in the PCR has a nucleic acid sequence complementary to a part of exons 2 to 11 of the ABL1 gene. The reverse primer can be designed in a similar manner to the reverse primer used in the reverse transcription. The reverse primer used in the PCR may have the same or different structure compared with the reverse primer used in the reverse transcription. In an embodiment, the reverse primer used in the reverse transcription and the reverse primer used in the PCR have the same structure.

The PCR may be a quantitative PCR such as a quantitative real-time PCR. Various fluorescent PCR techniques may be used for the quantitative real-time PCR. Examples of the fluorescent PCR techniques include, but not limited to, intercalator assays, which use a fluorescent nucleic acid binding dye such as SYBR GREEN I and an instrument such as LightCycler (registered trademark) of Roche or ABI Prizm 7700 Sequence Detection System (registered trademark) of Perkin Elmer Applied Biosystems; TaqMan probe assays, which monitor the amplification in real-time by virtue of 5' exonuclease activity of DNA polymerase; and cycling probe assays, which use RNase activity of RNaseH and a specialized chimeric RNA probe.

In an embodiment, a TaqMan probe assay is employed for the quantitative real-time PCR. In a TaqMan probe assay generally an oligonucleotide labeled with a fluorescent substance at the 5' end and a quencher at the 3' end (TaqMan probe) is added to the PCR reaction system. The TaqMan probe specifically hybridizes to the template DNA in the annealing step. At this step the fluorescence emission is suppressed due to the quencher on the probe even if excitation light is irradiated. At the elongation step the 5' exonuclease activity of Taq polymerase degrades the TaqMan probe hybridized to the template and releases the fluorescent substance from the quencher, allowing the fluorescence emission. The TaqMan probe can be designed by any method known in the art as a probe capable of binding somewhere on either strand of the PCR products derived from the m-BCR-ABL1 mRNA. Any combination of fluorescent substances and quenchers may be used. In an embodiment, the TaqMan probe comprises the nucleic acid sequence of ATCGTGGGCGTCCGCAAGAC (SEQ ID NO: 14). In an embodiment, the TaqMan probe consists of the nucleic acid sequence of SEQ ID NO: 14.

Amplification curves of the fluorescence may be created in the quantitative real-time PCR. A sample solution containing a cDNA at an unknown concentration and standard solutions containing the cDNA at known concentrations are simultaneously used in the quantitative real-time PCR. The amplification curves are generated by plotting the cycle numbers on the x-axis and the log-transformed fluorescence intensities from the reporter substance on the y-axis. The median value of the fluorescence intensities is determined in the range where the amplification curves are linear. A line parallel to the x-axis is drawn at the level near the median value. The cycle numbers at which the parallel line and the amplification curves cross are determined. Furthermore, a standard curve of the cDNA concentration is created by plotting the log-transformed cDNA concentrations in the standard solutions on the x-axis and the above-determined cycle numbers of the standard solutions on the y-axis. The cDNA concentration in the sample solution can be determined by using the above-determined cycle number of the sample and the standard curve of the cDNA concentration.

Since the same M-BCR clamp and the same reverse primer can be used in the reverse transcription and the PCR, the PCR may be conducted by adding the reagents required for the PCR to the whole products or a part of the products of the reverse transcription. For example, the reverse transcription and the PCR may be carried out simultaneously or sequentially in one step, i.e., in the same container. For example, step (1) may be conducted as a part of a quantitative real-time RT-PCR.

Reagents used in the PCR, such as DNA polymerases, dNTPs, and buffers, may be those commonly used in the art. Reaction conditions such as the amount of each reagent, the reaction durations, and the reaction temperatures can be appropriately determined in a usual manner, for example according to the description of the package insert of the enzyme or protocols generally used in the art. For example, the DNA polymerase may be any known DNA polymerase used in molecular biological experiments, including rTth DNA polymerase, Taq polymerase, and derivatives thereof.

In step (2), the subject is determined to have the minor BCR-ABL1 gene when the nucleic acid amplification is occurred in the PCR. The nucleic acid amplification can be detected by any known method for detecting nucleic acids.

For example, the amplification may be detected by electrophoresis of the nucleic acids after the amplification; hybridization with a nucleic acid probe labeled with a detectable label; staining of double-stranded DNAs with an intercalating fluorescent dye; or using a fluorescent probe. The nucleic acid amplification may be detected in the quantitative PCR as described above.

In parallel with step (1), the nucleic acids comprising the nucleic acid sequence corresponding to exons 2 to 11 of the ABL1 gene (e.g., SEQ ID NO:9) may be quantitated and the measurement may be compared with that of the m-BCR-ABL1 gene. The nucleic acids comprising the nucleic acid sequence corresponding to exons 2 to 11 of the ABL1 gene may be derived from the ABL1 gene, the m-BCR-ABL1 gene, and the M-BCR-ABL1 gene. For example, the measurement of the nucleic acids of the m-BCR-ABL1 gene obtained in step (1) may be divided by the measurement of the nucleic acids comprising the nucleic acid sequence corresponding to exons 2 to 11 of the ABL1 gene to give the normalized measurement of the m-BCR-ABL1 gene. Similarly, the measurement of the m-BCR-ABL1 gene may be normalized with a measurement of a housekeeping gene.

In an embodiment, the primer, clamp, and probe shown in Table 1 below are used. All of them may be used in combination or at least one of them may be used.

TABLE 1

| | |
|---|---|
| Forward primer | TCGCAACAGTCCTTCGACAG (SEQ ID NO: 13) |
| Reverse primer | CCTGAGGCTCAAAGTCAGATGCTAC (SEQ ID NO: 11) |
| Probe | ATCGTGGGCGTCCGCAAGAC (SEQ ID NO: 14) |
| Clamp | AGGGAGAAGCTTCTGAAACAC (SEQ ID NO: 8) |

An aspect of the disclosure provides a kit for conducting the method disclosed herein. The kit comprises at least;

(a) a modified nucleic acid having a nucleic acid sequence of a part of exons 2 to 14 of the BCR gene or a nucleic acid sequence complementary thereto;
(b) a reverse primer having a nucleic acid sequence complementary to a part of exons 2 to 11 of the ABL1 gene; and
(c) a forward primer having a nucleic acid sequence of a part of exon 1 of the BCR gene.

The kit may further comprise at least one of a second modified nucleic acid, a second reverse primer, and a probe for a quantitative PCR. The kit may further comprise a standard, e.g., a known amount of the minor BCR-ABL1 mRNA. The kit may further comprise a primer for quantitating mRNA of a control gene (e.g., mRNA containing at least a part of the nucleic acid sequence corresponding to exons 2 to 11 of the ABL1 gene). The kit may further comprise at least one of the reagents necessary for conducting the method disclosed herein, for example, the reagents for reverse transcription, PCR, or quantitative PCR, including reverse transcriptases, DNA polymerases, dNTPs, and buffers. The kit may further comprise any component preferred for marketing or using the kit, for example, a package insert (e.g., a document or a storage medium) containing description for using the kit.

The components of the kit are provided individually or, if possible, in a mixture. Each component may be provided in a solution in water or a suitable buffer, or in the lyophilized form, contained in a suitable container. Examples of the suitable containers include bottles, vials, test tubes, tubes, plates, and multi-well plates. The container may be made of at least one material, such as glass, plastic, or metal. The container may have a label.

In an aspect, the disclosure provides a method of detecting the expression of the minor BCR-ABL1 gene in a subject, comprising:

(1) reverse-transcribing an RNA sample obtained from the subject using a first reverse primer having a nucleic acid sequence complementary to a part of exons 2 to 11 of the ABL1 gene in the presence of a modified nucleic acid having a nucleic acid sequence complementary to a part of exons 2 to 14 of the BCR gene;
(2) conducting a PCR using a forward primer having a nucleic acid sequence of a part of exon 1 of the BCR gene and a second reverse primer having a nucleic acid sequence complementary to a part of exons 2 to 11 of the ABL1 gene; and
(3) determining that the subject is expressing the minor BCR-ABL1 gene when the nucleic acid amplification is occurred in the PCR.

The details of the method are similar to those of the method described earlier.

For example, the disclosure provides the following embodiments.

[1] A method of detecting the minor BCR-ABL1 gene in a subject, comprising:

(1) conducting a PCR using a nucleic acid sample obtained from the subject as the template, a forward primer having a nucleic acid sequence of a part of exon 1 of the BCR gene, and a reverse primer having a nucleic acid sequence complementary to a part of exons 2 to 11 of the ABL1 gene, in the presence of a modified nucleic acid having a nucleic acid sequence of a part of exons 2 to 14 of the BCR gene or a nucleic acid sequence complementary thereto; and
(2) determining that the subject has the minor BCR-ABL1 gene when the nucleic acid amplification is occurred in the PCR.

[2] The method according to item 1, wherein the nucleic acid sample is cDNA generated by reverse-transcribing an RNA sample obtained from the subject.

[3] The method according to item 1 or 2, wherein the nucleic acid sample is cDNA generated by reverse-transcribing an RNA sample obtained from the subject in the presence of a modified nucleic acid having a nucleic acid sequence complementary to a part of exons 2 to 14 of the BCR gene.

[4] A method of detecting the expression of the minor BCR-ABL1 gene in a subject, comprising:

(1) reverse-transcribing an RNA sample obtained from the subject using a first reverse primer having a nucleic acid sequence complementary to apart of exons 2 to 11 of the ABL1 gene;
(2) conducting a PCR using the reverse transcript obtained in step (1) as the template, a forward primer having a nucleic acid sequence of a part of exon 1 of the BCR gene, and a reverse primer having a nucleic acid sequence complementary to a part of exons 2 to 11 of the ABL1 gene, in the presence of a modified nucleic acid having a nucleic acid sequence of a part of exons 2 to 14 of the BCR gene or a nucleic acid sequence complementary thereto; and
(3) determining that the subject is expressing the minor BCR-ABL1 gene when the nucleic acid amplification is occurred in the PCR.

[5] A method of detecting the expression of the minor BCR-ABL1 gene in a subject, comprising:

(1) reverse-transcribing an RNA sample obtained from the subject using a first reverse primer having a nucleic acid sequence complementary to a part of exons 2 to 11 of the ABL1 gene in the presence of a modified nucleic acid having a nucleic acid sequence complementary to a part of exons 2 to 14 of the BCR gene;

(2) conducting a PCR using the reverse transcript obtained in step (1) as the template, a forward primer having a nucleic acid sequence of a part of exon 1 of the BCR gene, and a second reverse primer having a nucleic acid sequence complementary to a part of exons 2 to 11 of the ABL1 gene; and (3) determining that the subject is expressing the minor BCR-ABL1 gene when the nucleic acid amplification is occurred in the PCR.

[6] A method of detecting the expression of the minor BCR-ABL1 gene in a subject, comprising:

(1) reverse-transcribing an RNA sample obtained from the subject using a first reverse primer having a nucleic acid sequence complementary to a part of exons 2 to 11 of the ABL1 gene in the presence of a modified nucleic acid having a nucleic acid sequence complementary to a part of exons 2 to 14 of the BCR gene;

(2) conducting a PCR using the reverse transcript obtained in step (1) as the template, a forward primer having a nucleic acid sequence of a part of exon 1 of the BCR gene, and a reverse primer having a nucleic acid sequence complementary to a part of exons 2 to 11 of the ABL1 gene, in the presence of a modified nucleic acid having a nucleic acid sequence of a part of exons 2 to 14 of the BCR gene or a nucleic acid sequence complementary thereto; and (3) determining that the subject is expressing the minor BCR-ABL1 gene when the nucleic acid amplification is occurred in the PCR.

[7] The method according to any one of items 1 to 6, wherein the modified nucleic acid has a nucleic acid sequence of a part of exons 2 to 13 of the BCR gene or a nucleic acid sequence complementary thereto.

[8] The method according to any one of items 1 to 7, wherein the modified nucleic acid has a nucleic acid sequence of a part of exons 12 and 13 of the BCR gene or a nucleic acid sequence complementary thereto.

[9] The method according to any one of items 1 to 8, wherein the modified nucleic acid comprises about 10 to 30 nucleotides.

[10] The method according to any one of items 1 to 9, wherein the modified nucleic acid comprises about 21 nucleotides.

[11] The method according to any one of items 1 to 10, wherein the modified nucleic acid comprises the nucleic acid sequence of SEQ ID NO: 8.

[12] The method according to any one of items 1 to 11, wherein the modified nucleic acid consists of the nucleic acid sequence of SEQ ID NO: 8.

[13] The method according to any one of items 1 to 12, wherein the modified nucleic acid comprises a PNA portion.

[14] The method according to any one of items 3 and 6 to 13, wherein the modified nucleic acid used in the reverse transcription and the modified nucleic acid used in the PCR have the same structure.

[15] The method according to any one of items 1 to 14, wherein the reverse primer used in the reverse transcription or the reverse primer used in the PCR comprises the nucleic acid sequence of SEQ ID NO: 11.

[16] The method according to any one of items 1 to 15, wherein the reverse primer used in the reverse transcription or the reverse primer used in the PCR consists of the nucleic acid sequence of SEQ ID NO: 11.

[17] The method according to any one of items 2 to 16, wherein the reverse primer used in the reverse transcription and the reverse primer used in the PCR have the same structure.

[18] The method according to any one of items 1 to 17, wherein the forward primer comprises the nucleic acid sequence of SEQ ID NO: 13.

[19] The method according to any one of items 1 to 18, wherein the forward primer consists of the nucleic acid sequence of SEQ ID NO: 13.

[20] The method according to any one of items 2 to 19, wherein the reverse transcription and the PCR are carried out in the same container.

[21] The method according to any one of items 1 to 20, wherein the PCR is a quantitative PCR.

[22] The method according to any one of items 1 to 21, wherein the PCR is a quantitative real-time RT-PCR.

[23] The method according to any one of items 1 to 22, wherein the subject is a human being.

[24] The method according to any one of items 1 to 23, wherein the nucleic acid sample is a nucleic acid sample extracted from leukocytes in peripheral blood or nucleated cells in bone marrow aspirate.

[25] The method according to any one of items 1 to 24, wherein the nucleic acid sample is a nucleic acid sample extracted from leukocytes in peripheral blood.

[26] The method according to any one of items 1 to 25, wherein at least one of the primer, clamp, and probe shown in Table 1 is used.

[27] The method according to any one of items 1 to 26, wherein the primer, clamp, and probe shown in Table 1 are used.

[28] A kit for detecting the minor BCR-ABL1 gene in a subject, comprising a modified nucleic acid having a nucleic acid sequence of a part of exons 2 to 14 of the BCR gene or a nucleic acid sequence complementary thereto, a reverse primer having a nucleic acid sequence complementary to a part of exons 2 to 11 of the ABL1 gene, and a forward primer having a nucleic acid sequence of a part of exon 1 of the BCR gene.

[29] A kit for detecting the expression of the minor BCR-ABL1 gene in a subject, comprising a modified nucleic acid having a nucleic acid sequence of a part of exons 2 to 14 of the BCR gene or a nucleic acid sequence complementary thereto, a reverse primer having a nucleic acid sequence complementary to a part of exons 2 to 11 of the ABL1 gene, and a forward primer having a nucleic acid sequence of a part of exon 1 of the BCR gene.

[30] The kit according to item 28 or 29, wherein the modified nucleic acid has a nucleic acid sequence of a part of exons 2 to 13 of the BCR gene or a nucleic acid sequence complementary thereto.

[31] The kit according to any one of items 28 to 30, wherein the modified nucleic acid has a nucleic acid sequence of a part of exons 12 of the BCR gene or a nucleic acid sequence complementary thereto.

[32] The kit according to any one of items 28 to 31, wherein the modified nucleic acid comprises about 10 to 30 nucleotides.

[33] The kit according to any one of items 28 to 32, wherein the modified nucleic acid comprises 21 nucleotides.

[34] The kit according to any one of items 28 to 33, wherein the modified nucleic acid comprises the nucleic acid sequence of SEQ ID NO: 8.

[35] The kit according to any one of items 28 to 34, wherein the modified nucleic acid consists of the nucleic acid sequence of SEQ ID NO: 8.

[36] The kit according to any one of items 28 to 35, wherein the modified nucleic acid comprises a PNA portion.

[37] The kit according to any one of items 28 to 36, wherein the reverse primer comprises the nucleic acid sequence of SEQ ID NO: 11.

[38] The kit according to any one of items 28 to 37, wherein the reverse primer consists of the nucleic acid sequence of SEQ ID NO: 11.

[39] The kit according to any one of items 28 to 38, wherein the forward primer comprises the nucleic acid sequence of SEQ ID NO: 13.

[40] The kit according to any one of items 28 to 39, wherein the forward primer consists of the nucleic acid sequence of SEQ ID NO: 13.

[41] The kit according to any one of items 28 to 40, further comprising a probe fora quantitative PCR.

[42] The kit according to any one of items 28 to 41, further comprising a second modified nucleic acid.

[43] The kit according to any one of items 28 to 42, further comprising a second reverse primer.

[44] The kit according to any one of items 28 to 43, further comprising the minor BCR-ABL1 mRNA.

[45] The kit according to any one of items 28 to 44, comprising at least one of the primer, clamp, and probe shown in Table 1.

[46] The kit according to any one of items 28 to 45, comprising the primer, clamp, and probe shown in Table 1.

The entire contents of the documents cited herein are incorporated herein by reference.

The embodiments described above are non-limiting and may be modified without deviating from the scope of the invention as defined by the appended claims. The following example does not restrict or limit the invention and is for illustrative purposes only.

Example 1

Preparation of Reaction Solutions for RT-PCR

The RT-PCR reaction mixture of the composition shown in the following table was prepared.

TABLE 2

| | |
|---|---|
| HawkZ05 Fast One-Step RT-PCR Master Mix (Roche Diagnostics) | 1x |
| 25 mM manganese acetate (Roche Diagnostics) | 2.5 mM |
| minor BCR-ABL1 forward prime (NIHON GENE RESEARCH LABORATORIES Inc.,) | 0.4 μM |
| minor BCR-ABL1 reverse primer (NIHON GENE RESEARCH LABORATORIES Inc.,) | 0.4 μM |
| minor BCR-ABL fluorescence-labeled probe (NIHON GENE RESEARCH LABORATORIES Inc.,) | 0.2 μM |
| ABL1 forward primer (NIHON GENE RESEARCH LABORATORIES Inc.,) | 0.2 μM |
| ABL1 reverse primer (NIHON GENE RESEARCH LABORATORIES Inc.,) | 0.2 μM |
| ABL1 fluorescence-labeled probe (NIHON GENE RESEARCH LABORATORIES Inc.,) | 0.1 μM |

The minor BCR-ABL mRNA fluorescence-labeled probe had 6-FAM (6-carboxyfluorescein) as the reporter substance and ATT0540Q as the quencher. The ABL1 fluorescence-labeled probe had HEX (hexachlorofluorescein) as the reporter substance and ATT0540Q as the quencher. To the RT-PCR reaction mixture, a PNA clamp (Panagene) that is capable of specifically binding to an mRNA encoding a part of exon 12 of the BCR gene was added at the final concentration of 0, 0.025, 0.05, or 0.075 μM.

The nucleic acid sequences of each component are shown in the following table.

TABLE 3

| | |
|---|---|
| minor BCR-ABL1 forward primer | TCGCAACAGTCCTTCGACAG (SEQ ID NO: 13) |
| minor BCR-ABL1 reverse primer | CCTGAGGCTCAAAGTCAGATGCTAC (SEQ ID NO: 11) |
| minor BCR-ABL fluorescence-labeled probe | ATCGTGGGCGTCCGCAAGAC (SEQ ID NO: 14) |
| ABL1 forward primer | CAGAGCTGCCCACCAAGAC (SEQ ID NO: 15) |
| ABL1 reverse primer | AGAAGGCGCTCATCTTCATTCAG (SEQ ID NO: 16) |
| ABL1 fluorescence-labeled probe | CTGAGATGCCTCACTCCAAGGGC (SEQ ID NO: 17) |
| PNA clamp | AGGGAGAAGCTTCTGAAACAC (SEQ ID NO: 8) |

Sample Preparation (1) RNA standard having the nucleic acid sequence of the Major BCR-ABL1 mRNA RNA comprising the nucleic acid sequence of the Major BCR-ABL1 mRNA (SEQ ID NO: 18) was synthesized in vitro. The concentration of the RNA was adjusted so that $1.0\times10^7$ or $1.0\times10^6$ copies of the RNA were used for each reaction.

(2) RNA standard having the nucleic acid sequence of the minor BCR-ABL1 mRNA

RNA comprising the nucleic acid sequence of the minor BCR-ABL1 mRNA (SEQ ID NO: 19) was synthesized in vitro. The concentration of the RNA was adjusted so that $1.0\times10^7$, $1.0\times10^5$, $1.0\times10^3$, $1.0\times10^2$, or $1.0\times10^1$ copies were used for each reaction.

(3) RNA standard having the nucleic acid sequence of the ABL1 mRNA

RNA comprising the nucleic acid sequence of the ABL1 mRNA (SEQ ID NO: 20) was synthesized in vitro. The concentration of the RNA was adjusted so that $1.0\times10^7$, $1.0\times10^5$, $1.0\times10^3$, or $1.0\times10^2$ copies were used for each reaction.

Reaction Conditions of RT-PCR

The RT-PCR was carried out under the following conditions. Instrument: Applied biosystems 7500 Fast realtime PCR system Temperature conditions: After the reaction at 37° C. for 5 minutes, at 65° C. for 15 minutes, and at 94° C. for 1 minute, the reaction cycle at 94° C. for 5 seconds and at 67° C. for 40 seconds was repeated 45 times.

Test 1: The Effect of the PNA Clamp on the Amplification of the Minor BCR-ABL1 mRNA and the ABL1 mRNA The RNA standard having the nucleic acid sequence of the minor BCR-ABL1 mRNA (2) and the RNA standard having the nucleic acid sequence of the ABL1 mRNA were subjected to the RT-PCR using the reagents and the reaction conditions described above.

Figure 6:
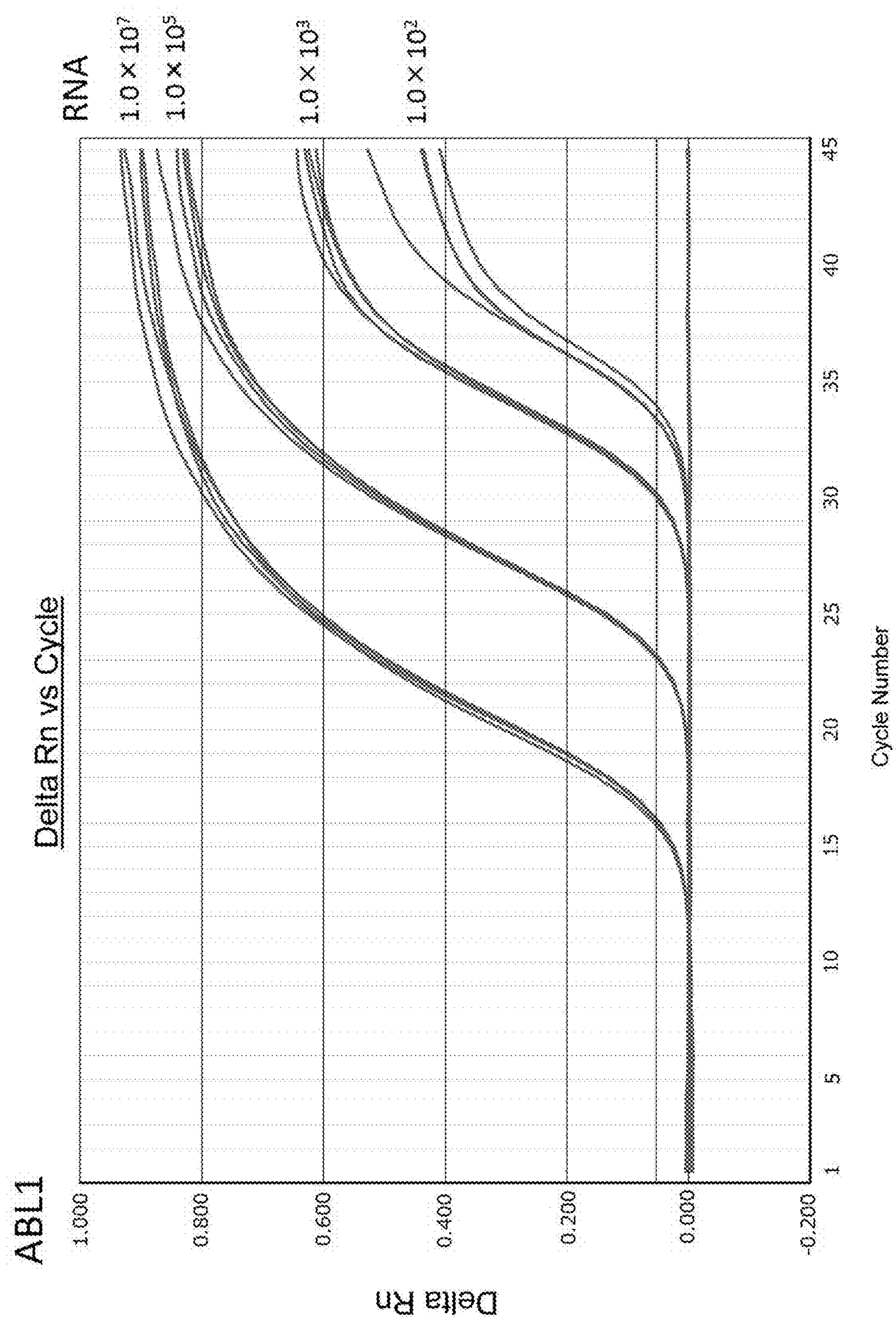
FIG. 6 shows the amplification curves of the ABL1 mRNA in the presence of PNA in the RT-PCR in Test 1.

The amplification curves of the minor BCR-ABL1 mRNA (minor) and the ABL1 mRNA (ABL1) are shown in FIGS. 5 and 6, respectively. The cycle numbers of the RT-PCR at the threshold (Cycle of threshold: Ct) are shown in the following table. The added PNA clamp had no effect on the amplification.

TABLE 4

| RNA conc. (copies/ reaction) | No PNA clamp | | PNA clamp 0.025 μM | | PNA clamp 0.05 μM | | PNA clamp 0.075 μM | |
|---|---|---|---|---|---|---|---|---|
| | minor | ABL1 | minor | ABL1 | minor | ABL1 | minor | ABL1 |
| 1.00E+07 | 16.23 | 17.09 | 16.52 | 17.31 | 16.51 | 17.33 | 16.48 | 17.37 |
| 1.00E+05 | 23.74 | 24.21 | 23.80 | 24.30 | 23.79 | 24.35 | 23.76 | 24.32 |
| 1.00E+03 | 30.81 | 31.16 | 30.97 | 31.20 | 31.08 | 31.26 | 31.07 | 31.36 |
| 1.00E+02 | 34.78 | 34.57 | 34.07 | 34.50 | 34.20 | 34.56 | 34.18 | 35.10 |
| 1.00E+01 | 39.05 | — | 38.51 | — | 38.14 | — | 38.90 | — |

—: not tested

Test 2: The Effect of the PNA Clamp on the Amplification of the Major BCR-ABL1 mRNA and the ABL1 mRNA The RNA standard having the nucleic acid sequence of the Major BCR-ABL1 mRNA (1) and the RNA standard having the nucleic acid sequence of the ABL1 mRNA were subjected to the RT-PCR using the reagents and the reaction conditions described above.

Figure 7:
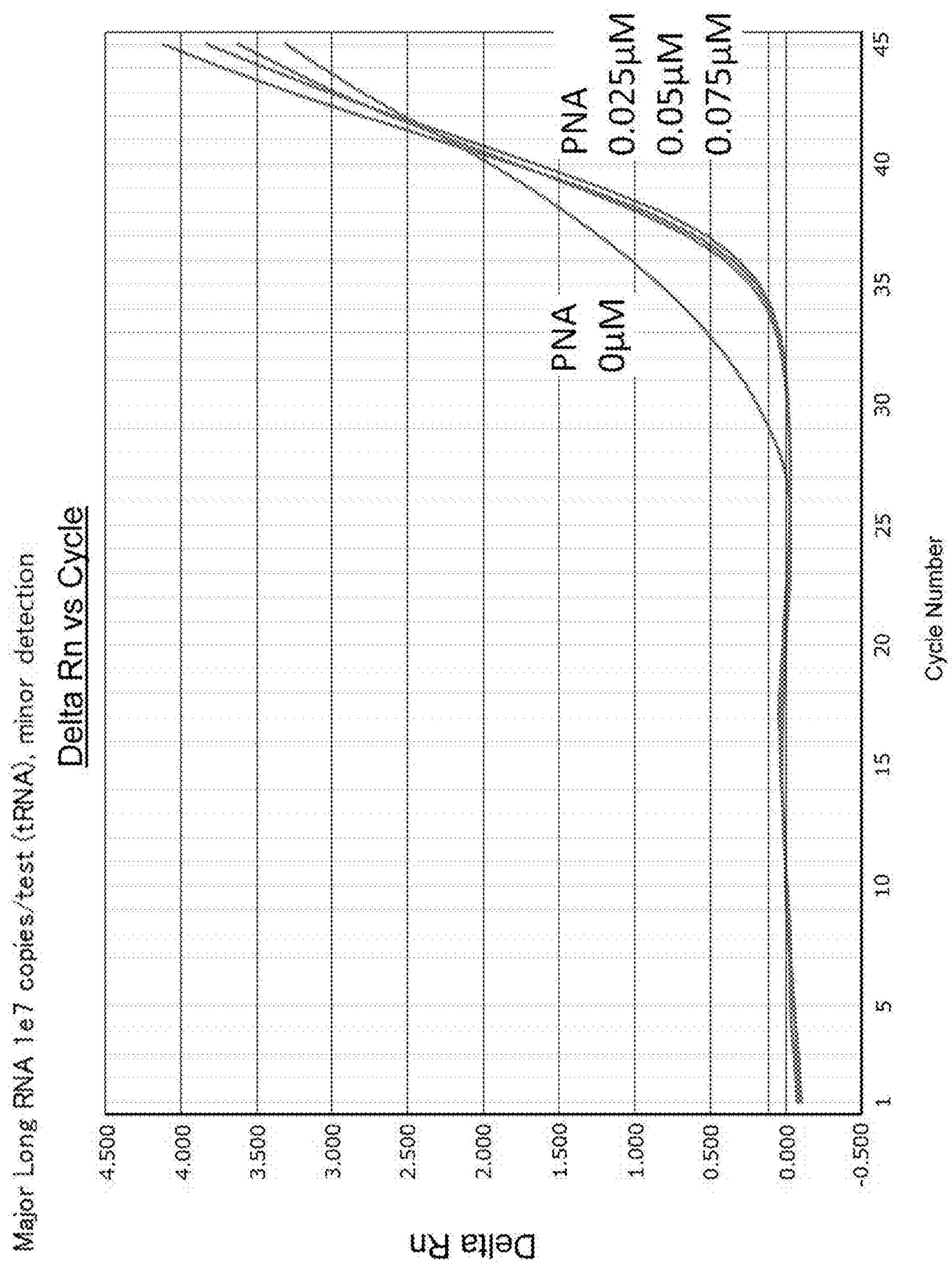
FIG. 7 shows the amplification curves of $1.0\times10^7$ copies of the Major BCR-ABL1 mRNA in the presence of PNA in the RT-PCR in Test 2.
Figure 8:
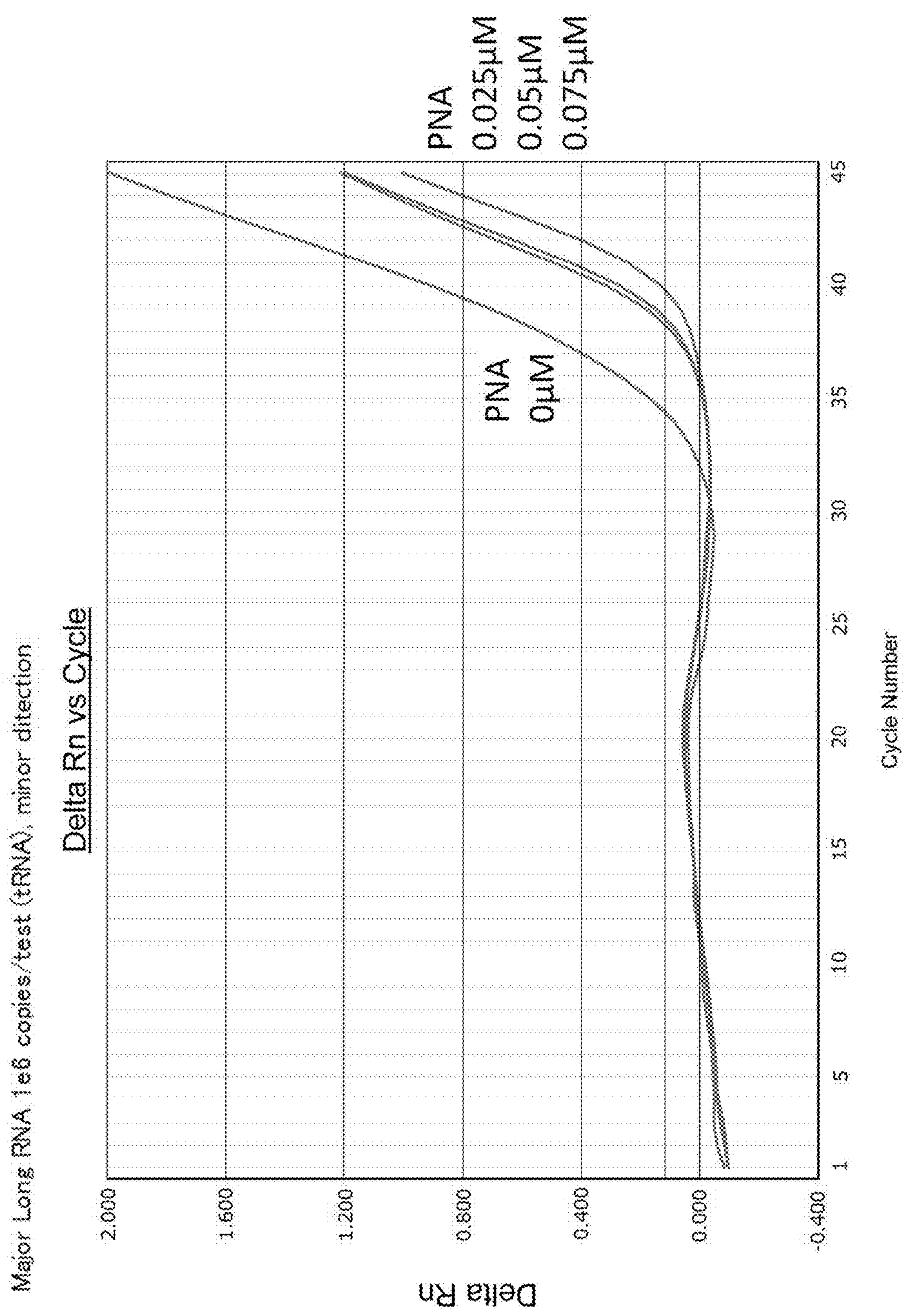
FIG. 8 shows the amplification curves of $1.0\times10^6$ copies of the Major BCR-ABL1 mRNA in the presence of PNA in the RT-PCR in Test 2.
Figure 9:
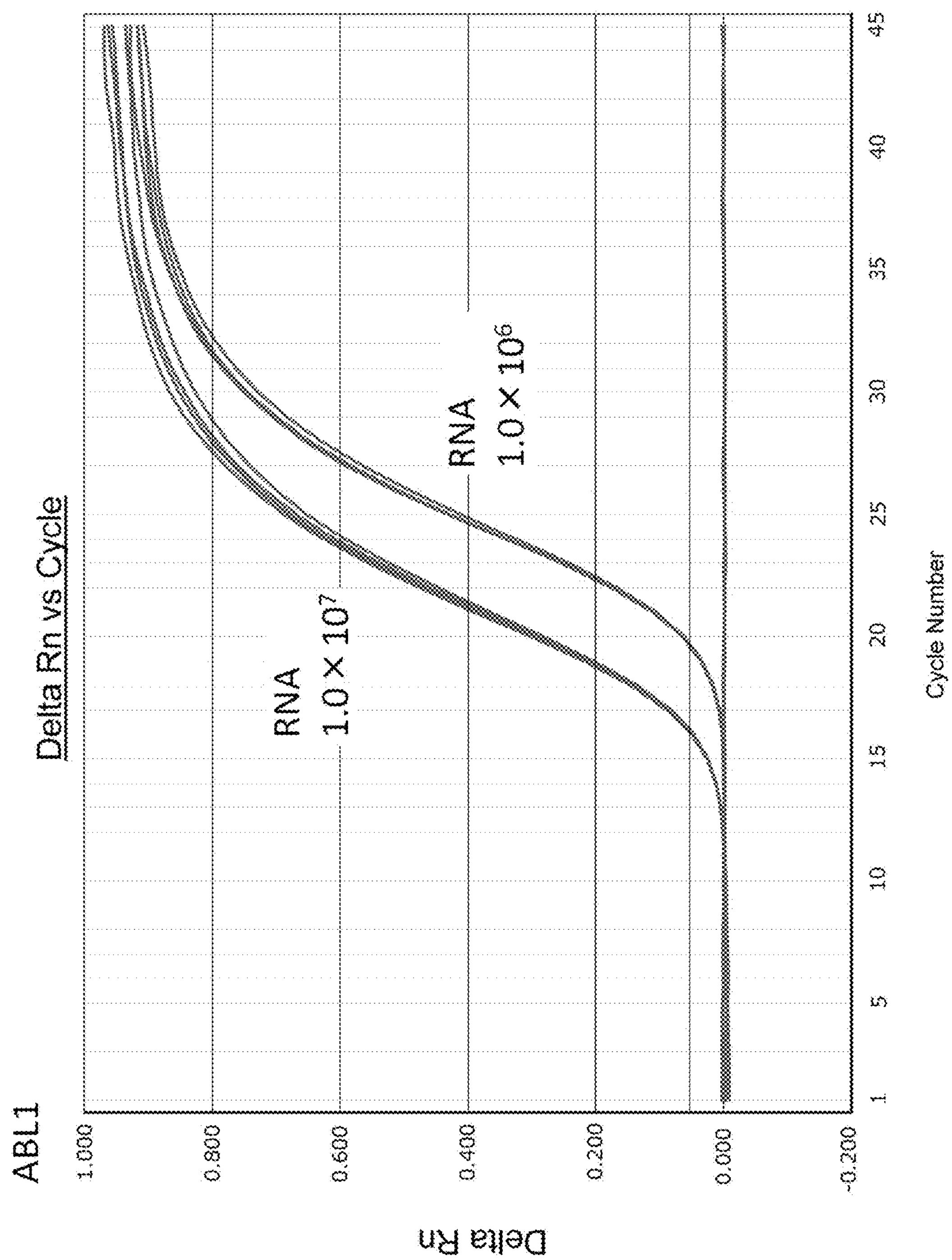
FIG. 9 shows the amplification curves of the ABL1 mRNA in the presence of PNA in the RT-PCR in Test 2.

For the Major BCR-ABL1 mRNA (Major) and the ABL1 mRNA (ABL1), the cycle numbers of the RT-PCR at the threshold (Cycle of threshold: Ct) are shown in the following table. The amplification curves are shown in FIGS. 7 to 9. The Major BCR-ABL1 mRNA was amplified in the absence of the PNA clamp, though the amplification product was very long, i.e., 1630 bp or 1705 bp in length. The Ct values were increased by adding the PNA clamp, indicating the amplification was inhibited. The added PNA clamp had no effect on the amplification of the ABL1 mRNA.

TABLE 5

| RNA conc. (copies/ reaction) | No PNA clamp | | PNA clamp 0.025 μM | | PNA clamp 0.05 μM | | PNA clamp 0.075 μM | |
|---|---|---|---|---|---|---|---|---|
| | minor | ABL1 | minor | ABL1 | minor | ABL1 | minor | ABL1 |
| 1.00E+07 | 30.08 | 17.18 | 35.01 | 17.23 | 35.16 | 17.33 | 34.70 | 17.24 |
| 1.00E+06 | 35.33 | 20.75 | 40.63 | 20.78 | 39.14 | 20.85 | 39.42 | 20.77 |

The standard curve for the mRNA concentration was created using the mRNA concentrations of the minor BCR-ABL1 mRNA and the ABL1 mRNA as well as the cycle numbers at the threshold shown in Table 4. Using the standard curve, the mRNA concentrations were calculated for the cycle numbers at the threshold shown in Table 5. The results are shown in Table 6.

The concentration of the Major BCR-ABL1 mRNA detected by the system for detecting the concentration of the minor BCR-ABL1 mRNA was lower in the presence of the PNA than in the absence of the PNA. This indicates that the added PNA inhibited the amplification of the Major BCR-ABL1 mRNA. The added PNA had no effect on the concentration of the Major BCR-ABL1 mRNA detected in the system for detecting the concentration of the ABL1 mRNA.

TABLE 6

| RNA conc. (copies/ reaction) | No PNA clamp | | PNA clamp 0.025 μM | |
|---|---|---|---|---|
| | minor | ABL1 | minor | ABL1 |
| 1.00E+07 | 1.96E+03 | 9.75E+06 | 7.43E+01 | 1.09E+07 |
| 1.00E+06 | 7.89E+01 | 9.30E+05 | 2.06E+00 | 1.01E+06 |

| RNA conc. (copies/ reaction) | PNA clamp 0.05 μM | | PNA clamp 0.075 μM | |
|---|---|---|---|---|
| | minor | ABL1 | minor | ABL1 |
| 1.00E+07 | 6.44E+01 | 1.04E+07 | 1.04E+02 | 1.04E+07 |
| 1.00E+06 | 4.99E+00 | 9.90E+05 | 5.37E+00 | 1.05E+06 |

INDUSTRIAL APPLICABILITY

The disclosure can provide a method of detecting the minor BCR-ABL1 gene or determining the expression level thereof more precisely than the methods of the prior art. Accordingly, the method or the kit disclosed herein can detect the minor BCR-ABL1 gene or determine the expression level thereof with high precision, being useful for, e.g., diagnosing onset or recurrence of leukemia, predicting prognosis of leukemia, and determining timing of bone marrow transplantation.

What is claimed is:

1. A method of detecting the minor BCR-ABL11 gene in a subject, comprising:

(1) conducting a PCR using a nucleic acid sample obtained from the subject as the template, a forward primer having a nucleic acid sequence of a part of exon 1 of the BCR gene, and a reverse primer having a nucleic acid sequence complementary to a part of exons 2 to 11 of the ABL11 gene, and a probe capable of binding to either strand of PCR products derived from the m-BCR-ABL1 mRNA by conducting said PCR, in the presence of a modified nucleic acid having a nucleic acid sequence of a part of exons 2 to 14 of the BCR gene or a nucleic acid sequence complementary thereto, wherein the modified nucleic acid stops an elongation reaction at the site where said modified nucleic acid is bound and wherein said modified nucleic acid is not degraded by the exonuclease activity of a reverse transcriptase or a DNA polymerase, and wherein a portion of the nucleic acid sequence of the template complementary to the forward primer and a portion of the nucleic acid sequence of the template complementary to the reverse primer do not overlap a portion of the nucleic acid sequence of the template complementary to the modified nucleic acid; and (2) determining that the subject has the minor BCR-ABL11 gene when the nucleic acid amplification has occurred in the PCR.

2. The method according to claim 1, wherein the modified nucleic acid has a nucleic acid sequence of a part of exons 2 to 13 of the BCR gene or a nucleic acid sequence complementary thereto.

3. The method according to claim 1, wherein the modified nucleic acid has a nucleic acid sequence of a part of exons 12 and 13 of the BCR gene or a nucleic acid sequence complementary thereto.

4. The method according to claim 1, wherein the modified nucleic acid comprises about 10 to 30 nucleotides.

5. The method according to claim 1, wherein the modified nucleic acid comprises the nucleic acid sequence of SEQ ID NO: 8.

6. The method according to claim 1, wherein the modified nucleic acid comprises a PNA portion.

7. The method according to claim 1, wherein the nucleic acid sample is cDNA generated by reverse-transcribing an RNA sample obtained from the subject.

8. The method according to claim 1, wherein the nucleic acid sample is cDNA generated by reverse-transcribing an RNA sample obtained from the subject in the presence of a modified nucleic acid having a nucleic acid sequence complementary to a part of exons 2 to 14 of the BCR gene.

9. The method according to claim 8, wherein the modified nucleic acid used in the reverse transcription and the modified nucleic acid used in the PCR have the same structure.

10. The method according to claim 7, wherein the reverse primer used in the reverse transcription and the reverse primer used in the PCR have the same structure.

11. The method according to claim 7, wherein the reverse transcription and the PCR are carried out in the same container.

12. The method according to claim 1, wherein the PCR is a quantitative PCR.

13. The method according to claim 1, wherein the PCR is a quantitative real-time RT-PCR.

14. The method according to claim 1, wherein the subject is a human being.

15. The method according to claim 1, wherein the nucleic acid sample is a nucleic acid sample extracted from leukocytes in peripheral blood or nucleated cells in bone marrow aspirate.

16. A method of detecting the expression of the minor BCR-ABL11 gene in a subject, comprising:

(1) reverse-transcribing an RNA sample obtained from the subject using a first reverse primer having a nucleic acid sequence complementary to a part of exons 2 to 11 of the ABL11 gene in the presence of a modified nucleic acid having a nucleic acid sequence complementary to a part of exons 2 to 14 of the BCR gene to obtain a cDNA template, wherein the modified nucleic acid stops an elongation reaction at the site where said modified nucleic acid is bound and wherein said modified nucleic acid is not degraded by the exonuclease activity of a reverse transcriptase or a DNA polymerase;

(2) conducting a PCR using a forward primer having a nucleic acid sequence of a part of exon 1 of the BCR gene and a second reverse primer having a nucleic acid sequence complementary to a part of exons 2 to 11 of the ABL11 gene, and a probe capable of binding to either strand of the PCR products derived from the m-BCR-ABL1 mRNA by conducting said PCR, wherein a portion of the nucleic acid sequence of the cDNA template complementary to the forward primer and a portion of the nucleic acid sequence of the cDNA template complementary to the second reverse primer do not overlap a portion of the nucleic acid sequence of the cDNA template complementary to the modified nucleic acid; and (3) determining that the subject is expressing the minor BCR-ABL11 gene when the nucleic acid amplification has occurred in the PCR.

17. The method according to claim 1, wherein the forward primer comprises the nucleic acid sequence of SEQ ID NO: 13.

18. The method according to claim 1, wherein the reverse primer comprises the nucleic acid sequence of SEQ ID NO: 11.

19. The method according to claim 1, wherein the modified nucleic acid comprises the nucleic acid sequence of SEQ ID NO: 8, the forward primer comprises the nucleic acid sequence of SEQ ID NO: 13, the reverse primer comprises the nucleic acid sequence of SEQ ID NO: 11, and the probe comprises the nucleic acid sequence of SEQ ID NO: 14.

* * * * *

SEQUENCE LISTING

```
<160> NUMBER OF SEQ ID NOS: 20

<210> SEQ ID NO 1
<211> LENGTH: 7200
<212> TYPE: DNA
<213> ORGANISM: Homo sapiens

<400> SEQUENCE: 1

gggggagggg tggcggctcg atgggggagc cgcctccagg gggccccccc gccctgtgcc      60

cacggcgcgg cccctttaag aggcccgcct ggctccgtca tccgcgccgc ggccacctcc     120

ccccggccct ccccttcctg cggcgcagag tgcgggccgg gcgggagtgc ggcgagagcc     180

ggctggctga gcttagcgtc cgaggaggcg gcggcggcgg cggcggcacg gcggcggcgg     240

ggctgtgggg cggtgcggaa gcgagaggcg aggagcgcgc gggccgtggc cagagtctgg     300

cggcggcctg gcggagcgga gagcagcgcc cgcgcctcgc cgtgcggagg agccccgcac     360

acaatagcgg cgcgcgcagc ccgcgccctt ccccccggcg cgccccgccc cgcgcgccga     420

gcgccccgct ccgcctcacc tgccaccagg gagtgggcgg gcattgttcg ccgccgccgc     480

cgccgcgcgg gccatggggg ccgcccggcg cccggggccg ggctggcgag gcgccgcgcc     540

gccgctgaga cgggccccgc gcgcagcccg gcggcgcagg taaggccggc cgcgccatgg     600

tggacccggt gggcttcgcg gaggcgtgga aggcgcagtt cccggactca gagcccccgc     660

gcatggagct gcgctcagtg ggcgacatcg agcaggagct ggagcgctgc aaggcctcca     720

ttcggcgcct ggagcaggag gtgaaccagg agcgcttccg catgatctac ctgcagacgt     780

tgctggccaa ggaaaagaag agctatgacc ggcagcgatg gggcttccgg cgcgcggcgc     840

aggcccccga cggcgcctcc gagccccgag cgtccgcgtc gcgcccgcag ccagcgcccg     900

ccgacggagc cgacccgccg cccgccgagg agcccgaggc ccggcccgac ggcgagggtt     960

ctccgggtaa ggccaggccc gggaccgccc gcaggcccgg ggcagccgcg tcgggggaac    1020

gggacgaccg gggacccccc gccagcgtgg cggcgctcag gtccaacttc gagcggatcc    1080

gcaagggcca tggccagccc ggggcggacg ccgagaagcc cttctacgtg aacgtcgagt    1140

ttcaccacga gcgcggcctg gtgaaggtca acgacaaaga ggtgtcggac cgcatcagct    1200

ccctgggcag ccaggccatg cagatggagc gcaaaaagtc ccagcacggc gcgggctcga    1260

gcgtggggga tgcatccagg ccccccttacc ggggacgctc ctcggagagc agctgcggcg    1320

tcgacggcga ctacgaggac gccgagttga acccccgctt cctgaaggac aacctgatcg    1380

acgccaatgg cggtagcagg ccccccttggc cgcccctgga gtaccagccc taccagagca    1440

tctacgtcgg gggcatgatg gaaggggagg gcaagggccc gctcctgcgc agccagagca    1500

cctctgagca ggagaagcgc cttacctggc cccgcaggtc ctactccccc cggagttttg    1560

aggattgcgg aggcggctat accccggact gcagctccaa tgagaacctc acctccagcg    1620

aggaggactt ctcctctggc cagtccagcc gcgtgtcccc aagccccacc acctaccgca    1680

tgttccggga caaaagccgc tctccctcgc agaactcgca acagtccttc gacagcagca    1740

gtccccccac gccgcagtgc cataagcggc accggcactg cccggttgtc gtgtccgagg    1800

ccaccatcgt gggcgtccgc aagaccgggc agatctggcc caacgatggc gagggcgcct    1860
```

```
tccatggaga cgcagaagcc cttcagcggc cagtagcatc tgactttgag cctcagggtc   1920
tgagtgaagc cgctcgttgg aactccaagg aaaaccttct cgctggaccc agtgaaaatg   1980
accccaacct tttcgttgca ctgtatgatt ttgtggccag tggagataac actctaagca   2040
taactaaagg tgaaaagctc cgggtcttag gctataatca caatggggaa tggtgtgaag   2100
cccaaaccaa aaatggccaa ggctgggtcc caagcaacta catcacgcca gtcaacagtc   2160
tggagaaaca ctcctggtac catgggcctg tgtcccgcaa tgccgctgag tatctgctga   2220
gcagcgggat caatggcagc ttcttggtgc gtgagagtga gagcagtcct ggccagaggt   2280
ccatctcgct gagatacgaa gggagggtgt accattacag gatcaacact gcttctgatg   2340
gcaagctcta cgtctcctcc gagagccgct tcaacaccct ggccgagttg gttcatcatc   2400
attcaacggt ggccgacggg ctcatcacca cgctccatta tccagcccca aagcgcaaca   2460
agcccactgt ctatggtgtg tcccccaact acgacaagtg ggagatggaa cgcacggaca   2520
tcaccatgaa gcacaagctg ggcgggggcc agtacgggga ggtgtacgag ggcgtgtgga   2580
agaaatacag cctgacggtg gccgtgaaga ccttgaagga ggacaccatg gaggtggaag   2640
agttcttgaa agaagctgca gtcatgaaag agatcaaaca ccctaacctg gtgcagctcc   2700
ttggggtctg cacccgggag cccccgttct atatcatcac tgagttcatg acctacggga   2760
acctcctgga ctacctgagg gagtgcaacc ggcaggaggt gaacgccgtg gtgctgctgt   2820
acatggccac tcagatctcg tcagccatgg agtacctgga gaagaaaaac ttcatccaca   2880
gagatcttgc tgcccgaaac tgcctggtag gggagaacca cttggtgaag gtagctgatt   2940
ttggcctgag caggttgatg acaggggaca cctacacagc ccatgctgga gccaagttcc   3000
ccatcaaatg gactgcaccc gagagcctgg cctacaacaa gttctccatc aagtccgacg   3060
tctgggcatt tggagtattg ctttgggaaa ttgctaccta tggcatgtcc ccttacccgg   3120
gaattgacct gtcccaggtg tatgagctgc tagagaagga ctaccgcatg gagcgcccag   3180
aaggctgccc agagaaggtc tatgaactca tgcgagcatg ttggcagtgg aatccctctg   3240
accggccctc ctttgctgaa atccaccaag cctttgaaac aatgttccag gaatccagta   3300
tctcagacga agtggaaaag gagctgggga aacaaggcgt ccgtggggct gtgagtacct   3360
tgctgcaggc cccagagctg cccaccaaga cgaggacctc caggagagct gcagagcaca   3420
gagacaccac tgacgtgcct gagatgcctc actccaaggg ccagggagag agcgatcctc   3480
tggaccatga gcctgccgtg tctccattgc tccctcgaaa agagcgaggt cccccggagg   3540
gcggcctgaa tgaagatgag cgccttctcc ccaaagacaa aaagaccaac ttgttcagcg   3600
ccttgatcaa gaagaagaag aagacagccc caacccctcc caaacgcagc agctccttcc   3660
gggagatgga cggccagccg gagcgcagag ggcgcggcga ggaagagggc cgagacatca   3720
gcaacggggc actggctttc acccccttgg acacagctga cccagccaag tccccaaagc   3780
ccagcaatgg ggctggggtc cccaatggag ccctccggga gtccgggggc tcaggcttcc   3840
ggtctcccca cctgtggaag aagtccagca cgctgaccag cagccgccta gccaccggcg   3900
aggaggaggg cggtggcagc tccagcaagc gcttcctgcg ctcttgctcc gcctcctgcg   3960
ttccccatgg ggccaaggac acggagtgga ggtcagtcac gctgcctcgg gacttgcagt   4020
ccacgggaag acagtttgac tcgtccacat ttggagggca caaaagtgag aagccggctc   4080
tgcctcggaa gagggcaggg gagaacaggt ctgaccaggt gacccgaggc acagtaacgc   4140
ctcccccag gctggtgaaa aagaatgagg aagctgctga tgaggtcttc aaagacatca   4200
```

-continued

```
tggagtccag cccgggctcc agcccgccca acctgactcc aaaacccctc cggcggcagg   4260
tcaccgtggc cctgcctcg ggcctccccc acaaggaaga agctggaaag ggcagtgcct   4320
tagggacccc tgctgcagct gagccagtga cccccaccag caaagcaggc tcaggtgcac   4380
cagggggcac cagcaagggc cccgccgagg agtccagagt gaggaggcac aagcactcct   4440
ctgagtcgcc agggagggac aaggggaaat tgtccaggct caaacctgcc ccgccgcccc   4500
caccagcagc ctctgcaggg aaggctggag gaaagccctc gcagagcccg agccaggagg   4560
cggccgggga ggcagtcctg ggcgcaaaga caaaagccac gagtctggtt gatgctgtga   4620
acagtgacgc tgccaagccc agccagccgg gagagggcct caaaaagccc gtgctcccgg   4680
ccactccaaa gccacagtcc gccaagccgt cggggacccc catcagccca gcccccgttc   4740
cctccacgtt gccatcagca tcctcggccc tggcagggga ccagccgtct tccaccgcct   4800
tcatccctct catatcaacc cgagtgtctc ttcggaaaac ccgccagcct ccagagcgga   4860
tcgccagcgg cgccatcacc aagggcgtgg tcctggacag caccgaggcg ctgtgcctcg   4920
ccatctctag gaactccgag cagatggcca gccacagcgc agtgctggag gccggcaaaa   4980
acctctacac gttctgcgtg agctatgtgg attccatcca gcaaatgagg aacaagtttg   5040
ccttccgaga ggccatcaac aaactggaga ataatctccg ggagcttcag atctgcccgg   5100
cgacagcagg cagtggtcca gcggccactc aggacttcag caagctcctc agttcggtga   5160
aggaaatcag tgacatagtg cagaggtagc agcagtcagg ggtcaggtgt caggcccgtc   5220
ggagctgcct gcagcacatg cgggctcgcc catacccgtg acagtggctg acaagggact   5280
agtgagtcag caccttggcc caggagctct gcgccaggca gagctgaggg ccctgtggag   5340
tccagctcta ctacctacgt ttgcaccgcc tgccctcccg caccttcctc ctccccgctc   5400
cgtctctgtc ctcgaatttt atctgtggag ttcctgctcc gtggactgca gtcggcatgc   5460
caggacccgc cagccccgct cccacctagt gccccagact gagctctcca ggccaggtgg   5520
gaacggctga tgtggactgt ctttttcatt tttttctctc tggagcccct cctcccccgg   5580
ctgggcctcc ttcttccact tctccaagaa tggaagcctg aactgaggcc ttgtgtgtca   5640
ggccctctgc ctgcactccc tggccttgcc cgtcgtgtgc tgaagacatg tttcaagaac   5700
cgcatttcgg gaagggcatg cacgggcatg cacacggctg gtcactctgc cctctgctgc   5760
tgcccggggt ggggtgcact cgccatttcc tcacgtgcag gacagctctt gatttgggtg   5820
gaaaacaggg tgctaaagcc aaccagcctt tgggtcctgg gcaggtggga gctgaaaagg   5880
atcgaggcat ggggcatgtc ctttccatct gtccacatcc ccagagccca gctcttgctc   5940
tcttgtgacg tgcactgtga atcctggcaa gaaagcttga gtctcaaggg tggcaggtca   6000
ctgtcactgc cgacatccct cccccagcag aatggaggca ggggacaagg gaggcagtgg   6060
ctagtggggt gaacagctgg tgccaaatag ccccagactg ggcccaggca ggtctgcaag   6120
ggcccagagt gaaccgtcct ttcacacatc tgggtgccct gaaagggccc ttcccctccc   6180
ccactcctct aagacaaagt agattcttac aaggcccttt cctttggaac aagacagcct   6240
tcacttttct gagttcttga agcatttcaa agccctgcct ctgtgtagcc gccctgagag   6300
agaatagagc tgccactggg cacctgcgca caggtgggag gaaagggcct ggccagtcct   6360
ggtcctggct gcactcttga actgggcgaa tgtcttattt aattaccgtg agtgacatag   6420
cctcatgttc tgtgggggtc atcagggagg gttaggaaaa ccacaaacgg agcccctgaa   6480
agcctcacgt atttcacaga gcacgcctgc catcttctcc ccgaggctgc cccaggccgg   6540
agcccagata cgggggctgt gactctgggc agggacccgg ggtctcctgg accttgacag   6600
```

agcagctaac tccgagagca gtgggcaggt ggccgcccct gaggcttcac gccgggagaa 6660
gccaccttcc cacccttca taccgcctcg tgccagcagc ctcgcacagg ccctagcttt 6720
acgctcatca cctaaacttg tactttattt ttctgataga aatggtttcc tctggatcgt 6780
tttatgcggt tcttacagca catcacctct ttgcccccga cggctgtgac gcagccggag 6840
ggaggcacta gtcaccgaca gcggccttga agacagagca aagcgcccac ccaggtcccc 6900
cgactgcctg tctccatgag gtactggtcc cttccttttg ttaacgtgat gtgccactat 6960
attttacacg tatctcttgg tatgcatctt ttatagacgc tcttttctaa gtggcgtgtg 7020
catagcgtcc tgccctgccc cctcggggc ctgtggtggc tccccctctg cttctcgggg 7080
tccagtgcat tttgtttctg tatatgattc tctgtggttt tttttgaatc caaatctgtc 7140
ctctgtagta ttttttaaat aaatcagtgt ttacattaga aaaaaaaaaa aaaaaaaaaa 7200

<210> SEQ ID NO 2
<211> LENGTH: 8628
<212> TYPE: DNA
<213> ORGANISM: Homo sapiens

<400> SEQUENCE: 2 gggggggaggg tggcggctcg atgggggagc cgcctccagg gggccccccc gccctgtgcc 60
cacggcgcgg ccccttaag aggcccgcct ggctccgtca tccgcgccgc ggccacctcc 120
ccccggccct cccccttcctg cggcgcagag tgcgggccgg gcgggagtgc ggcgagagcc 180
ggctggctga gcttagcgtc cgaggaggcg gcggcggcgg cggcggcacg gcggcggcgg 240
ggctgtgggg cggtgcggaa gcgagaggcg aggagcgcgc gggccgtggc cagagtctgg 300
cggcggcctg gcggagcgga gagcagcgcc cgcgcctcgc cgtgcggagg agccccgcac 360
acaatagcgg cgcgcgcagc ccgcgccctt ccccccggcg cgccccgccc cgcgcgccga 420
gcgccccgct ccgcctcacc tgccaccagg gagtgggcgg gcattgttcg ccgccgccgc 480
cgccgcgcgg gccatggggg ccgcccggcg cccggggccg ggctggcgag gcgccgcgcc 540
gccgctgaga cgggccccgc gcgcagcccg gcggcgcagg taaggccggc cgcgccatgg 600
tggacccggt gggcttcgcg gaggcgtgga aggcgcagtt cccggactca gagcccccgc 660
gcatggagct gcgctcagtg ggcgacatcg agcaggagct ggagcgctgc aaggcctcca 720
ttcggcgcct ggagcaggag gtgaaccagg agcgcttccg catgatctac ctgcagacgt 780
tgctggccaa ggaaaagaag agctatgacc ggcagcgatg ggcttccgg cgcgcggcgc 840 aggcccccga cggcgcctcc gagccccgag cgtccgcgtc gcgcccgcag ccagcgcccg 900
ccgacggagc cgacccgccg cccgccgagg agcccgaggc ccggcccgac ggcgagggtt 960
ctccgggtaa ggccaggccc gggaccgccc gcaggcccgg ggcagccgcg tcgggggaac 1020
gggacgaccg gggacccccc gccagcgtgg cggcgctcag gtccaacttc gagcggatcc 1080
gcaagggcca tggccagccc ggggcggacg ccgagaagcc cttctacgtg aacgtcgagt 1140
ttcaccacga gcgcggcctg gtgaaggtca acgacaaaga ggtgtcggac cgcatcagct 1200
ccctgggcag ccaggccatg cagatggagc gcaaaaagtc ccagcacggc gcgggctcga 1260
gcgtggggga tgcatccagg cccccttacc ggggacgctc ctcggagagc agctgcggcg 1320
tcgacggcga ctacgaggac gccgagttga acccccgctt cctgaaggac aacctgatcg 1380
acgccaatgg cggtagcagg ccccccttggc cgcccctgga gtaccagccc taccagagca 1440
tctacgtcgg gggcatgatg gaaggggagg gcaagggccc gctcctgcgc agccagagca 1500

```
cctctgagca ggagaagcgc cttacctggc cccgcaggtc ctactccccc cggagttttg   1560
aggattgcgg aggcggctat accccggact gcagctccaa tgagaacctc acctccagcg   1620
aggaggactt ctcctctggc cagtccagcc gcgtgtcccc aagccccacc acctaccgca   1680
tgttccggga caaaagccgc tctccctcgc agaactcgca acagtccttc gacagcagca   1740
gtccccccac gccgcagtgc cataagcggc accggcactg cccggttgtc gtgtccgagg   1800
ccaccatcgt gggcgtccgc aagaccgggc agatctggcc caacgatggc gagggcgcct   1860
tccatggaga cgcagatggc tcgttcggaa caccacctgg atacggctgc gctgcagacc   1920
gggcagagga gcagcgccgg caccaagatg ggctgcccta cattgatgac tcgccctcct   1980
catcgcccca cctcagcagc aagggcaggg gcagccggga tgcgctggtc tcgggagccc   2040
tggagtccac taaagcgagt gagctggact tggaaaaggg cttggagatg agaaaatggg   2100
tcctgtcggg aatcctggct agcgaggaga cttacctgag ccacctggag gcactgctgc   2160
tgcccatgaa gcctttgaaa gccgctgcca ccacctctca gccggtgctg acgagtcagc   2220
agatcgagac catcttcttc aaagtgcctg agctctacga gatccacaag gagttctatg   2280
atgggctctt cccccgcgtg cagcagtgga gccaccagca gcgggtgggc gacctcttcc   2340
agaagctggc cagccagctg ggtgtgtacc gggccttcgt ggacaactac ggagttgcca   2400
tggaaatggc tgagaagtgc tgtcaggcca atgctcagtt tgcagaaatc tccgagaacc   2460
tgagagccag aagcaacaaa gatgccaagg atccaacgac caagaactct ctggaaactc   2520
tgctctacaa gcctgtggac cgtgtgacga ggagcacgct ggtcctccat gacttgctga   2580
agcacactcc tgccagccac cctgaccacc ccttgctgca ggacgccctc cgcatctcac   2640
agaacttcct gtccagcatc aatgaggaga tcacaccccg acggcagtcc atgacggtga   2700
agaagggaga gcaccggcag ctgctgaagg acagcttcat ggtggagctg gtggaggggg   2760
cccgcaagct gcgccacgtc ttcctgttca ccgacctgct tctctgcacc aagctcaaga   2820
agcagagcgg aggcaaaacg cagcagtatg actgcaaatg gtacattccg ctcacggatc   2880
tcagcttcca gatggtggat gaactggagg cagtgcccaa catcccccctg gtgcccgatg   2940
aggagctgga cgctttgaag atcaagatct cccagatcaa gaatgacatc cagagagaga   3000
agagggcgaa caagggcagc aaggctacgg agaggctgaa gaagaagctg tcggagcagg   3060
agtcactgct gctgcttatg tctcccagca tggccttcag ggtgcacagc cgcaacggca   3120
agagttacac gttcctgatc tcctctgact atgagcgtgc agagtggagg gagaacatcc   3180
gggagcagca gaagaagtgt ttcagaagct tctccctgac atccgtggag ctgcagatgc   3240
tgaccaactc gtgtgtgaaa ctccagactg tccacagcat tccgctgacc atcaataagg   3300
aagaagccct tcagcggcca gtagcatctg actttgagcc tcagggtctg agtgaagccg   3360
ctcgttggaa ctccaaggaa aaccttctcg ctggacccag tgaaaatgac cccaaccttt   3420
tcgttgcact gtatgatttt gtggccagtg gagataacac tctaagcata actaaaggtg   3480
aaaagctccg ggtcttaggc tataatcaca atggggaatg gtgtgaagcc caaaccaaaa   3540
atggccaagg ctgggtccca agcaactaca tcacgccagt caacagtctg gagaaacact   3600
cctggtacca tgggcctgtg tcccgcaatg ccgctgagta tctgctgagc agcgggatca   3660
atggcagctt cttggtgcgt gagagtgaga gcagtcctgg ccagaggtcc atctcgctga   3720
gatacgaagg gagggtgtac cattacagga tcaacactgc ttctgatggc aagctctacg   3780
tctcctccga gagccgcttc aacaccctgg ccgagttggt tcatcatcat tcaacggtgg   3840
ccgacgggct catcaccacg ctccattatc cagccccaaa gcgcaacaag cccactgtct   3900
```

```
atggtgtgtc ccccaactac gacaagtggg agatggaacg cacggacatc accatgaagc   3960
acaagctggg cgggggccag tacggggagg tgtacgaggg cgtgtggaag aaatacagcc   4020
tgacggtggc cgtgaagacc ttgaaggagg acaccatgga ggtggaagag ttcttgaaag   4080
aagctgcagt catgaaagag atcaaacacc ctaacctggt gcagctcctt ggggtctgca   4140
cccgggagcc cccgttctat atcatcactg agttcatgac ctacgggaac ctcctggact   4200
acctgaggga gtgcaaccgg caggaggtga acgccgtggt gctgctgtac atggccactc   4260
agatctcgtc agccatggag tacctggaga agaaaaactt catccacaga gatcttgctg   4320
cccgaaactg cctggtaggg gagaaccact tggtgaaggt agctgatttt ggcctgagca   4380
ggttgatgac aggggacacc tacacagccc atgctggagc caagttcccc atcaaatgga   4440
ctgcacccga gagcctggcc tacaacaagt tctccatcaa gtccgacgtc tgggcatttg   4500
gagtattgct ttgggaaatt gctacctatg gcatgtcccc ttacccggga attgacctgt   4560
cccaggtgta tgagctgcta gagaaggact accgcatgga gcgcccagaa ggctgcccag   4620
agaaggtcta tgaactcatg cgagcatgtt ggcagtggaa tccctctgac cggccctcct   4680
ttgctgaaat ccaccaagcc tttgaaacaa tgttccagga atccagtatc tcagacgaag   4740
tggaaaagga gctggggaaa caaggcgtcc gtggggctgt gagtaccttg ctgcaggccc   4800
cagagctgcc caccaagacg aggacctcca ggagagctgc agagcacaga gacaccactg   4860
acgtgcctga gatgcctcac tccaagggcc agggagagag cgatcctctg gaccatgagc   4920
ctgccgtgtc tccattgctc cctcgaaaag agcgaggtcc cccggagggc ggcctgaatg   4980
aagatgagcg ccttctcccc aaagacaaaa agaccaactt gttcagcgcc ttgatcaaga   5040
agaagaagaa gacagcccca acccctccca aacgcagcag ctccttccgg gagatggacg   5100
gccagccgga gcgcagaggg gccggcgagg aagagggccg agacatcagc aacggggcac   5160
tggctttcac cccccttggac acagctgacc cagccaagtc ccccaaagccc agcaatgggg   5220
ctggggtccc caatggagcc ctccgggagt ccgggggctc aggcttccgg tctccccacc   5280
tgtggaagaa gtccagcacg ctgaccagca gccgcctagc caccggcgag gaggagggcg   5340
gtggcagctc cagcaagcgc ttcctgcgct cttgctccgc ctcctgcgtt ccccatgggg   5400
ccaaggacac ggagtggagg tcagtcacgc tgcctcggga cttgcagtcc acgggaagac   5460
agtttgactc gtccacattt ggagggcaca aaagtgagaa gccggctctg cctcggaaga   5520
gggcagggga gaacaggtct gaccaggtga cccgaggcac agtaacgcct ccccccaggc   5580
tggtgaaaaa gaatgaggaa gctgctgatg aggtcttcaa agacatcatg gagtccagcc   5640
cgggctccag cccgcccaac ctgactccaa aacccctccg gcggcaggtc accgtggccc   5700
ctgcctcggg cctcccccac aaggaagaag ctggaaaggg cagtgcctta gggacccctg   5760
ctgcagctga gccagtgacc cccaccagca aagcaggctc aggtgcacca gggggcacca   5820
gcaagggccc cgccgaggag tccagagtga ggaggcacaa gcactcctct gagtcgccag   5880
ggagggacaa ggggaaattg tccaggctca aacctgcccc gccgccccca ccagcagcct   5940
ctgcagggaa ggctggagga aagccctcgc agagcccgag ccaggaggcg gccggggagg   6000
cagtcctggg cgcaaagaca aaagccacga gtctggttga tgctgtgaac agtgacgctg   6060
ccaagcccag ccagccggga gagggcctca aaaagcccgt gctcccggcc actccaaagc   6120
cacagtccgc caagccgtcg gggaccccca tcagcccagc cccegttccc tccacgttgc   6180
catcagcatc ctcggccctg gcaggggacc agccgtcttc caccgccttc atccctctca   6240
```

```
tatcaacccg agtgtctctt cggaaaaccc gccagcctcc agagcggatc gccagcggcg   6300
ccatcaccaa gggcgtggtc ctggacagca ccgaggcgct gtgcctcgcc atctctagga   6360
actccgagca gatggccagc cacagcgcag tgctggaggc cggcaaaaac ctctacacgt   6420
tctgcgtgag ctatgtggat tccatccagc aaatgaggaa caagtttgcc ttccgagagg   6480
ccatcaacaa actggagaat aatctccggg agcttcagat ctgcccggcg acagcaggca   6540
gtggtccagc ggccactcag gacttcagca agctcctcag ttcggtgaag gaaatcagtg   6600
acatagtgca gaggtagcag cagtcagggg tcaggtgtca ggcccgtcgg agctgcctgc   6660
agcacatgcg ggctcgccca tacccgtgac agtggctgac aagggactag tgagtcagca   6720
ccttggccca ggagctctgc gccaggcaga gctgagggcc ctgtggagtc cagctctact   6780
acctacgttt gcaccgcctg ccctcccgca ccttcctcct ccccgctccg tctctgtcct   6840
cgaattttat ctgtggagtt cctgctccgt ggactgcagt cggcatgcca ggacccgcca   6900
gccccgctcc cacctagtgc cccagactga gctctccagg ccaggtggga acggctgatg   6960
tggactgtct ttttcatttt tttctctctg gagcccctcc tcccccggct gggcctcctt   7020
cttccacttc tccaagaatg gaagcctgaa ctgaggcctt gtgtgtcagg ccctctgcct   7080
gcactccctg gccttgcccg tcgtgtgctg aagacatgtt tcaagaaccg catttcggga   7140
agggcatgca cgggcatgca cacggctggt cactctgccc tctgctgctg cccggggtgg   7200
ggtgcactcg ccatttcctc acgtgcagga cagctcttga tttgggtgga aaacagggtg   7260
ctaaagccaa ccagcctttg ggtcctgggc aggtgggagc tgaaaaggat cgaggcatgg   7320
ggcatgtcct ttccatctgt ccacatcccc agagcccagc tcttgctctc ttgtgacgtg   7380
cactgtgaat cctggcaaga aagcttgagt ctcaagggtg gcaggtcact gtcactgccg   7440
acatccctcc cccagcagaa tggaggcagg ggacaaggga ggcagtggct agtggggtga   7500
acagctggtg ccaaatagcc ccagactggg cccaggcagg tctgcaaggg cccagagtga   7560
accgtccttt cacacatctg ggtgccctga aagggccctt cccctccccc actcctctaa   7620
gacaaagtag attcttacaa ggccctttcc tttggaacaa gacagccttc acttttctga   7680
gttcttgaag catttcaaag ccctgcctct gtgtagccgc cctgagagag aatagagctg   7740
ccactgggca cctgcgcaca ggtgggagga aagggcctgg ccagtcctgg tcctggctgc   7800
actcttgaac tgggcgaatg tcttatttaa ttaccgtgag tgacatagcc tcatgttctg   7860
tgggggtcat cagggagggt taggaaaacc acaaacggag cccctgaaag cctcacgtat   7920
ttcacagagc acgcctgcca tcttctcccc gaggctgccc caggccggag cccagatacg   7980
ggggctgtga ctctgggcag ggacccgggg tctcctggac cttgacagag cagctaactc   8040
cgagagcagt gggcaggtgg ccgcccctga ggcttcacgc cgggagaagc caccttccca   8100
ccccttcata ccgcctcgtg ccagcagcct cgcacaggcc ctagctttac gctcatcacc   8160
taaacttgta ctttattttt ctgatagaaa tggtttcctc tggatcgttt tatgcggttc   8220
ttacagcaca tcacctcttt gcccccgacg gctgtgacgc agccggaggg aggcactagt   8280
caccgacagc ggccttgaag acagagcaaa gcgcccaccc aggtcccccg actgcctgtc   8340
tccatgaggt actggtccct tccttttgtt aacgtgatgt gccactatat tttacacgta   8400
tctcttggta tgcatctttt atagacgctc ttttctaagt ggcgtgtgca tagcgtcctg   8460
ccctgccccc tcgggggcct gtggtggctc cccctctgct tctcggggtc cagtgcattt   8520
tgtttctgta tatgattctc tgtggttttt tttgaatcca aatctgtcct ctgtagtatt   8580
ttttaaataa atcagtgttt acattagaaa aaaaaaaaaa aaaaaaaa                8628
```

<210> SEQ ID NO 3
<211> LENGTH: 8703
<212> TYPE: DNA
<213> ORGANISM: Homo sapiens

<400> SEQUENCE: 3

```
gggggaggg tggcggctcg atgggggagc cgcctccagg gggccccccc gccctgtgcc     60
cacggcgcgg cccctttaag aggcccgcct ggctccgtca tccgcgccgc ggccacctcc    120
ccccggccct ccccttcctg cggcgcagag tgcgggccgg gcgggagtgc ggcgagagcc    180
ggctggctga gcttagcgtc cgaggaggcg gcggcggcgg cggcggcacg gcggcggcgg    240
ggctgtgggg cggtgcggaa gcgagaggcg aggagcgcgc gggccgtggc cagagtctgg    300
cggcggcctg gcggagcgga gagcagcgcc cgcgcctcgc cgtgcggagg agccccgcac    360
acaatagcgg cgcgcgcagc ccgcgccctt ccccccggcg cgccccgccc cgcgcgccga    420
gcgccccgct ccgcctcacc tgccaccagg gagtgggcgg gcattgttcg ccgccgccgc    480
cgccgcgcgg gccatggggg ccgcccggcg cccggggccg ggctggcgag gcgccgcgcc    540
gccgctgaga cgggccccgc gcgcagcccg gcggcgcagg taaggccggc cgcgccatgg    600
tggacccggt gggcttcgcg gaggcgtgga aggcgcagtt cccggactca gagcccccgc    660
gcatggagct gcgctcagtg ggcgacatcg agcaggagct ggagcgctgc aaggcctcca    720
ttcggcgcct ggagcaggag gtgaaccagg agcgcttccg catgatctac ctgcagacgt    780
tgctggccaa ggaaaagaag agctatgacc ggcagcgatg gggcttccgg cgcgcggcgc    840
aggcccccga cggcgcctcc gagccccgag cgtccgcgtc gcgcccgcag ccagcgcccg    900
ccgacggagc cgacccgccg cccgccgagg agcccgaggc ccggcccgac ggcgagggtt    960
ctccgggtaa ggccaggccc gggaccgccc gcaggcccgg ggcagccgcg tcgggggaac   1020
gggacgaccg gggacccccc gccagcgtgg cggcgctcag gtccaacttc gagcggatcc   1080
gcaagggcca tggccagccc ggggcggacg ccgagaagcc cttctacgtg aacgtcgagt   1140
ttcaccacga gcgcggcctg gtgaaggtca acgacaaaga ggtgtcggac cgcatcagct   1200
ccctgggcag ccaggccatg cagatggagc gcaaaaagtc ccagcacggc gcgggctcga   1260
gcgtggggga tgcatccagg ccccccttacc ggggacgctc ctcggagagc agctgcggcg   1320
tcgacggcga ctacgaggac gccgagttga acccccgctt cctgaaggac aacctgatcg   1380
acgccaatgg cggtagcagg ccccccttggc cgcccctgga gtaccagccc taccagagca   1440
tctacgtcgg gggcatgatg gaaggggagg gcaagggccc gctcctgcgc agccagagca   1500
cctctgagca ggagaagcgc cttacctggc cccgcaggtc ctactccccc cggagttttg   1560
aggattgcgg aggcggctat accccggact gcagctccaa tgagaacctc acctccagcg   1620
aggaggactt ctcctctggc cagtccagcc gcgtgtcccc aagccccacc acctaccgca   1680
tgttccggga caaaagccgc tctccctcgc agaactcgca acagtccttc gacagcagca   1740
gtccccccac gccgcagtgc cataagcggc accggcactg cccggttgtc gtgtccgagg   1800
ccaccatcgt gggcgtccgc aagaccgggc agatctggcc caacgatggc gagggcgcct   1860
tccatggaga cgcagatggc tcgttcggaa caccacctgg atacggctgc gctgcagacc   1920
gggcagagga gcagcgccgg caccaagatg ggctgcccta cattgatgac tcgccctcct   1980
catcgcccca cctcagcagc aagggcaggg gcagccggga tgcgctggtc tcgggagccc   2040
tggagtccac taaagcgagt gagctggact tggaaaaggg cttggagatg agaaaatggg   2100
```

-continued tcctgtcggg aatcctggct agcgaggaga cttacctgag ccacctggag gcactgctgc 2160
tgcccatgaa gcctttgaaa gccgctgcca ccacctctca gccggtgctg acgagtcagc 2220
agatcgagac catcttcttc aaagtgcctg agctctacga gatccacaag gagttctatg 2280
atgggctctt cccccgcgtg cagcagtgga gccaccagca gcgggtgggc gacctcttcc 2340
agaagctggc cagccagctg ggtgtgtacc gggccttcgt ggacaactac ggagttgcca 2400
tggaaatggc tgagaagtgc tgtcaggcca atgctcagtt tgcagaaatc tccgagaacc 2460
tgagagccag aagcaacaaa gatgccaagg atccaacgac caagaactct ctggaaactc 2520
tgctctacaa gcctgtggac cgtgtgacga ggagcacgct ggtcctccat gacttgctga 2580
agcacactcc tgccagccac cctgaccacc ccttgctgca ggacgccctc cgcatctcac 2640
agaacttcct gtccagcatc aatgaggaga tcacaccccg acggcagtcc atgacggtga 2700
agaagggaga gcaccggcag ctgctgaagg acagcttcat ggtggagctg gtggaggggg 2760
cccgcaagct gcgccacgtc ttcctgttca ccgacctgct tctctgcacc aagctcaaga 2820
agcagagcgg aggcaaaacg cagcagtatg actgcaaatg gtacattccg ctcacggatc 2880
tcagcttcca gatggtggat gaactggagg cagtgcccaa catccccctg gtgcccgatg 2940
aggagctgga cgctttgaag atcaagatct cccagatcaa gaatgacatc cagagagaga 3000
agagggcgaa caagggcagc aaggctacgg agaggctgaa gaagaagctg tcggagcagg 3060
agtcactgct gctgcttatg tctcccagca tggccttcag ggtgcacagc cgcaacggca 3120
agagttacac gttcctgatc tcctctgact atgagcgtgc agagtggagg gagaacatcc 3180
gggagcagca gaagaagtgt ttcagaagct tctccctgac atccgtggag ctgcagatgc 3240
tgaccaactc gtgtgtgaaa ctccagactg tccacagcat tccgctgacc atcaataagg 3300
aagatgatga gtctccgggg ctctatgggt ttctgaatgt catcgtccac tcagccactg 3360
gatttaagca gagttcaaaa gcccttcagc ggccagtagc atctgacttt gagcctcagg 3420
gtctgagtga agccgctcgt tggaactcca aggaaaacct tctcgctgga cccagtgaaa 3480
atgaccccaa ccttttcgtt gcactgtatg attttgtggc cagtggagat aacactctaa 3540
gcataactaa aggtgaaaag ctccgggtct taggctataa tcacaatggg gaatggtgtg 3600
aagcccaaac caaaaatggc caaggctggg tcccaagcaa ctacatcacg ccagtcaaca 3660
gtctggagaa acactcctgg taccatgggc ctgtgtcccg caatgccgct gagtatctgc 3720
tgagcagcgg gatcaatggc agcttcttgg tgcgtgagag tgagagcagt cctggccaga 3780
ggtccatctc gctgagatac gaagggaggg tgtaccatta caggatcaac actgcttctg 3840
atggcaagct ctacgtctcc tccgagagcc gcttcaacac cctggccgag ttggttcatc 3900
atcattcaac ggtggccgac gggctcatca ccacgctcca ttatccagcc ccaaagcgca 3960
acaagcccac tgtctatggt gtgtccccca actacgacaa gtgggagatg gaacgcacgg 4020
acatcaccat gaagcacaag ctgggcgggg gccagtacgg ggaggtgtac gagggcgtgt 4080
ggaagaaata cagcctgacg gtggccgtga agaccttgaa ggaggacacc atggaggtgg 4140
aagagttctt gaaagaagct gcagtcatga aagagatcaa acaccctaac ctggtgcagc 4200
tccttggggt ctgcacccgg gagcccccgt tctatatcat cactgagttc atgacctacg 4260
ggaacctcct ggactacctg agggagtgca accggcagga ggtgaacgcc gtggtgctgc 4320
tgtacatggc cactcagatc tcgtcagcca tggagtacct ggagaagaaa aacttcatcc 4380
acagagatct tgctgcccga aactgcctgg taggggagaa ccacttggtg aaggtagctg 4440
attttggcct gagcaggttg atgacagggg acacctacac agcccatgct ggagccaagt 4500

```
tccccatcaa atggactgca cccgagagcc tggcctacaa caagttctcc atcaagtccg   4560
acgtctgggc atttggagta ttgctttggg aaattgctac ctatggcatg tccccttacc   4620
cgggaattga cctgtcccag gtgtatgagc tgctagagaa ggactaccgc atggagcgcc   4680
cagaaggctg cccagagaag gtctatgaac tcatgcgagc atgttggcag tggaatccct   4740
ctgaccggcc ctcctttgct gaaatccacc aagcctttga aacaatgttc caggaatcca   4800
gtatctcaga cgaagtggaa aaggagctgg ggaaacaagg cgtccgtggg gctgtgagta   4860
ccttgctgca ggccccagag ctgcccacca agacgaggac ctccaggaga gctgcagagc   4920
acagagacac cactgacgtg cctgagatgc ctcactccaa gggccaggga gagagcgatc   4980
ctctggacca tgagcctgcc gtgtctccat tgctccctcg aaaagagcga ggtcccccgg   5040
agggcggcct gaatgaagat gagcgccttc tccccaaaga caaaaagacc aacttgttca   5100
gcgccttgat caagaagaag aagaagacag ccccaacccc tcccaaacgc agcagctcct   5160
tccgggagat ggacggccag ccggagcgca gaggggccgg cgaggaagag ggccgagaca   5220
tcagcaacgg ggcactggct ttcacccct tggacacagc tgacccagcc aagtccccaa   5280
agcccagcaa tggggctggg gtccccaatg gagccctccg ggagtccggg ggctcaggct   5340
tccggtctcc ccacctgtgg aagaagtcca gcacgctgac cagcagccgc ctagccaccg   5400
gcgaggagga gggcggtggc agctccagca agcgcttcct gcgctcttgc tccgcctcct   5460
gcgttcccca tggggccaag gacacggagt ggaggtcagt cacgctgcct cgggacttgc   5520
agtccacggg aagacagttt gactcgtcca catttggagg gcacaaaagt gagaagccgg   5580
ctctgcctcg gaagagggca ggggagaaca ggtctgacca ggtgacccga ggcacagtaa   5640
cgcctccccc caggctggtg aaaaagaatg aggaagctgc tgatgaggtc ttcaaagaca   5700
tcatggagtc cagcccgggc tccagcccgc ccaacctgac tccaaaaccc ctccggcggc   5760
aggtcaccgt ggcccctgcc tcgggcctcc cccacaagga agaagctgga aagggcagtg   5820
ccttagggac ccctgctgca gctgagccag tgacccccac cagcaaagca ggctcaggtg   5880
caccaggggg caccagcaag ggccccgccg aggagtccag agtgaggagg cacaagcact   5940
cctctgagtc gccagggagg gacaagggga aattgtccag gctcaaacct gccccgccgc   6000
ccccaccagc agcctctgca gggaaggctg gaggaaagcc ctcgcagagc ccgagccagg   6060
aggcggccgg ggaggcagtc ctgggcgcaa agacaaaagc cacgagtctg gttgatgctg   6120
tgaacagtga cgctgccaag cccagccagc cgggagaggg cctcaaaaag cccgtgctcc   6180
cggccactcc aaagccacag tccgccaagc cgtcggggac ccccatcagc ccagcccccg   6240
ttccctccac gttgccatca gcatcctcgg ccctggcagg ggaccagccg tcttccaccg   6300
ccttcatccc tctcatatca acccgagtgt ctcttcggaa aacccgccag cctccagagc   6360
ggatcgccag cggcgccatc accaagggcg tggtcctgga cagcaccgag gcgctgtgcc   6420
tcgccatctc taggaactcc gagcagatgg ccagccacag cgcagtgctg gaggccggca   6480
aaaacctcta cacgttctgc gtgagctatg tggattccat ccagcaaatg aggaacaagt   6540
ttgccttccg agaggccatc aacaaactgg agaataatct ccgggagctt cagatctgcc   6600
cggcgacagc aggcagtggt ccagcggcca ctcaggactt cagcaagctc ctcagttcgg   6660
tgaaggaaat cagtgacata gtgcagaggt agcagcagtc aggggtcagg tgtcaggccc   6720
gtcggagctg cctgcagcac atgcgggctc gcccataccc gtgacagtgg ctgacaaggg   6780
actagtgagt cagcaccttg gcccaggagc tctgcgccag gcagagctga gggccctgtg   6840
```

```
gagtccagct ctactaccta cgtttgcacc gcctgccctc ccgcaccttc ctcctccccg   6900

ctccgtctct gtcctcgaat tttatctgtg gagttcctgc tccgtggact gcagtcggca   6960

tgccaggacc cgccagcccc gctcccacct agtgccccag actgagctct ccaggccagg   7020

tgggaacggc tgatgtggac tgtctttttc atttttttct ctctggagcc cctcctcccc   7080

cggctgggcc tccttcttcc acttctccaa gaatggaagc ctgaactgag gccttgtgtg   7140

tcaggccctc tgcctgcact ccctggcctt gcccgtcgtg tgctgaagac atgtttcaag   7200

aaccgcattt cgggaagggc atgcacgggc atgcacacgg ctggtcactc tgccctctgc   7260

tgctgcccgg ggtggggtgc actcgccatt tcctcacgtg caggacagct cttgatttgg   7320

gtggaaaaca gggtgctaaa gccaaccagc ctttgggtcc tgggcaggtg ggagctgaaa   7380

aggatcgagg catggggcat gtcctttcca tctgtccaca tccccagagc ccagctcttg   7440

ctctcttgtg acgtgcactg tgaatcctgg caagaaagct tgagtctcaa gggtggcagg   7500

tcactgtcac tgccgacatc cctcccccag cagaatggag gcaggggaca agggaggcag   7560

tggctagtgg ggtgaacagc tggtgccaaa tagccccaga ctgggcccag gcaggtctgc   7620

aagggcccag agtgaaccgt cctttcacac atctgggtgc cctgaaaggg cccttcccct   7680

cccccactcc tctaagacaa agtagattct tacaaggccc tttcctttgg aacaagacag   7740

ccttcacttt tctgagttct tgaagcattt caaagccctg cctctgtgta gccgccctga   7800

gagagaatag agctgccact gggcacctgc gcacaggtgg gaggaaaggg cctggccagt   7860

cctggtcctg gctgcactct tgaactgggc gaatgtctta tttaattacc gtgagtgaca   7920

tagcctcatg ttctgtgggg gtcatcaggg agggttagga aaaccacaaa cggagcccct   7980

gaaagcctca cgtatttcac agagcacgcc tgccatcttc tccccgaggc tgccccaggc   8040

cggagcccag atacgggggc tgtgactctg ggcagggacc cggggtctcc tggaccttga   8100

cagagcagct aactccgaga gcagtgggca ggtggccgcc cctgaggctt cacgccggga   8160

gaagccacct tcccacccct tcataccgcc tcgtgccagc agcctcgcac aggccctagc   8220

tttacgctca tcacctaaac ttgtacttta tttttctgat agaaatggtt tcctctggat   8280

cgttttatgc ggttcttaca gcacatcacc tctttgcccc cgacggctgt gacgcagccg   8340

gagggaggca ctagtcaccg acagcggcct tgaagacaga gcaaagcgcc cacccaggtc   8400

ccccgactgc ctgtctccat gaggtactgg tcccttcctt ttgttaacgt gatgtgccac   8460

tatattttac acgtatctct tggtatgcat cttttataga cgctcttttc taagtggcgt   8520

gtgcatagcg tcctgccctg ccccctcggg ggcctgtggt ggctcccccct ctgcttctcg   8580

gggtccagtg cattttgttt ctgtatatga ttctctgtgg ttttttttga atccaaatct   8640

gtcctctgta gtatttttta aataaatcag tgtttacatt agaaaaaaaa aaaaaaaaaa   8700

aaa                                                                  8703
```

```
<210> SEQ ID NO 4
<211> LENGTH: 1503
<212> TYPE: DNA
<213> ORGANISM: Homo sapiens

<400> SEQUENCE: 4

atggctcgtt cggaacacca cctggatacg gctgcgctgc agaccgggca gaggagcagc     60

gccggcacca agatgggctg ccctacattg atgactcgcc ctcctcatcg ccccacctca    120

gcagcaaggg caggggcagc cgggatgcgc tggtctcggg agccctggag tccactaaag    180

cgagtgagct ggacttggaa aagggcttgg agatgagaaa atgggtcctg tcgggaatcc    240
```

tggctagcga ggagacttac ctgagccacc tggaggcact gctgctgccc atgaagcctt 300
tgaaagccgc tgccaccacc tctcagccgg tgctgacgag tcagcagatc gagaccatct 360
tcttcaaagt gcctgagctc tacgagatcc acaaggagtt ctatgatggg ctcttccccc 420
gcgtgcagca gtggagccac cagcagcggg tgggcgacct cttccagaag ctggccagcc 480
agctgggtgt gtaccgggcc ttcgtggaca actacggagt tgccatggaa atggctgaga 540
agtgctgtca ggccaatgct cagtttgcag aaatctccga gaacctgaga gccagaagca 600
acaaagatgc caaggatcca acgaccaaga actctctgga aactctgctc tacaagcctg 660
tggaccgtgt gacgaggagc acgctggtcc tccatgactt gctgaagcac actcctgcca 720
gccaccctga ccaccccttg ctgcaggacg ccctccgcat ctcacagaac ttcctgtcca 780
gcatcaatga ggagatcaca ccccgacggc agtccatgac ggtgaagaag ggagagcacc 840
ggcagctgct gaaggacagc ttcatggtgg agctggtgga gggggcccgc aagctgcgcc 900
acgtcttcct gttcaccgac ctgcttctct gcaccaagct caagaagcag agcggaggca 960
aaacgcagca gtatgactgc aaatggtaca ttccgctcac ggatctcagc ttccagatgg 1020
tggatgaact ggaggcagtg cccaacatcc ccctggtgcc cgatgaggag ctggacgctt 1080
tgaagatcaa gatctcccag atcaagaatg acatccagag agagaagagg gcgaacaagg 1140
gcagcaaggc tacggagagg ctgaagaaga agctgtcgga gcaggagtca ctgctgctgc 1200
ttatgtctcc cagcatggcc ttcagggtgc acagccgcaa cggcaagagt tacacgttcc 1260
tgatctcctc tgactatgag cgtgcagagt ggagggagaa catccgggag cagcagaaga 1320
agtgtttcag aagcttctcc ctgacatccg tggagctgca gatgctgacc aactcgtgtg 1380
tgaaactcca gactgtccac agcattccgc tgaccatcaa taaggaagat gatgagtctc 1440
cggggctcta tgggtttctg aatgtcatcg tccactcagc cactggattt aagcagagtt 1500
caa 1503

<210> SEQ ID NO 5
<211> LENGTH: 1428
<212> TYPE: DNA
<213> ORGANISM: Homo sapiens

<400> SEQUENCE: 5
atggctcgtt cggaacacca cctggatacg gctgcgctgc agaccgggca gaggagcagc 60
gccggcacca agatgggctg ccctacattg atgactcgcc ctcctcatcg ccccacctca 120
gcagcaaggg caggggcagc cgggatgcgc tggtctcggg agccctggag tccactaaag 180
cgagtgagct ggacttggaa aagggcttgg agatgagaaa atgggtcctg tcgggaatcc 240
tggctagcga ggagacttac ctgagccacc tggaggcact gctgctgccc atgaagcctt 300
tgaaagccgc tgccaccacc tctcagccgg tgctgacgag tcagcagatc gagaccatct 360
tcttcaaagt gcctgagctc tacgagatcc acaaggagtt ctatgatggg ctcttccccc 420
gcgtgcagca gtggagccac cagcagcggg tgggcgacct cttccagaag ctggccagcc 480
agctgggtgt gtaccgggcc ttcgtggaca actacggagt tgccatggaa atggctgaga 540
agtgctgtca ggccaatgct cagtttgcag aaatctccga gaacctgaga gccagaagca 600
acaaagatgc caaggatcca acgaccaaga actctctgga aactctgctc tacaagcctg 660
tggaccgtgt gacgaggagc acgctggtcc tccatgactt gctgaagcac actcctgcca 720
gccaccctga ccaccccttg ctgcaggacg ccctccgcat ctcacagaac ttcctgtcca 780

```
gcatcaatga ggagatcaca ccccgacggc agtccatgac ggtgaagaag ggagagcacc    840

ggcagctgct gaaggacagc ttcatggtgg agctggtgga gggggcccgc aagctgcgcc    900

acgtcttcct gttcaccgac ctgcttctct gcaccaagct caagaagcag agcggaggca    960

aaacgcagca gtatgactgc aaatggtaca ttccgctcac ggatctcagc ttccagatgg   1020

tggatgaact ggaggcagtg cccaacatcc ccctggtgcc cgatgaggag ctggacgctt   1080

tgaagatcaa gatctcccag atcaagaatg acatccagag agagaagagg gcgaacaagg   1140

gcagcaaggc tacggagagg ctgaagaaga agctgtcgga gcaggagtca ctgctgctgc   1200

ttatgtctcc cagcatggcc ttcagggtgc acagccgcaa cggcaagagt tacacgttcc   1260

tgatctcctc tgactatgag cgtgcagagt ggagggagaa catccgggag cagcagaaga   1320

agtgtttcag aagcttctcc ctgacatccg tggagctgca gatgctgacc aactcgtgtg   1380

tgaaactcca gactgtccac agcattccgc tgaccatcaa taaggaag                1428


<210> SEQ ID NO 6
<211> LENGTH: 181
<212> TYPE: DNA
<213> ORGANISM: Homo sapiens

<400> SEQUENCE: 6

agttacacgt tcctgatctc ctctgactat gagcgtgcag agtggaggga gaacatccgg     60

gagcagcaga agaagtgttt cagaagcttc tccctgacat ccgtggagct gcagatgctg    120

accaactcgt gtgtgaaact ccagactgtc cacagcattc cgctgaccat caataaggaa    180

g                                                                    181


<210> SEQ ID NO 7
<211> LENGTH: 105
<212> TYPE: DNA
<213> ORGANISM: Homo sapiens

<400> SEQUENCE: 7

gtttcagaag cttctccctg acatccgtgg agctgcagat gctgaccaac tcgtgtgtga     60

aactccagac tgtccacagc attccgctga ccatcaataa ggaag                    105


<210> SEQ ID NO 8
<211> LENGTH: 21
<212> TYPE: DNA
<213> ORGANISM: Homo sapiens

<400> SEQUENCE: 8

agggagaagc ttctgaaaca c                                               21


<210> SEQ ID NO 9
<211> LENGTH: 5325
<212> TYPE: DNA
<213> ORGANISM: Homo sapiens

<400> SEQUENCE: 9

aagcccttca gcggccagta gcatctgact ttgagcctca gggtctgagt gaagccgctc     60

gttggaactc caaggaaaac cttctcgctg gacccagtga aaatgacccc aacctttttcg   120

ttgcactgta tgattttgtg gccagtggag ataacactct aagcataact aaaggtgaaa    180

agctccgggt cttaggctat aatcacaatg gggaatggtg tgaagcccaa accaaaaatg    240

gccaaggctg ggtcccaagc aactacatca cgccagtcaa cagtctggag aaacactcct    300

ggtaccatgg gcctgtgtcc cgcaatgccg ctgagtatct gctgagcagc gggatcaatg    360
```

-continued

```
gcagcttctt ggtgcgtgag agtgagagca gtcctggcca gaggtccatc tcgctgagat    420
acgaagggag ggtgtaccat tacaggatca acactgcttc tgatggcaag ctctacgtct    480
cctccgagag ccgcttcaac accctggccg agttggttca tcatcattca acggtggccg    540
acgggctcat caccacgctc cattatccag ccccaaagcg caacaagccc actgtctatg    600
gtgtgtcccc caactacgac aagtgggaga tggaacgcac ggacatcacc atgaagcaca    660
agctgggcgg gggccagtac ggggaggtgt acgagggcgt gtggaagaaa tacagcctga    720
cggtggccgt gaagaccttg aaggaggaca ccatggaggt ggaagagttc ttgaaagaag    780
ctgcagtcat gaaagagatc aaacacccta acctggtgca gctccttggg gtctgcaccc    840
gggagccccc gttctatatc atcactgagt tcatgaccta cgggaacctc ctggactacc    900
tgagggagtg caaccggcag gaggtgaacg ccgtggtgct gctgtacatg gccactcaga    960
tctcgtcagc catggagtac ctggagaaga aaaacttcat ccacagagat cttgctgccc   1020
gaaactgcct ggtaggggag aaccacttgg tgaaggtagc tgattttggc ctgagcaggt   1080
tgatgacagg ggacacctac acagcccatg ctggagccaa gttccccatc aaatggactg   1140
cacccgagag cctggcctac aacaagttct ccatcaagtc cgacgtctgg gcatttggag   1200
tattgctttg ggaaattgct acctatggca tgtcccctta cccgggaatt gacctgtccc   1260
aggtgtatga gctgctagag aaggactacc gcatggagcg cccagaaggc tgcccagaga   1320
aggtctatga actcatgcga gcatgttggc agtggaatcc ctctgaccgg ccctcctttg   1380
ctgaaatcca ccaagccttt gaaacaatgt tccaggaatc cagtatctca gacgaagtgg   1440
aaaaggagct ggggaaacaa ggcgtccgtg gggctgtgag taccttgctg caggccccag   1500
agctgcccac caagacgagg acctccagga gagctgcaga gcacagagac accactgacg   1560
tgcctgagat gcctcactcc aagggccagg gagagagcga tcctctggac catgagcctg   1620
ccgtgtctcc attgctccct cgaaaagagc gaggtccccc ggagggcggc ctgaatgaag   1680
atgagcgcct tctccccaaa gacaaaaaga ccaacttgtt cagcgccttg atcaagaaga   1740
agaagaagac agccccaacc cctcccaaac gcagcagctc cttccgggag atggacggcc   1800
agccggagcg cagaggggcc ggcgaggaag agggccgaga catcagcaac ggggcactgg   1860
ctttcacccc cttggacaca gctgacccag ccaagtcccc aaagcccagc aatggggctg   1920
gggtccccaa tggagccctc cgggagtccg gggctcagg cttccggtct ccccacctgt   1980
ggaagaagtc cagcacgctg accagcagcc gcctagccac cggcgaggag gagggcggtg   2040
gcagctccag caagcgcttc ctgcgctctt gctccgcctc ctgcgttccc catggggcca   2100
aggacacgga gtggaggtca gtcacgctgc ctcgggactt gcagtccacg ggaagacagt   2160
ttgactcgtc cacatttgga gggcacaaaa gtgagaagcc ggctctgcct cggaagaggg   2220
caggggagaa caggtctgac caggtgaccc gaggcacagt aacgcctccc cccaggctgg   2280
tgaaaaagaa tgaggaagct gctgatgagg tcttcaaaga catcatggag tccagcccgg   2340
gctccagccc gcccaacctg actccaaaac ccctccggcg gcaggtcacc gtggcccctg   2400
cctcgggcct cccccacaag gaagaagctg gaaagggcag tgccttaggg acccctgctg   2460
cagctgagcc agtgaccccc accagcaaag caggctcagg tgcaccaggg ggcaccagca   2520
agggccccgc cgaggagtcc agagtgagga ggcacaagca ctcctctgag tcgccaggga   2580
gggacaaggg gaaattgtcc aggctcaaac ctgccccgcc gcccccacca gcagcctctg   2640
cagggaaggc tggaggaaag ccctcgcaga gcccgagcca ggaggcggcc ggggaggcag   2700
```

-continued

```
tcctgggcgc aaagacaaaa gccacgagtc tggttgatgc tgtgaacagt gacgctgcca   2760

agcccagcca gccgggagag ggcctcaaaa agcccgtgct cccggccact ccaaagccac   2820

agtccgccaa gccgtcgggg acccccatca gcccagcccc cgttccctcc acgttgccat   2880

cagcatcctc ggccctggca ggggaccagc cgtcttccac cgccttcatc cctctcatat   2940

caacccgagt gtctcttcgg aaaacccgcc agcctccaga gcggatcgcc agcggcgcca   3000

tcaccaaggg cgtggtcctg gacagcaccg aggcgctgtg cctcgccatc tctaggaact   3060

ccgagcagat ggccagccac agcgcagtgc tggaggccgg caaaaacctc tacacgttct   3120

gcgtgagcta tgtggattcc atccagcaaa tgaggaacaa gtttgccttc cgagaggcca   3180

tcaacaaact ggagaataat ctccgggagc ttcagatctg cccggcgaca gcaggcagtg   3240

gtccagcggc cactcaggac ttcagcaagc tcctcagttc ggtgaaggaa atcagtgaca   3300

tagtgcagag gtagcagcag tcaggggtca ggtgtcaggc ccgtcggagc tgcctgcagc   3360

acatgcgggc tcgcccatac ccgtgacagt ggctgacaag ggactagtga gtcagcacct   3420

tggcccagga gctctgcgcc aggcagagct gagggccctg tggagtccag ctctactacc   3480

tacgtttgca ccgcctgccc tcccgcacct tcctcctccc cgctccgtct ctgtcctcga   3540

attttatctg tggagttcct gctccgtgga ctgcagtcgg catgccagga cccgccagcc   3600

ccgctcccac ctagtgcccc agactgagct ctccaggcca ggtgggaacg gctgatgtgg   3660

actgtctttt tcattttttt ctctctggag cccctcctcc cccggctggg cctccttctt   3720

ccacttctcc aagaatggaa gcctgaactg aggccttgtg tgtcaggccc tctgcctgca   3780

ctccctggcc ttgcccgtcg tgtgctgaag acatgtttca agaaccgcat ttcgggaagg   3840

gcatgcacgg gcatgcacac ggctggtcac tctgccctct gctgctgccc ggggtggggt   3900

gcactcgcca tttcctcacg tgcaggacag ctcttgattt gggtggaaaa cagggtgcta   3960

aagccaacca gcctttgggt cctgggcagg tgggagctga aaaggatcga ggcatggggc   4020

atgtcctttc catctgtcca catccccaga gcccagctct tgctctcttg tgacgtgcac   4080

tgtgaatcct ggcaagaaag cttgagtctc aagggtggca ggtcactgtc actgccgaca   4140

tccctccccc agcagaatgg aggcagggga caagggaggc agtggctagt ggggtgaaca   4200

gctggtgcca aatagcccca gactgggccc aggcaggtct gcaagggccc agagtgaacc   4260

gtcctttcac acatctgggt gccctgaaag ggcccttccc ctcccccact cctctaagac   4320

aaagtagatt cttacaaggc cctttccttt ggaacaagac agccttcact tttctgagtt   4380

cttgaagcat ttcaaagccc tgcctctgtg tagccgccct gagagagaat agagctgcca   4440

ctgggcacct gcgcacaggt gggaggaaag ggcctggcca gtcctggtcc tggctgcact   4500

cttgaactgg gcgaatgtct tatttaatta ccgtgagtga catagcctca tgttctgtgg   4560

gggtcatcag ggagggttag gaaaaccaca aacggagccc ctgaaagcct cacgtatttc   4620

acagagcacg cctgccatct tctccccgag gctgccccag gccggagccc agatacgggg   4680

gctgtgactc tgggcaggga cccggggtct cctggacctt gacagagcag ctaactccga   4740

gagcagtggg caggtggccg cccctgaggc ttcacgccgg gagaagccac cttcccaccc   4800

cttcataccg cctcgtgcca gcagcctcgc acaggcccta gctttacgct catcacctaa   4860

acttgtactt tatttttctg atagaaatgg tttcctctgg atcgttttat gcggttctta   4920

cagcacatca cctctttgcc cccgacggct gtgacgcagc cggagggagg cactagtcac   4980

cgacagcggc cttgaagaca gagcaaagcg cccacccagg tcccccgact gcctgtctcc   5040

atgaggtact ggtcccttcc ttttgttaac gtgatgtgcc actatatttt acacgtatct   5100
```

cttggtatgc atcttttata gacgctcttt tctaagtggc gtgtgcatag cgtcctgccc 5160
tgccccctcg gggcctgtg gtggctcccc ctctgcttct cggggtccag tgcattttgt 5220
ttctgtatat gattctctgt ggtttttttt gaatccaaat ctgtcctctg tagtattttt 5280
taaataaatc agtgtttaca ttagaaaaaa aaaaaaaaaa aaaaa 5325

<210> SEQ ID NO 10
<211> LENGTH: 174
<212> TYPE: DNA
<213> ORGANISM: Homo sapiens

<400> SEQUENCE: 10
aagcccttca gcggccagta gcatctgact ttgagcctca gggtctgagt gaagccgctc 60
gttggaactc caaggaaaac cttctcgctg gacccagtga aatgacccc aacctttcg 120 ttgcactgta tgattttgtg gccagtggag ataacactct aagcataact aaag 174

<210> SEQ ID NO 11
<211> LENGTH: 25
<212> TYPE: DNA
<213> ORGANISM: Homo sapiens

<400> SEQUENCE: 11
cctgaggctc aaagtcagat gctac 25

<210> SEQ ID NO 12
<211> LENGTH: 1875
<212> TYPE: DNA
<213> ORGANISM: Homo sapiens

<400> SEQUENCE: 12
ggggggaggg tggcggctcg atgggggagc cgcctccagg gggccccccc gccctgtgcc 60
cacggcgcgg cccctttaag aggcccgcct ggctccgtca tccgcgccgc ggccacctcc 120
ccccggccct cccctcctg cggcgcagag tgcgggccgg gcgggagtgc ggcgagagcc 180
ggctggctga gcttagcgtc cgaggaggcg gcggcggcgg cggcggcacg gcggcggcgg 240
ggctgtgggg cggtgcggaa gcgagaggcg aggagcgcgc gggccgtggc cagagtctgg 300
cggcggcctg gcggagcgga gagcagcgcc cgcgcctcgc cgtgcggagg agccccgcac 360
acaatagcgg cgcgcgcagc ccgcgccctt ccccccggcg cgccccgccc cgcgcgccga 420
gcgccccgct ccgcctcacc tgccaccagg gagtgggcgg gcattgttcg ccgccgccgc 480
cgccgcgcgg gccatggggg ccgcccggcg cccggggccg ggctggcgag gcgccgcgcc 540
gccgctgaga cgggccccgc gcgcagcccg gcggcgcagg taaggccggc cgcgccatgg 600
tggacccggt gggcttcgcg gaggcgtgga aggcgcagtt cccggactca gagcccccgc 660
gcatggagct gcgctcagtg ggcgacatcg agcaggagct ggagcgctgc aaggcctcca 720
ttcggcgcct ggagcaggag gtgaaccagg agcgcttccg catgatctac ctgcagacgt 780
tgctggccaa ggaaaagaag agctatgacc ggcagcgatg ggcttccgg cgcgcggcgc 840 aggcccccga cggcgcctcc gagccccgag cgtccgcgtc gcgcccgcag ccagcgcccg 900
ccgacggagc cgacccgccg cccgccgagg agcccgaggc ccggcccgac ggcgagggtt 960
ctccgggtaa ggccaggccc gggaccgccc gcaggcccgg ggcagccgcg tcgggggaac 1020
gggacgaccg gggaccccc gccagcgtgg cggcgctcag gtccaacttc gagcggatcc 1080
gcaagggcca tggccagccc ggggcggacg ccgagaagcc cttctacgtg aacgtcgagt 1140

```
ttcaccacga gcgcggcctg gtgaaggtca acgacaaaga ggtgtcggac cgcatcagct   1200

ccctgggcag ccaggccatg cagatggagc gcaaaaagtc ccagcacggc gcgggctcga   1260

gcgtgggga tgcatccagg ccccttacc ggggacgctc ctcggagagc agctgcggcg   1320

tcgacggcga ctacgaggac gccgagttga acccccgctt cctgaaggac aacctgatcg   1380

acgccaatgg cggtagcagg cccccttggc cgcccctgga gtaccagccc taccagagca   1440

tctacgtcgg gggcatgatg gaaggggagg gcaagggccc gctcctgcgc agccagagca   1500

cctctgagca ggagaagcgc cttacctggc cccgcaggtc ctactccccc cggagttttg   1560

aggattgcgg aggcggctat accccggact gcagctccaa tgagaacctc acctccagcg   1620

aggaggactt ctcctctggc cagtccagcc gcgtgtcccc aagccccacc acctaccgca   1680

tgttccggga caaaagccgc tctccctcgc agaactcgca acagtccttc gacagcagca   1740

gtccccccac gccgcagtgc cataagcggc accggcactg cccggttgtc gtgtccgagg   1800

ccaccatcgt gggcgtccgc aagaccgggc agatctggcc caacgatggc gagggcgcct   1860

tccatggaga cgcag                                                     1875
```

<210> SEQ ID NO 13
<211> LENGTH: 20
<212> TYPE: DNA
<213> ORGANISM: Homo sapiens

<400> SEQUENCE: 13

```
tcgcaacagt ccttcgacag                                                  20
```

<210> SEQ ID NO 14
<211> LENGTH: 20
<212> TYPE: DNA
<213> ORGANISM: Homo sapiens

<400> SEQUENCE: 14

```
atcgtgggcg tccgcaagac                                                  20
```

<210> SEQ ID NO 15
<211> LENGTH: 19
<212> TYPE: DNA
<213> ORGANISM: Homo sapiens

<400> SEQUENCE: 15

```
cagagctgcc caccaagac                                                   19
```

<210> SEQ ID NO 16
<211> LENGTH: 23
<212> TYPE: DNA
<213> ORGANISM: Homo sapiens

<400> SEQUENCE: 16

```
agaaggcgct catcttcatt cag                                              23
```

<210> SEQ ID NO 17
<211> LENGTH: 23
<212> TYPE: DNA
<213> ORGANISM: Homo sapiens

<400> SEQUENCE: 17

```
ctgagatgcc tcactccaag ggc                                              23
```

<210> SEQ ID NO 18
<211> LENGTH: 3416

<212> TYPE: DNA
<213> ORGANISM: Homo sapiens

<400> SEQUENCE: 18

```
gggaaagctt gcatgcctgc aggtcgactc tagaggatct actagtcata tggattcatg     60
cagatggagc gcaaaaagtc ccagcacggc gcgggctcga gcgtgggggga tgcatccagg    120
ccccccttacc ggggacgctc ctcggagagc agctgcggcg tcgacggcga ctacgaggac    180
gccgagttga acccccgctt cctgaaggac aacctgatcg acgccaatgg cggtagcagg    240
ccccccttggc cgcccctgga gtaccagccc taccagagca tctacgtcgg gggcatgatg    300
gaaggggagg gcaagggccc gctcctgcgc agccagagca cctctgagca ggagaagcgc    360
cttacctggc cccgcaggtc ctactccccc cggagttttg aggattgcgg aggcggctat    420
accccggact gcagctccaa tgagaacctc acctccagcg aggaggactt ctcctctggc    480
cagtccagcc gcgtgtcccc aagccccacc acctaccgca tgttccggga caaaagccgc    540
tctccctcgc agaactcgca acagtccttc gacagcagca gtccccccac gccgcagtgc    600
cataagcggc accggcactg cccggttgtc gtgtccgagg ccaccatcgt gggcgtccgc    660
aagaccgggc agatctggcc caacgatggc gagggcgcct tccatggaga cgcagatggc    720
tcgttcggaa caccacctgg atacggctgc gctgcagacc gggcagagga gcagcgccgg    780
caccaagatg ggctgcccta cattgatgac tcgccctcct catcgcccca cctcagcagc    840
aagggcaggg gcagccggga tgcgctggtc tcgggagccc tggagtccac taaagcgagt    900
gagctggact tggaaaaggg cttggagatg agaaaatggg tcctgtcggg aatcctggct    960
agcgaggaga cttacctgag ccacctggag gcactgctgc tgcccatgaa gcctttgaaa   1020
gccgctgcca ccacctctca gccggtgctg acgagtcagc agatcgagac catcttcttc   1080
aaagtgcctg agctctacga gatccacaag gagttctatg atgggctctt cccccgcgtg   1140
cagcagtgga gccaccagca gcgggtgggc gacctcttcc agaagctggc cagccagctg   1200
ggtgtgtacc gggccttcgt ggacaactac ggagttgcca tggaaatggc tgagaagtgc   1260
tgtcaggcca atgctcagtt tgcagaaatc tccgagaacc tgagagccag aagcaacaaa   1320
gatgccaagg atccaacgac caagaactct ctggaaactc tgctctacaa gcctgtggac   1380
cgtgtgacga ggagcacgct ggtcctccat gacttgctga agcacactcc tgccagccac   1440
cctgaccacc ccttgctgca ggacgccctc cgcatctcac agaacttcct gtccagcatc   1500
aatgaggaga tcacaccccg acggcagtcc atgacggtga agaagggaga gcaccggcag   1560
ctgctgaagg acagcttcat ggtggagctg gtggaggggg cccgcaagct gcgccacgtc   1620
ttcctgttca ccgacctgct tctctgcacc aagctcaaga agcagagcgg aggcaaaacg   1680
cagcagtatg actgcaaatg gtacattccg ctcacggatc tcagcttcca gatggtggat   1740
gaactggagg cagtgcccaa catccccctg gtgcccgatg aggagctgga cgctttgaag   1800
atcaagatct cccagatcaa gaatgacatc cagagagaga agagggcgaa caagggcagc   1860
aaggctacgg agaggctgaa gaagaagctg tcggagcagg agtcactgct gctgcttatg   1920
tctcccagca tggccttcag ggtgcacagc cgcaacggca agagttacac gttcctgatc   1980
tcctctgact atgagcgtgc agagtggagg gagaacatcc gggagcagca gaagaagtgt   2040
ttcagaagct tctccctgac atccgtggag ctgcagatgc tgaccaactc gtgtgtgaaa   2100
ctccagactg tccacagcat tccgctgacc atcaataagg aagatgatga gtctccgggg   2160
ctctatgggt ttctgaatgt catcgtccac tcagccactg gatttaagca gagttcaaaa   2220
```

```
gcccttcagc ggccagtagc atctgacttt gagcctcagg gtctgagtga agccgctcgt   2280

tggaactcca aggaaaacct tctcgctgga cccagtgaaa atgaccccaa ccttttcgtt   2340

gcactgtatg attttgtggc cagtggagat aacactctaa gcataactaa aggtgaaaag   2400

ctccgggtct taggctataa tcacaatggg gaatggtgtg aagcccaaac caaaaatggc   2460

caaggctggg tcccaagcaa ctacatcacg ccagtcaaca gtctggagaa acactcctgg   2520

taccatgggc ctgtgtcccg caatgccgct gagtatctgc tgagcagcgg gatcaatggc   2580

agcttcttgg tgcgtgagag tgagagcagt cctggccaga ggtccatctc gctgagatac   2640

gaagggaggg tgtaccatta caggatcaac actgcttctg atggcaagct ctacgtctcc   2700

tccgagagcc gcttcaacac cctggccgag ttggttcatc atcattcaac ggtggccgac   2760

gggctcatca ccacgctcca ttatccagcc ccaaagcgca acaagcccac tgtctatggt   2820

gtgtccccca actacgacaa gtgggagatg gaacgcacgg acatcaccat gaagcacaag   2880

ctgggcgggg gccagtacgg ggaggtgtac gagggcgtgt ggaagaaata cagcctgacg   2940

gtggccgtga agaccttgaa ggaggacacc atggaggtgg aagagttctt gaaagaagct   3000

gcagtcatga aagagatcaa acaccctaac ctggtgcagc tccttggggt ctgcacccgg   3060

gagcccccgt tctatatcat cactgagttc atgacctacg ggaacctcct ggactacctg   3120

agggagtgca accggcagga ggtgaacgcc gtggtgctgc tgtacatggc cactcagatc   3180

tcgtcagcca tggagtacct ggagaagaaa aacttcatcc acagagatct tgctgcccga   3240

aactgcctgg taggggagaa ccacttggtg aaggtagctg attttggcct gagcaggttg   3300

atgacagggg acacctacac agcccatgct ggagccaagt tccccatcaa atggactgca   3360

cccgagagcc tggcctacaa caagttctcc atcaagtccg acgtctgggc agaatt       3416
```

<210> SEQ ID NO 19
<211> LENGTH: 580
<212> TYPE: DNA
<213> ORGANISM: Homo sapiens

<400> SEQUENCE: 19

```
gggaaagctt gcatgcctgc aggtcgactc tagaggatct actagtcata tggattcctc     60

acctccagcg aggaggactt ctcctctggc cagtccagcc gcgtgtcccc aagccccacc    120

acctaccgca tgttccggga caaaagccgc tctccctcgc agaactcgca acagtccttc    180

gacagcagca gtcccccac gccgcagtgc cataagcggc accggcactg cccggttgtc     240

gtgtccgagg ccaccatcgt gggcgtccgc aagaccgggc agatctggcc caacgatggc    300

gagggcgcct tccatggaga cgcagaagcc cttcagcggc cagtagcatc tgactttgag    360

cctcagggtc tgagtgaagc cgctcgttgg aactccaagg aaaaccttct cgctggaccc    420

agtgaaaatg accccaacct tttcgttgca ctgtatgatt ttgtggccag tggagataac    480

actctaagca taactaaagg tgaaaagctc cgggtcttag gctataatca caatggggaa    540

tggtgtgaag cccaaatcgg atccccgggt accgagctcg                          580
```

<210> SEQ ID NO 20
<211> LENGTH: 759
<212> TYPE: DNA
<213> ORGANISM: Homo sapiens

<400> SEQUENCE: 20

```
gggaaagctt gcatgcctgc aggtcgactc tagaggatct actagtcata tggattgttg     60

gcagtggaat ccctctgacc ggccctcctt tgctgaaatc caccaagcct ttgaaacaat    120
```

-continued

```
gttccaggaa tccagtatct cagacgaagt ggaaaaggag ctggggaaac aaggcgtccg    180

tggggctgtg agtaccttgc tgcaggcccc agagctgccc accaagacga ggacctccag    240

gagagctgca gagcacagag acaccactga cgtgcctgag atgcctcact ccaagggcca    300

gggagagagc gatcctctgg accatgagcc tgccgtgtct ccattgctcc ctcgaaaaga    360

gcgaggtccc ccggagggcg gcctgaatga agatgagcgc cttctcccca aagacaaaaa    420

gaccaacttg ttcagcgcct tgatcaagaa gaagaagaag acagccccaa cccctcccaa    480

acgcagcagc tccttccggg agatggacgg ccagccggag cgcagagggg ccggcgagga    540

agagggccga gacatcagca acggggcact ggctttcacc cccttggaca cagctgaccc    600

agccaagtcc ccaaagccca gcaatggggc tggggtcccc aatggagccc tccgggagtc    660

cgggggctca ggcttccggt ctccccacct gtggaagaag tccagcacgc tgaccagcag    720

ccgcctagca atcggatccc cgggtaccga gctcgaatt                            759
```